(12) United States Patent
Snow et al.

(10) Patent No.: US 9,051,253 B2
(45) Date of Patent: Jun. 9, 2015

(54) COMPOUNDS, COMPOSITIONS AND METHODS FOR THE TREATMENT OF AMYLOID DISEASES AND SYNUCLEINOPATHIES SUCH AS ALZHEIMER'S DISEASE, TYPE 2 DIABETES, AND PARKINSON'S

(71) Applicants: Alan D. Snow, Lynnwood, WA (US); Beth Nguyen, Trophy Club, TX (US); Gerardo Castillo, Bothell, WA (US); Virginia Sanders, San Francisco, CA (US); Thomas Lake, Snohomish, WA (US); Lesley Larsen, Dunedin (NZ)

(72) Inventors: Alan D. Snow, Lynnwood, WA (US); Beth Nguyen, Trophy Club, TX (US); Gerardo Castillo, Bothell, WA (US); Virginia Sanders, San Francisco, CA (US); Thomas Lake, Snohomish, WA (US); Lesley Larsen, Dunedin (NZ)

(73) Assignee: PROTEOTECH INC., Kirkland, WA (US)

(*) Notice: Subject to any disclaimer, the term of this patent is extended or adjusted under 35 U.S.C. 154(b) by 0 days.

(21) Appl. No.: 13/887,762

(22) Filed: May 6, 2013

(65) Prior Publication Data
US 2013/0245128 A1    Sep. 19, 2013

Related U.S. Application Data

(60) Division of application No. 13/413,417, filed on Mar. 6, 2012, now Pat. No. 8,586,585, which is a division of application No. 12/837,721, filed on Jul. 16, 2010, now Pat. No. 8,163,957, which is a continuation of application No. 12/269,017, filed on Nov. 11, 2008, (Continued)

(51) Int. Cl.
| | |
|---|---|
| A61K 31/047 | (2006.01) |
| A61K 31/05 | (2006.01) |
| C07C 49/248 | (2006.01) |
| C07C 39/15 | (2006.01) |
| C07C 39/16 | (2006.01) |
| C07C 39/17 | (2006.01) |
| C07C 45/62 | (2006.01) |
| C07C 45/64 | (2006.01) |
| C07C 49/83 | (2006.01) |
| C07C 49/835 | (2006.01) |
| C07C 69/017 | (2006.01) |
| C07C 215/50 | (2006.01) |
| C07C 231/02 | (2006.01) |
| C07C 235/34 | (2006.01) |
| C07C 235/38 | (2006.01) |
| C07C 235/48 | (2006.01) |
| C07C 235/54 | (2006.01) |
| C07C 235/56 | (2006.01) |
| C07C 237/22 | (2006.01) |
| C07C 275/34 | (2006.01) |
| C07D 207/16 | (2006.01) |
| C07D 211/74 | (2006.01) |
| C07D 213/30 | (2006.01) |
| C07D 213/69 | (2006.01) |
| C07D 213/85 | (2006.01) |
| C07D 221/08 | (2006.01) |
| C07D 221/18 | (2006.01) |
| C07D 231/06 | (2006.01) |
| C07D 241/08 | (2006.01) |
| C07D 263/38 | (2006.01) |
| C07D 265/38 | (2006.01) |

(Continued)

(52) U.S. Cl.
CPC ............. *C07C 49/248* (2013.01); *A61K 31/047* (2013.01); *C07C 39/15* (2013.01); *C07C 39/16* (2013.01); *C07C 39/17* (2013.01); *C07C 45/62* (2013.01); *C07C 45/64* (2013.01); *C07C 49/83* (2013.01); *C07C 49/835* (2013.01); *C07C 69/017* (2013.01); *C07C 215/50* (2013.01); *C07C 231/02* (2013.01); *C07C 235/34* (2013.01); *C07C 235/38* (2013.01); *C07C 235/48* (2013.01); *C07C 235/54* (2013.01); *C07C 235/56* (2013.01); *C07C 237/22* (2013.01); *C07C 275/34* (2013.01); *C07D 207/16* (2013.01); *C07D 211/74* (2013.01); *C07D 213/30* (2013.01); *C07D 213/69* (2013.01); *C07D 213/85* (2013.01); *C07D 221/08* (2013.01); *C07D 221/18* (2013.01); *C07D 231/06* (2013.01); *C07D 241/08* (2013.01); *C07D 263/38* (2013.01); *C07D 265/38* (2013.01); *C07D 295/096* (2013.01); *C07D 295/192* (2013.01); *C07D 311/60* (2013.01); *C07D 317/50* (2013.01); *C07D 317/54* (2013.01); *C07D 317/58* (2013.01); *C07D 317/60* (2013.01); *C07D 317/66* (2013.01); *C07D 317/68* (2013.01); *C07D 333/16* (2013.01); *C07D 405/14* (2013.01); *C07D 407/14* (2013.01); *C07D 409/14* (2013.01); *C07D 413/14* (2013.01); *C07D 451/06* (2013.01); *C07D 471/04* (2013.01); *C07D 487/08* (2013.01); *C07D 491/08* (2013.01)

(58) Field of Classification Search
CPC .. A61K 31/4105; A61K 31/047; A61K 31/05
USPC ........................................................ 564/155
See application file for complete search history.

(56) References Cited

U.S. PATENT DOCUMENTS 2,769,817 A    11/1956    Martin

*Primary Examiner* — Yong Chong
(74) *Attorney, Agent, or Firm* — Rebecca Eagen

(57) ABSTRACT

The use of 3,4,3',4'-tetrahydroxychalcone in the treatment of amyloid diseases, especially Aβ amyloidosis, such as observed in Alzheimer's disease, IAPP amyloidosis, such as observed in type 2 diabetes, and synucleinopathies, such as observed in Parkinson's disease.

5 Claims, No Drawings

Related U.S. Application Data now abandoned, which is a continuation of application No. 10/452,851, filed on May 30, 2003, now Pat. No. 7,514,583, application No. 13/887,762, which is a continuation-in-part of application No. 13/268,170, filed on Oct. 7, 2011, now Pat. No. 8,754,133, which is a continuation of application No. 11/704,421, filed on Feb. 10, 2007, now abandoned, which is a continuation-in-part of application No. 11/503,400, filed on Jan. 26, 2007, now abandoned, said application No. 13/268,170 is a continuation of application No. 13/188,636, filed on Jul. 22, 2011, now abandoned, which is a continuation-in-part of application No. 12/837,721.

(60) Provisional application No. 60/385,144, filed on May 31, 2002, provisional application No. 60/409,100, filed on Sep. 9, 2002, provisional application No. 60/412,272, filed on Sep. 20, 2002, provisional application No. 60/435,880, filed on Dec. 20, 2002, provisional application No. 60/463,104, filed on Apr. 14, 2003.

(51) Int. Cl.

| | |
|---|---|
| *C07D 295/096* | (2006.01) |
| *C07D 295/192* | (2006.01) |
| *C07D 311/60* | (2006.01) |
| *C07D 317/50* | (2006.01) |
| *C07D 317/54* | (2006.01) |
| *C07D 317/58* | (2006.01) |
| *C07D 317/60* | (2006.01) |
| *C07D 317/66* | (2006.01) |
| *C07D 317/68* | (2006.01) |
| *C07D 333/16* | (2006.01) |
| *C07D 405/14* | (2006.01) |
| *C07D 407/14* | (2006.01) |
| *C07D 409/14* | (2006.01) |
| *C07D 413/14* | (2006.01) |
| *C07D 451/06* | (2006.01) |
| *C07D 471/04* | (2006.01) |
| *C07D 487/08* | (2006.01) |
| *C07D 491/08* | (2006.01) |

COMPOUNDS, COMPOSITIONS AND METHODS FOR THE TREATMENT OF AMYLOID DISEASES AND SYNUCLEINOPATHIES SUCH AS ALZHEIMER'S DISEASE, TYPE 2 DIABETES, AND PARKINSON'S

CROSS-REFERENCE TO RELATED APPLICATION

This application is a divisional of 13/413,417 filed Mar. 6, 2012, which is a divisional of 12/837,721 filed Jul. 16, 2010, now U.S. Pat. No. 8,163,957, which claimed the benefit of priority under 35 U.S.C. §120 to, and was a continuation of U.S. application Ser. No. 12/269,017, filed Nov. 11, 2008 which is a continuation of U.S. application Ser. No. 10/452, 851, filed May 30, 2003, now U.S. Pat. No. 7,514,583, issued on Apr. 7, 2009, which claimed priority under 35 U.S.C. 119(e) to:
(1) U.S. Provisional Application No. 60/385,144, filed May 31, 2002,
(2) U.S. Provisional Application No. 60/409,100, filed Sep. 9, 2002,
(3) U.S. Provisional Application No. 60/412,272, filed Sep. 20, 2002,
(4) U.S. Provisional Application No. 60/435,880, filed Dec. 20, 2002, and
(5) U.S. Provisional Application No. 60/463,104, filed Apr. 14, 2003.

This application is a continuation-in-part of U.S. application Ser. No. 13/268,170 filed Oct. 7, 2011 which is a continuation of U.S. application Ser. No. 11/704,421 filed Feb. 10, 2007, now abandoned, which is a continuation-in-part of U.S. application Ser. No. 11/503,400 filed Jan. 26, 2007, now abandoned, which is a continuation-in-part of U.S. application Ser. No. 12/475,097 filed May 29, 2009, now abandoned, which is a continuation-in-part of U.S. application Ser. No. 10/077,596 filed Feb. 15, 2002 now abandoned, which is a continuation-in-part of U.S. application Ser. No. 10/053,625, filed Nov. 2, 2001, now U.S. Pat. No. 6,929,808, which claimed priority under 35 U.S.C. 119(e) to:
(1) U.S. Provisional Application No. 60/245,958, filed Nov. 3, 2000, and
(2) U.S. Provisional Application No. 60/271,777, filed Feb. 27, 2001.

U.S. application Ser. No. 13/268,170 is a continuation of U.S. application Ser. No. 13/188,636 filed Jul. 22, 2011 now abandoned, which is a continuation-in-part of U.S. application Ser. No. 12/837,721 filed Jul. 16, 2010, now U.S. Pat. No. 8,163,957. (See above.)
The entire contents of all of these applications are incorporated by reference into this application.

TECHNICAL FIELD

This invention relates to bis- and tris-dihydroxyaryl compounds and their methylenedioxy analogs and pharmaceutically acceptable esters, their synthesis, pharmaceutical compositions containing them, and their use in the treatment of amyloid diseases, especially Aβ amyloid disease, such as observed in Alzheimer's disease, IAPP amyloid disease, such as observed in type 2 diabetes, and synucleinopathies, such as observed in Parkinson's disease, and in the manufacture of medicaments for such treatment.

BACKGROUND OF THE INVENTION

Alzheimer's disease is characterized by the accumulation of a 39-43 amino acid peptide termed the β-amyloid protein or Aβ, in a fibrillar form, existing as extracellular amyloid plaques and as amyloid within the walls of cerebral blood vessels. Fibrillar Aβ amyloid deposition in Alzheimer's disease is believed to be detrimental to the patient and eventually leads to toxicity and neuronal cell death, characteristic hallmarks of Alzheimer's disease. Accumulating evidence implicates amyloid, and more specifically, the formation, deposition, accumulation and/or persistence of Aβ fibrils, as a major causative factor of Alzheimer's disease pathogenesis. In addition, besides Alzheimer's disease, a number of other amyloid diseases involve formation, deposition, accumulation and persistence of Aβ fibrils, including Down's syndrome, disorders involving congophilic angiopathy, such as but not limited to, hereditary cerebral hemorrhage of the Dutch type, inclusion body myositosis, dementia pugilistica, cerebral β-amyloid angiopathy, dementia associated with progressive supranuclear palsy, dementia associated with cortical basal degeneration and mild cognitive impairment.

Parkinson's disease is another human disorder characterized by the formation, deposition, accumulation and/or persistence of abnormal fibrillar protein deposits that demonstrate many of the characteristics of amyloid. In Parkinson's disease, an accumulation of cytoplasmic Lewy bodies consisting of filaments of α-synuclein/NAC (non-Aβ component) are believed important in the pathogenesis and as therapeutic targets. New agents or compounds able to inhibit α-synuclein and/or NAC formation, deposition, accumulation and/or persistence, or disrupt pre-formed α-synudein/NAC fibrils (or portions thereof) are regarded as potential therapeutics for the treatment of Parkinson's and related synucleinopathies. NAC is a 35 amino acid fragment of α-synuclein that has the ability to form amyloid-like fibrils either in vitro or as observed in the brains of patients with Parkinson's disease. The NAC fragment of α-synuclein is a relative important therapeutic target as this portion of α-synuclein is believed crucial for formation of Lewy bodies as observed in all patients with Parkinson's disease, synucleinopathies and related disorders.

A variety of other human diseases also demonstrate amyloid deposition and usually involve systemic organs (i.e. organs or tissues lying outside the central nervous system), with the amyloid accumulation leading to organ dysfunction or failure. These amyloid diseases (discussed below) leading to marked amyloid accumulation in a number of different organs and tissues, are known as systemic amyloidoses. In other amyloid diseases, single organs may be affected such as the pancreas in 90% of patients with type 2 diabetes. In this type of amyloid disease, the beta-cells in the islets of Langerhans in pancreas are believed to be destroyed by the accumulation of fibrillar amyloid deposits consisting primarily of a protein known as islet amyloid polypeptide (IAPP). Inhibiting or reducing such IAPP amyloid fibril formation, deposition, accumulation and persistence is believed to lead to new effective treatments for type 2 diabetes. In Alzheimer's disease, Parkinson's and "systemic" amyloid diseases, there is currently no cure or effective treatment, and the patient usually dies within 3 to 10 years from disease onset.

The amyloid diseases (amyloidoses) are classified according to the type of amyloid protein present as well as the underlying disease. Amyloid diseases have a number of common characteristics including each amyloid consisting of a unique type of amyloid protein. The amyloid diseases include, but are not limited to, the amyloid associated with Alzheimer's disease, Down's syndrome, hereditary cerebral hemorrhage with amyloidosis of the Dutch type, dementia pugilistica, inclusion body myositosis (Askanas et al, *Ann. Neurol.* 43:521-560, 1993) and mild cognitive impairment (where the specific amyloid is referred to as beta-amyloid protein or Aβ), the amyloid associated with chronic inflammation, various forms of malignancy and Familial Mediterranean Fever (where the specific amyloid is referred to as AA amyloid or inflammation-associated amyloidosis), the amyloid associated with multiple myeloma and other B-cell dyscrasias (where the specific amyloid is referred to as AL amyloid), the amyloid associated with type 2 diabetes (where the specific amyloid protein is referred to as amylin or islet amyloid polypeptide or IAPP), the amyloid associated with the prion diseases including Creutzfeldt-Jakob disease, Gerstmann-Straussler syndrome, kuru and animal scrapie (where the specific amyloid is referred to as PrP amyloid), the amyloid associated with long-term hemodialysis and carpal tunnel syndrome (where the specific amyloid is referred to as $\alpha_2$-microglobulin amyloid), the amyloid associated with senile cardiac amyloidosis and Familial Amyloidotic Polyneuropathy (where the specific amyloid is referred to as transthyretin or prealbumin), and the amyloid associated with endocrine tumors such as medullary carcinoma of the thyroid (where the specific amyloid is referred to as variants of procalcitonin). In addition, the α-synuclein protein which forms amyloid-like fibrils, and is Congo red and Thioflavin S positive (specific stains used to detect amyloid fibrillar deposits), is found as part of Lewy bodies in the brains of patients with Parkinson's disease, Lewy body disease (Lewy in *Handbuch der Neurologie*, M. Lewandowski, ed., Springer, Berlin pp. 920-933, 1912; Pollanen et al, *J. Neuropath. Exp. Neurol.* 52:183-191, 1993; Spillantini et al, *Proc. Natl. Acad. Sci. USA* 95:6469-6473, 1998; Arai et al, *Neurosci. Lett.* 259:83-86, 1999), multiple system atrophy (Wakabayashi et al, *Acta Neuropath.* 96:445-452, 1998), dementia with Lewy bodies, and the Lewy body variant of Alzheimer's disease. For purposes of this disclosure, Parkinson's disease, due to the fact that fibrils develop in the brains of patients with this disease (which are Congo red and Thioflavin S positive, and which contain predominant beta-pleated sheet secondary structure), is now regarded as a disease that also displays the characteristics of an amyloid-like disease.

Systemic amyloidoses which include the amyloid associated with chronic inflammation, various forms of malignancy and familial Mediterranean fever (i.e. AA amyloid or inflammation-associated amyloidosis) (Benson and Cohen, *Arth. Rheum.* 22:36-42, 1979; Kamei et al, *Acta Path. Jpn.* 32:123-133, 1982; McAdam et al., *Lancet* 2:572-573, 1975; Metaxas, *Kidney Int.* 20:676-685, 1981), and the amyloid associated with multiple myeloma and other B-cell dyscrasias (i.e. AL amyloid) (Harada et al., *J. Histochem. Cytochem.* 19:1-15, 1971), as examples, are known to involve amyloid deposition in a variety of different organs and tissues generally lying outside the central nervous system. Amyloid deposition in these diseases may occur, for example, in liver, heart, spleen, gastrointestinal tract, kidney, skin, and/or lungs (Johnson et al, *N. Engl. J. Med.* 321:513-518, 1989). For most of these amyloidoses, there is no apparent cure or effective treatment and the consequences of amyloid deposition can be detrimental to the patient. For example, amyloid deposition in the kidney may lead to renal failure, whereas amyloid deposition in the heart may lead to heart failure. For these patients, amyloid accumulation in systemic organs leads to eventual death generally within 3-5 years. Other amyloidoses may affect a single organ or tissue such as observed with the Aβ amyloid deposits found in the brains of patients with Alzheimer's disease and Down's syndrome: the PrP amyloid deposits found in the brains of patients with Creutzfeldt-Jakob disease, Gerstmann-Straussler syndrome, and kuru; the islet amyloid (IAPP) deposits found in the islets of Langerhans in the pancreas of 90% of patients with type 2 diabetes (Johnson et al, *N. Engl. J. Med.* 321:513-518, 1989; *Lab. Invest.* 66:522 535, 1992); the $\alpha_2$-microglobulin amyloid deposits in the medial nerve leading to carpal tunnel syndrome as observed in patients undergoing long-term hemodialysis (Geyjo et al, *Biochem. Biophys. Res. Comm.* 129:701-706, 1985; *Kidney Int.* 30:385-390, 1986); the prealbumin/transthyretin amyloid observed in the hearts of patients with senile cardiac amyloid; and the prealbumin/transthyretin amyloid observed in peripheral nerves of patients who have familial amyloidotic polyneuropathy (Skinner and Cohen, *Biochem. Biophys. Res. Comm.* 99:1326-1332, 1981; Saraiva et al, *J. Lab. Clin. Med.* 102:590-603, 1983; *J. Clin. Invest.* 74:104-119, 1984; Tawara et al, *J. Lab. Clin. Med.* 98:811-822, 1989).

Alzheimer's disease also puts a heavy economic burden on society. A recent study estimated that the cost of caring for one Alzheimer's disease patient with severe cognitive impairments at home or in a nursing home, is more than $47,000 per year (*A Guide to Understanding Alzheimer's Disease and Related Disorders*). For a disease that can span from 2 to 20 years, the overall cost of Alzheimer's disease to families and to society is staggering. The annual economic toll of Alzheimer's disease in the United States in terms of health care expenses and lost wages of both patients and their caregivers is estimated at $80 to $100 billion (2003 *Progress Report on Alzheimer's Disease*).

Tacrine hydrochloride ("Cognex"), the first FDA approved drug for Alzheimer's disease, is a acetylcholinesterase inhibitor (Cutler and Sramek, *N. Engl. J. Med.* 328:808 810, 1993). However, this drug has showed limited success in producing cognitive improvement in Alzheimer's disease patients and initially had major side effects such as liver toxicity. The second FDA approved drug, donepezil ("Aricept"), which is also an acetylcholinesterase inhibitor, is more effective than tacrine, by demonstrating slight cognitive improvement in Alzheimer's disease patients (Barner and Gray, *Ann. Pharmacotherapy* 32:70-77, 1998; Rogers and Friedhoff, *Eur. Neuropsych.* 8:67-75, 1998), but is not believed to be a cure. Therefore, it is clear that there is a need for more effective treatments for Alzheimer's disease patients.

Amyloid as a Therapeutic Target for Alzheimer's Disease

Alzheimer's disease is characterized by the deposition and accumulation of a 39-43 amino acid peptide termed the beta-amyloid protein, Aβ or β/A4 (Glenner and Wong, *Biochem. Biophys. Res. Comm.* 120:885-890, 1984; Masters et al., *Proc. Natl. Acad. Sci. USA* 82:4245-4249, 1985; Husby et al., *Bull. WHO* 71:105-108, 1993). Aβ is derived by protease cleavage from larger precursor proteins termed β-amyloid precursor proteins (APPs) of which there are several alternatively spliced variants. The most abundant forms of the APPs include proteins consisting of 695, 751 and 770 amino acids (Tanzi et al., *Nature* 31:528-530, 1988).

The small Aβ peptide is a major component that makes up the amyloid deposits of "plaques" in the brains of patients with Alzheimer's disease. In addition, Alzheimer's disease is characterized by the presence of numerous neurofibrillary "tangles", consisting of paired helical filaments which abnormally accumulate in the neuronal cytoplasm (Grundke-Iqbal et al., *Proc. Natl. Acad. Sci. USA* 83:4913-4917, 1986; Kosik et al., *Proc. Natl. Acad. Sci. USA* 83:4044-4048, 1986; Lee et al., *Science* 251:675-678, 1991). The pathological hallmark of Alzheimer's disease is therefore the presence of "plaques" and "tangles", with amyloid being deposited in the central core of the plaques. The other major type of lesion found in the Alzheimer's disease brain is the accumulation of amyloid in the walls of blood vessels, both within the brain parenchyma and in the walls of meningeal vessels that lie outside the brain. The amyloid deposits localized to the walls of blood vessels are referred to as cerebrovascular amyloid or congophilic angiopathy (Mandybur, *J. Neuropath. Exp. Neurol.* 45:79-90, 1986; Pardridge et al., *J. Neurochem.* 49:1394-1401, 1987)

For many years there has been an ongoing scientific debate as to the importance of "amyloid" in Alzheimer's disease, and whether the "plaques" and "tangles" characteristic of this disease were a cause or merely a consequence of the disease. Within the last few years, studies now indicate that amyloid is indeed a causative factor for Alzheimer's disease and should not be regarded as merely an innocent bystander. The Alzheimer's Aβ protein in cell culture has been shown to cause degeneration of nerve cells within short periods of time (Pike et al., *Br. Res.* 563:311-314, 1991; *J. Neurochem.* 64:253-265, 1995). Studies suggest that it is the fibrillar structure (consisting of a predominant β-pleated sheet secondary structure), characteristic of all amyloids, that is responsible for the neurotoxic effects. Aβ has also been found to be neurotoxic in slice cultures of hippocampus (Harrigan et al., *Neurobiol. Aging* 16:779-789, 1995) and induces nerve cell death in transgenic mice (Games et al., *Nature* 373:523-527, 1995; Hsiao et al., *Science* 274:99-102, 1996). Injection of the Alzheimer's Aβ into rat brain also causes memory impairment and neuronal dysfunction (Flood et al., *Proc. Natl. Acad. Sci. USA* 88:3363-3366, 1991; *Br. Res.* 663:271-276, 1994).

Probably, the most convincing evidence that Aβ amyloid is directly involved in the pathogenesis of Alzheimer's disease comes from genetic studies. It was discovered that the production of Aβ can result from mutations in the gene encoding, its precursor, β-amyloid precursor protein (Van Broeckhoven et al., *Science* 248:1120-1122, 1990; Murrell et al., *Science* 254:97-99, 1991; Haass et al., *Nature Med.* 1:1291-1296, 1995). The identification of mutations in the beta-amyloid precursor protein gene that cause early onset familial Alzheimer's disease is the strongest argument that amyloid is central to the pathogenetic process underlying this disease. Four reported disease-causing mutations have been discovered which demonstrate the importance of Aβ in causing familial Alzheimer's disease (reviewed in Hardy, *Nature Genet.* 1:233-234, 1992). All of these studies suggest that providing a drug to reduce, eliminate or prevent fibrillar Aβ formation, deposition, accumulation and/or persistence in the brains of human patients will serve as an effective therapeutic.

Parkinson's Disease and Synucleinopathies

Parkinson's disease is a neurodegenerative disorder that is pathologically characterized by the presence of intracytoplasmic Lewy bodies (Lewy in *Handbuch der Neurologie*, M. Lewandowski, ed., Springer, Berlin, pp. 920-933, 1912; Pollanen et al., *J. Neuropath. Exp. Neurol.* 52:183-191, 1993), the major components of which are filaments consisting of α-synuclein (Spillantini et al., *Proc. Natl. Acad. Sci. USA* 95:6469-6473, 1998; Arai et al., *Neurosci. Lett.* 259:83-86, 1999), an 140-amino acid protein (Ueda et al., *Proc. Natl. Acad. Sci. USA* 90:11282-11286, 1993). Two dominant mutations in α-synuclein causing familial early onset Parkinson's disease have been described suggesting that Lewy bodies contribute mechanistically to the degeneration of neurons in Parkinson's disease and related disorders (Polymeropoulos et al., *Science* 276:2045-2047, 1997; Kruger et al., *Nature Genet.* 18:106-108, 1998). Recently, in vitro studies have demonstrated that recombinant α-synuclein can indeed form Lewy body-like fibrils (Conway et al., *Nature Med.* 4:1318-1320, 1998; Hashimoto et al., *Brain Res.* 799:301-306, 1998; Nahri et al., *J. Biol. Chem.* 274:9843-9846, 1999). Most importantly, both Parkinson's disease-linked α-synuclein mutations accelerate this aggregation process, demonstrating that such in vitro studies may have relevance for Parkinson's disease pathogenesis. Alpha-synuclein aggregation and fibril formation fulfills of the criteria of a nucleation-dependent polymerization process (Wood et al., *J. Biol. Chem.* 274:19509-19512, 1999). In this regard α-synuclein fibril formation resembles that of Alzheimer's β-amyloid protein (Aβ) fibrils. Alpha-synuclein recombinant protein, and non-Aβ component (known as NAC), which is a 35-amino acid peptide fragment of α-synuclein, both have the ability to form fibrils when incubated at 37° C., and are positive with amyloid stains such as Congo red (demonstrating a red/green birefringence when viewed under polarized light) and Thioflavin S (demonstrating positive fluorescence) (Hashimoto et al., *Brain Res.* 799:301-306, 1998; Ueda et al., *Proc. Natl. Acad. Sci. USA* 90:11282-11286, 1993).

Synucleins are a family of small, presynaptic neuronal proteins composed of α-, β-, and γ-synucleins, of which only α-synuclein aggregates have been associated with several neurological diseases (Ian et al., *Clinical Neurosc. Res.* 1:445-455, 2001; Trojanowski and Lee, *Neurotoxicology* 23:457-460, 2002). The role of synucleins (and in particular, alpha-synuclein) in the etiology of a number of neurodegenerative and/or amyloid diseases has developed from several observations. Pathologically, synuclein was identified as a major component of Lewy bodies, the hallmark inclusions of Parkinson's disease, and a fragment thereof was isolated from amyloid plaques of a different neurological disease, Alzheimer's disease. Biochemically, recombinant α-synuclein was shown to form amyloid-like fibrils that recapitulated the ultrastructural features of alpha-synuclein isolated from patients with dementia with Lewy bodies, Parkinson's disease and multiple system atrophy. Additionally, the identification of mutations within the synuclein gene, albeit in rare cases of familial Parkinson's disease, demonstrated an unequivocal link between synuclein pathology and neurodegenerative diseases. The common involvement of α-synuclein in a spectrum of diseases such as Parkinson's disease, dementia with Lewy bodies, multiple system atrophy and the Lewy body variant of Alzheimer's disease has led to the classification of these diseases under the umbrella term of "synucleinopathies".

Parkinson's disease α-synuclein fibrils, like the Aβ fibrils of Alzheimer's disease, also consist of a predominantly β-pleated sheet structure. Therefore, compounds found to inhibit Alzheimer's disease Aβ amyloid fibril formation are also anticipated to be effective in the inhibition of α-synuclein/NAC fibril formation, as shown from Examples in the present invention. These compounds would therefore also serve as therapeutics for Parkinson's disease and other synucleinopathies, in addition to having efficacy as a therapeutic for Alzheimer's disease, type 2 diabetes, and other amyloid disorders.

Discovery and identification of new compounds or agents as potential therapeutics to arrest amyloid formation, deposition, accumulation and/or persistence that occurs in Alzheimer's disease, Parkinson's disease, type II diabetes, and other amyloidosis are desperately sought.

SUMMARY OF THE INVENTION

In a first aspect, this invention is bis- and tris-dihydroxyaryl compounds and their methylenedioxy analogs and pharmaceutically acceptable esters, and pharmaceutically acceptable salts thereof. The compounds are useful in the treatment of amyloid diseases and synucleinopathies.

The compounds are:

(1) compound of the formula:

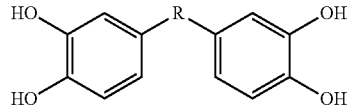

where:
R is a $C_1$-$C_{10}$ alkylene group, in which, when the number of carbon atoms is at least 2, there are optionally 1 or 2 non-adjacent double bonds; 1 to 3 non-adjacent methylene groups are optionally replaced by NR' (where R' is H, alkyl, or acyl), O, or S; and 1 or 2 methylene groups are optionally replaced by a carbonyl or hydroxymethylene group; and (2) the compounds that are:
3,4,3',4'-tetrahydroxybenzoin (compound 1); 3,4,3',4'-tetrahydroxydesoxybenzoin (compound 2); 3,4,3',4'-tetrahydroxydiphenylmethane (compound 3); 1,2-bis(3,4-dihydroxyphenyhethane (compound 4); 1,3-bis(3,4-dihydroxyphenyhpropane (compound 5); 3,4,3',4'-tetrahydroxychalcone (compound 6); 3,5-bis(3,4-dihydroxyphenyl)-1-methyl-2-pyrazoline (compound 7); 4,6-bis(3,4-dihydroxyphenyl)-3-cyano-2-methylpyridine (compound 8); 1,4-bis(3,4-dihydroxybenzyhpiperazine (compound 9); N,N'-bis(3,4-dihydroxybenzyl)-N,N'-dimethylethylenediamine (compound 10); 2,5-bis(3,4-dihydroxy-benzyl)-2,5-diaza[2.2.1]bicycloheptane (compound 11); N,N'-bis(3,4-dihydroxybenzyl)-trans-1,2-diamino-cyclohexane (compound 12); N,N'-bis(3,4-dihydroxybenzyl)-trans-1,4-diaminocyclohexane (compound 13); N,N'-bis(3,4-dihydroxybenzyl)-cis-1,3-bis(aminomethyl)cyclohexane (compound 14); N-(3,4-dihydroxy-benzyl)proline 3,4-dihydroxybenzylamide (compound 15); 2-(3,4-dihydroxybenzyl)isoquinoline-3-carboxylic acid 3,4-dihydroxyphenethylamide (compound 16); 2,6-bis(3,4-dihydroxybenzyl)-cyclohexanone (compound 17); 3,5-bis(3,4-dihydroxybenzyl)-1-methyl-4-piperidinone (compound 18); 2,4-bis(3,4-dihydroxybenzyl)-3-tropinone (compound 19); tris-(3,4-dihydroxybenzyl)methane (compound 20); α-(3,4-dihydroxybenzamido)-3,4-dihydroxycinnamic acid 3,4-dihydroxybenzyl amide (compound 21); 4-(3,4-dihydroxybenzylaminomethylene)-2-(3,4-dihydroxyphenyhoxazolin-5-one (compound 22); 1,4-bis(3,4-dihydroxybenzoyhpiperazine (compound 23); N,N'-bis(3,4-dihydroxybenzoyl)-N,N'-dimethylethylenediamine (compound 24); 2,5-bis(3,4-dihydroxybenzoyl)-2,5-diaza[2.2.1]bicyclo-heptane (compound 25); N,N'-bis(3,4-dihydroxybenzoyl)-trans-1,2-diaminocyclohexane (compound 26); N,N'-bis(3,4-dihydroxybenzoyl)-cis-1,3-bis(aminomethyl)cyclohexane (compound 27); 3,6-bis(3,4-dihydroxybenzyl)-2,5-diketopiperazine (compound 28); 3,6-bis(3,4-dihydroxybenzylidene)-1,4-dimethyl-2,5-diketopiperazine (compound 29); N-(3,4-dihydroxyphenylacetyl)proline 3,4-dihydroxyanilide (compound 30); 2,3-bis(3,4-dihydroxyphenyl)butane (compound 31); 1,3-bis(3,4-dihydroxybenzyhbenzene (compound 32); 1,4-bis(3,4-dihydroxybenzyhbenzene (compound 33); 2,6-bis(3,4-dihydroxybenzyl)pyridine (compound 34); 2,5-bis(3,4-dihydroxybenzyhthiophene (compound 35); 2,3-bis(3,4-dihydroxybenzyl)thiophene (compound 36); 1,2-bis(3,4-dihydroxyphenyl)-cyclohexane (compound 37); 1,4-bis(3,4-dihydroxyphenyhcyclohexane (compound 38); 3,7-bis(3,4-dihydroxyphenyl)bicyclo[3.3.0]octane (compound 39); 2,3-bis(3,4-dihydroxyphenyl)-1,7,7-trimethylbicyclo[2.2.1]heptane (compound 40); 1,2-bis(3,4-dihydroxyphenoxy)ethane (compound 41); 1,3-bis(3,4-dihydroxyphenoxy)propane (compound 42); trans-1,2-bis(3,4-dihydroxyphenoxy)-cyclopentane (compound 43); N-(3,4-dihydroxybenzyl)-3-(3,4-dihydroxyphenoxy)-2-hydroxypropylamine (compound 44); 3,4-dihydroxyphenoxyacetic acid 3,4-dihydroxyanilide (compound 45); 3,4-dihydroxyphenoxyacetic acid 3,4-dihydroxybenzylamide (compound 46); 3,4-dihydroxyphenoxyacetic acid 3,4-dihydroxyphenethylamide (compound 47); 3,4-dihydroxybenzoic acid p-(3,4-dihydroxy-phenoxy)anilide (compound 48); 3,4-dihydroxybenzoic acid o-(3,4-dihydroxyphenoxy)anilide (compound 49); 2,6-bis(3,4-dihydroxyphenoxy)pyridine (compound 50), 3,4-dihydroxybenzoic acid 3,4-dihydroxy-anilide (compound 51); 3,4-dihydroxybenzoic acid 3,4-dihydroxybenzylamide (compound 52); 3,4-dihydroxybenzoic acid 3,4-dihydroxyphenethylamide (compound 53); 3,4-dihydroxyphenylacetic acid 3,4-dihydroxyanilide (compound 54); 3,4-dihydroxyphenylacetic acid 3,4-dihydroxybenzylamide (compound 55); 3,4-dihydroxyphenylacetic acid 3,4-dihydroxyphenethylamide (compound 56); 3-(3,4-dihydroxyphenyl)propionic acid 3,4-dihydroxyanilide (compound 57); 3-(3,4-dihydroxyphenyl)propionic acid 3,4-dihydroxybenzylamide (compound 58); 3-(3,4-dihydroxyphenyl)propionic acid 3,4-dihydroxyphenethylamide (compound 59); 3,4-dihydroxycinnamic acid 3,4-dihydroxyanilide (compound 60); 3,4-dihydroxycinnamic acid 3,4-dihydroxybenzylamide (compound 61); 3,4-dihydroxy-cinnamic acid 3,4-dihydroxyphenethylamide (compound 62); oxalic acid bis(3,4-dihydroxyanilide) (compound 63); oxalic acid bis(3,4-dihydroxybenzylamide) (compound 64); oxalic acid bis(3,4-dihydroxyphenethylamide) (compound 65); succinic acid bis(3,4-dihydroxyanilide) (compound 66); succinic acid bis(3,4-dihydroxybenzylamide) (compound 67); succinic acid bis(3,4-dihydroxyphenethylamide) (compound 68); maleic acid bis(3,4-dihydroxyanilide) (compound 69); maleic acid bis(3,4-dihydroxybenzyl-amide) (compound 70); fumaric acid bis(3,4-dihydroxyanilide) (compound 71); fumaric acid bis(3,4-dihydroxybenzylamide) (compound 72); bis(3,4-dihydroxybenzyhamine (compound 73); N-(3,4-dihydroxybenzyl)-3,4-dihydroxyphenethylamine (compound 74); tris(3,4-dihydroxybenzyhamine (compound 75); 1,3-bis(3,4-dihydroxyphenyl)urea (compound 76); 1-(3,4-dihydroxyphenyl)-3-(3,4-dihydroxybenzyl)urea (compound 77); 1-(3,4-dihydroxyphenyl)-3-(3,4-dihydroxyphenethyl)urea (compound 78); 3-deoxy-3-(3,4-dihydroxybenzyl)aminoepicatechin (compound 79); 3-deoxy-3-(3,4-dihydroxyphenethyl)aminoepicatechin (compound 80); 2,3,6,7-tetrahydroxy-9,10-epoxy-9,10-dihydroacridine (compound 81); 10-aminoanthracene-1,2,7,8-tetraol (compound 82); acridine-1,2,6,7-tetraol (compound 83); phenoxazine-2,3,7,8,10-pentaol (compound 84); dibenzo[c,f][2,7]napthyridine-2,3,10,11-tetraol (compound 85); and 6-methyl-5,6,6a,7-tetrahydro-4H-dibenzo[de,g]quinoline-2,10,11-triol (compound 86);

(3) the methylenedioxy analogs and pharmaceutically acceptable esters of compounds of (1) and (2); and (4) the pharmaceutically acceptable salts of the compounds of (1) to (3).

In a second aspect, this invention is pharmaceutical compositions comprising a compound of the first aspect of this invention and a pharmaceutically acceptable excipient; and pharmaceutical compositions comprising a pharmaceutically acceptable excipient and, as the sole active ingredient, a compound of the first aspect of the invention.

In a third aspect, this invention is a method of treating an amyloid disease in a mammal, especially a human, by administration of a therapeutically effective amount of a compound of the first aspect of this invention, for example as a pharmaceutical composition.

In a fourth aspect, this invention is the use of a compound of the first aspect of this invention in the manufacture of a medicament for the treatment of an amyloid disease.

In a fifth aspect, this invention is a method of preparation of the bis- and tris(dihydroxyaryl) compounds of the first aspect of this invention, i.e. the compounds of the formula or list above, except compound #86, and of their pharmaceutically acceptable esters, by deprotection of the methylenedioxy analogs of the compounds, optionally followed by the esterification of the resulting bis- and tris(dihydroxyaryl) compounds and/or the formation of pharmaceutically acceptable salts thereof.

In a sixth aspect, this invention is a method of treatment of Aβ, IAPP, other amyloids, and α-synuclein or NAC fibrillogenesis, in an in vitro environment. The method includes the step of administering into the in vitro environment a therapeutically effective amount of a compound of this invention. Preferably the compound is selected from the groups described below with respect to their activity against Aβ, IAPP, and NAC.

DETAILED DESCRIPTION OF THE INVENTION

Definitions

In this application, the following terms shall have the following meanings, without regard to whether the terms are used variantly elsewhere in the literature or otherwise in the known art.

The compounds of the invention, i.e. the compounds of the formula shown in the paragraph numbered (1) at the top of page 7 of the application and the compounds on the list immediately following and numbered (2), are referred to generally as bis- and tris-dihydroxyaryl compounds, or sometimes just as "dihydroxyaryl compounds". It will be noted that compound #84 has an additional hydroxy group, but does have two dihydroxyaryl groups; while compound #86 has only one dihydroxyaryl group but has an additional phenolic hydroxyl moiety.

"Methylenedioxy analogs" refers to the compounds of this invention in which each of the pairs of adjacent hydroxyl moieties of the dihydroxyaryl groups have been replaced by methylenedioxy groups. The methylenedioxy compounds are illustrated and referred to as compounds #1B to #86B or DC-0001B to DC-0086B. The methylenedioxy groups also are convenient intermediate protecting groups for the dihydroxy moieties and therefore these disclosed compounds are believed to also serve as effective prodrugs. The methylenedioxy analogs #1B to #80B are illustrated in Example 30.

"Pharmaceutically acceptable esters" refers to the compounds of this invention where the hydroxyl moieties of the dihydroxyaryl groups of the compounds are esterified with an acid or acids that result in a pharmaceutically acceptable poly(ester). The compounds are shown in Example 31 as acetylated, and these acetylated compounds are illustrated and referred to as compounds #1C to #86C or DC-0001C to DC-0086C; but it should be understood that the depiction of acetyl esters in Example 31 is merely illustrative, and all pharmaceutically acceptable esters are included within this invention. The ester groups are expected to serve as intermediate protecting groups for the hydroxyl moieties and therefore the pharmaceutically acceptable esters are expected to serve as effective prodrugs for their underlying bis- and tris-dihydroxyaryl compounds.

Chemical structures for each of the compounds of this invention (with the note that the acetates are shown as representative of the pharmaceutically acceptable esters as a class) are shown. The names of the compounds are variously IUPAC names [names derived according to the accepted IUPAC (International Union of Pure and Applied Chemistry) system established by the coalition of the Commission on Nomenclature of Organic Chemistry and the Commission on Physical Organic Chemistry, as can be found at http://www.chem.qmul.ac.uk/iupac], names derived from IUPAC names by addition or substitution (for example, by the use of "3,4-methylenedioxyphenyl" derived from "phenyl" instead of "benzo[1,3]dioxol-5-yl"), and names derived from the names of reactants (for example, by the use of "3,4-dihydroxybenzoic acid 3,4-dihydroxyanilide" instead of "N-(3,4-dihydroxy-phenyl)-3,4-dihydroxybenzamide"). However, the names used are explicitly equated to chemical structures, and are believed to be readily understood by a person of ordinary skill in the art.

"Mammal" includes both humans and non-human mammals, such as companion animals (cats, dogs, and the like), laboratory animals (such as mice, rats, guinea pigs, and the like) and farm animals (cattle, horses, sheep, goats, swine, and the like).

"Pharmaceutically acceptable excipient" means an excipient that is conventionally useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

"Pharmaceutically acceptable salt" means a salt that is pharmaceutically acceptable and have the desired pharmacological properties. Such salts include salts that may be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g. ethanolamine, diethanolamine, triethanolamine, tromethamine, N-methylglucamine, and the like. Such salts also include acid addition salts formed with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). When there are two acidic groups present, a pharmaceutically acceptable salt may be a mono-acid-mono-salt or a di-salt; and similarly where there are more than two acidic groups present, some or all of such groups can be salified.

A "therapeutically effective amount" in general means the amount that, when administered to a subject or animal for treating a disease, is sufficient to affect the desired degree of treatment for the disease. A "therapeutically effective amount" or a "therapeutically effective dosage" preferably inhibits, reduces, disrupts, disassembles amyloid or synuclein fibril formation, deposition, accumulation and/or persistence, or treats a disease associated with these conditions, such as an amyloid disease or a synucleinopathy, by at least 20%, more preferably by at least 40%, even more preferably by at least 60%, and still more preferably by at least 80%, relative to an untreated subject. Effective amounts of a compound of this invention or composition thereof for treatment of a mammalian subject are about 0.1 to about 1000 mg/Kg of body weight of the subject/day, such as from about 1 to about 100 mg/Kg/day, especially from about 10 to about 100 mg/Kg/day. A broad range of disclosed composition dosages are believed to be both safe and effective.

"Treating" or "treatment" of a disease includes preventing the disease from occurring in a mammal that may be predisposed to the disease but does not yet experience or exhibit symptoms of the disease (prophylactic treatment), inhibiting the disease (slowing or arresting its development), providing relief from the symptoms or side-effects of the disease (including palliative treatment), and relieving the disease (causing regression of the disease), such as by disruption of pre-formed amyloid or synuclein fibrils. One such preventive treatment may be use of the disclosed compounds for the treatment of Mild Cognitive impairment (MCI).

"NAC" (non-Aβ component) is a 35-amino acid peptide fragment of α-synuclein, which like α-synuclein, has the ability to form amyloid-like fibrils when incubated at 37° C., and is positive with amyloid stains such as Congo red (demonstrating a red/green birefringence when viewed under polarized light) and Thioflavin S (demonstrating positive fluorescence) (Hashimoto et al., *Brain Res.* 799:301-306, 1998; Ueda et al., *Proc. Natl. Acad. Sci. U.S.A.* 90:11282-11286, 1993). Inhibition of NAC fibril formation, deposition, accumulation, aggregation, and/or persistence is believed to be effective treatment for a number of diseases involving α-synuclein, such as Parkinson's disease, Lewy body disease and multiple system atrophy.

"Fibrillogenesis" refers to the formation, deposition, accumulation and/or persistence of amyloid fibrils, filaments, inclusions, deposits, as well as synuclein (usually involving α-synuclein) and/or NAC fibrils, filaments, inclusions, deposits or the like.

"Inhibition of fibrillogenesis" refers to the inhibition of formation, deposition, accumulation and/or persistence of such amyloid fibrils or synuclein fibril-like deposits.

"Disruption of fibrils or fibrillogenesis" refers to the disruption of pre-formed amyloid or synuclein fibrils, that usually exist in a pre-dominant β-pleated sheet secondary structure. Such disruption by compounds of the invention may involve marked reduction or disassembly of amyloid or synuclein fibrils as assessed by various methods such as circular dichroism spectroscopy, Thioflavin T fluorometry, Congo red binding, SDS-PAGE/Western blotting, as demonstrated by the Examples presented in this application.

"A pharmaceutical agent" or "pharmacological agent" or "pharmaceutical composition" refers to a compound or combination of compounds used for treatment, preferably in a pure or near pure form. In the specification, pharmaceutical or pharmacological agents include the compounds of this invention. The compounds are desirably purified to 80% homogeneity, and preferably to 90% homogeneity. Compounds and compositions purified to 99.9% homogeneity are believed to be advantageous. As a test or confirmation, a suitable homogeneous compound on HPLC would yield, what those skilled in the art would identify as a single sharp-peak band.

Compounds of the Invention

The compounds of this invention are:

compound of the formula: (1)

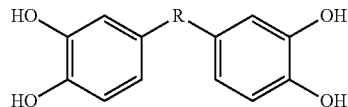

where:
R is a $C_1$-$C_{10}$ alkylene group, in which, when the number of carbon atoms is at least 2, there are optionally 1 or 2 non-adjacent double bonds; 1 to 3 non-adjacent methylene groups are optionally replaced by NR' (where R' is H, alkyl, or acyl), O, or S; and 1 or 2 methylene groups are optionally replaced by a carbonyl or hydroxymethylene group; and (2) the compounds that are:
3,4,3',4'-tetrahydroxybenzoin; 3,4,3',4'-tetrahydroxydesoxybenzoin; 3,4,3',4'-tetrahydroxydiphenylmethane; 1,2-bis(3,4-dihydroxyphenyl)ethane; 1,3-bis(3,4-dihydroxyphenyl)propane; 3,4,3',4'-tetrahydroxychalcone; 3,5-bis(3,4-dihydroxyphenyl)-1-methyl-2-pyrazoline; 4,6-bis(3,4-dihydroxyphenyl)-3-cyano-2-methylpyridine; 1,4-bis(3,4-dihydroxybenzyl)piperazine; N,N'-bis(3,4-dihydroxybenzyl)-N,N'-dimethyl-ethylenediamine; 2,5-bis(3,4-dihydroxybenzyl)-2,5-diaza[2.2.1]bicycloheptane; N,N'-bis(3,4-dihydroxy-benzyl)-trans-1,2-diaminocyclohexane; N,N'-bis(3,4-dihydroxybenzyl)-trans-1,4-diaminocyclohexane; N,N'-bis(3,4-dihydroxybenzyl)-cis-1,3-bis(aminomethyl)cyclohexane; N-(3,4-dihydroxybenzyl)proline 3,4-dihydroxybenzylamide; 2-(3,4-dihydroxybenzyl)isoquinoline-3-carboxylic acid 3,4-dihydroxy-phenethylamide; 2,6-bis(3,4-dihydroxybenzyl)cyclohexanone; 3,5-bis(3,4-dihydroxybenzyl)-1-methyl-4-piperidinone; 2,4-bis(3,4-dihydroxybenzyl)-3-tropinone; tris(3,4-dihydroxybenzyl)methane; α-(3,4-dihydroxybenzamido)-3,4-dihydroxycinnamic acid 3,4-dihydroxybenzyl amide; 4-(3,4-dihydroxybenzylaminomethylene)-2-(3,4-dihydroxyphenyl)oxazolin-5-one; 1,4-bis(3,4-dihydroxybenzoyl)piperazine; N,N'-bis(3,4-dihydroxybenzoyl)-N,N'-dimethylethylenediamine; 2,5-bis(3,4-dihydroxybenzoyl)-2,5-diaza[2.2.1]bicycloheptane; N,N'-bis(3,4-dihydroxybenzoyl)-trans-1,2-diaminocyclohexane; N,N'-bis(3,4-dihydroxybenzoyl)-cis-1,3-bis(aminomethyl)cyclohexane; 3,6-bis(3,4-dihydroxybenzyl)-2,5-diketopiperazine; 3,6-bis(3,4-dihydroxybenzylidene)-1,4-dimethyl-2,5-diketopiperazine; N-(3,4-dihydroxyphenylacetyl)proline-3,4-dihydroxyanilide; 2,3-bis(3,4-dihydroxyphenyl)butane; 1,3-bis(3,4-dihydroxybenzyl)benzene; 1,4-bis(3,4-dihydroxybenzyl)benzene; 2,6-bis(3,4-dihydroxybenzyl)-pyridine; 2,5-bis(3,4-dihydroxybenzyl)thiophene; 2,3-bis(3,4-dihydroxybenzyl)thiophene; 1,2-bis(3,4-dihydroxyphenyl)cyclohexane; 1,4-bis(3,4-dihydroxyphenyl)cyclohexane; 3,7-bis(3,4-dihydroxy-phenyl)bicyclo[3.3.0]octane; 2,3-bis(3,4-dihydroxyphenyl)-1,7,7-trimethyl-bicyclo[2.2.1]heptane; 1,2-bis(3,4-dihydroxyphenoxy)ethane; 1,3-bis(3,4-dihydroxyphenoxy)propane; trans-1,2-bis(3,4-dihydroxyphenoxy)cyclopentane; N-(3,4-dihydroxybenzyl)-3-(3,4-dihydroxyphenoxy)-2-hydroxypropylamine; 3,4-dihydroxyphenoxyacetic acid 3,4-dihydroxyanilide; 3,4-dihydroxyphenoxyacetic acid 3,4-dihydroxy-benzylamide; 3,4-dihydroxyphenoxyacetic acid 3,4-dihydroxyphenethylamide; 3,4-dihydroxybenzoic acid p-(3,4-dihydroxyphenoxy)anilide; 3,4-dihydroxybenzoic acid o-(3,4-dihydroxyphenoxy)anilide; 2,6-bis(3,4-dihydroxyphenoxy)pyridine; 3,4-dihydroxybenzoic acid 3,4-dihydroxyanilide; 3,4-dihydroxy-benzoic acid 3,4-dihydroxybenzylamide; 3,4-dihydroxybenzoic acid 3,4-dihydroxyphenethylamide; 3,4-dihydroxyphenyl acetic acid 3,4-dihydroxyanilide; 3,4-dihydroxyphenylacetic acid 3,4-dihydroxybenzyl-amide; 3,4-dihydroxyphenylacetic acid 3,4-dihydroxyphenethylamide; 3-(3,4-dihydroxyphenyl)propionic acid 3,4-dihydroxyanilide; 3-(3,4-dihydroxyphenyl)propionic acid 3,4-dihydroxybenzylamide; 3-(3,4-dihydroxyphenyl)propionic acid 3,4-dihydroxyphenethylamide; 3,4-dihydroxycinnamic acid 3,4-dihydroxyanilide; 3,4-dihydroxycinnamic acid 3,4-dihydroxybenzylamide; 3,4-dihydroxycinnamic acid 3,4-dihydroxyphenethylamide; oxalic acid bis(3,4-dihydroxyanilide); oxalic acid bis(3,4-dihydroxybenzyl-amide); oxalic acid bis(3,4-dihydroxyphenethylamide); succinic acid bis(3,4-dihydroxyanilide); succinic acid bis(3,4-dihydroxybenzylamide); succinic acid bis(3,4-dihydroxyphenethylamide); maleic acid bis(3,4-dihydroxyanilide); maleic acid bis(3,4-dihydroxybenzylamide); fumaric acid bis(3,4-dihydroxyanilide); fumaric acid bis(3,4-dihydroxybenzylamide); bis(3,4-dihydroxybenzyl)amine; N-(3,4-dihydroxy-benzyl)-3,4-dihydroxyphenethylamine; tris(3,4-dihydroxybenzyl)amine; 1,3-bis(3,4-dihydroxyphenyl)urea; 1-(3,4-dihydroxyphenyl)-3-(3,4-dihydroxybenzyl)urea; 1-(3,4-dihydroxyphenyl)-3-(3,4-dihydroxy-phenethyl)urea; 3-deoxy-3-(3,4-dihydroxybenzyl)aminoepicatechin; 3-deoxy-3-(3,4-dihydroxyphenethyl)-aminoepicatechin; 2,3,6,7-tetrahydroxy-9,10-epoxy-9,10-dihydroacridine; 10-aminoanthracene-1,2,7,8-tetraol; acridine-1,2,6,7-tetraol; phenoxazine-2,3,7,8,10-pentaol; dibenzo[c,f][2,7]napthyridine-2,3,10,11-tetraol; and 6-methyl-5,6,6a,7-tetrahydro-4H-dibenzo[de,g]quinoline-2,10,11-triol;

(3) the methylenedioxy analogs and pharmaceutically acceptable esters of the compounds of (1) and (2); and (4) the pharmaceutically acceptable salts of the compounds of (1) to (3).

Within the compounds of this invention, a first group of compounds is the compounds selected from the group consisting of:

compound of the formula: (1)

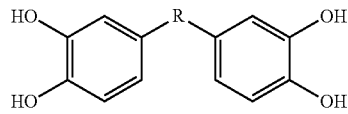

where:
R is a $C_1$-$C_{10}$, especially a $C_{1-6}$, alkylene group, in which, when the number of carbon atoms is at least 2, there are optionally 1 or 2 non-adjacent double bonds; 1 to 3 non-adjacent methylene groups are optionally replaced by NR' (where R' is H, $C_{1-3}$ alkyl, or $C_{2-4}$ acyl), O, or S, especially NH or N—$CH_3$; and 1 or 2 methylene groups are optionally replaced by a carbonyl or hydroxymethylene group;

(2) the methylenedioxy analogs and pharmaceutically acceptable tetraesters thereof; and (3) the pharmaceutically acceptable salts of the compounds of (1) and (2).

Within this first group, a subgroup of compounds is the group of compounds selected from the group consisting of:

compound of the formula: (1)

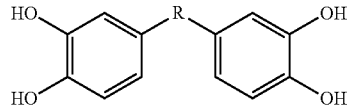

where:
R is a $C_2$-$C_{10}$, especially a $C_{2-6}$, alkylene group, in which there is optionally 1 double bond; and 1 or 2 non-adjacent ethylene groups are replaced by —C(O)NR'— or —NR'C(O)— (where R' is H or lower alkyl);

(2) the methylenedioxy analogs and pharmaceutically acceptable tetraesters thereof; and (3) the pharmaceutically acceptable salts of compounds of (1) and (2).

Within the compounds of this invention, a second group of compounds is:

(1) the compounds that are:
3,4,3',4'-tetrahydroxybenzoin; 3,4,3',4'-tetrahydroxydesoxybenzoin; 3,4,3',4'-tetrahydroxydiphenylmethane; 1,2-bis(3,4-dihydroxyphenyl)ethane; 1,3-bis(3,4-dihydroxyphenyl)propane; 3,4,3',4'-tetrahydroxychalcone; 3,5-bis(3,4-dihydroxyphenyl)-1-methyl-2-pyrazoline; 4,6-bis(3,4-dihydroxyphenyl)-3-cyano-2-methylpyridine; 1,4-bis(3,4-dihydroxybenzyl)piperazine; N,N'-bis(3,4-dihydroxybenzyl)-N,N'-dimethyl-ethylenediamine; 2,5-bis(3,4-dihydroxybenzyl)-2,5-diaza[2.2.1]bicycloheptane; N,N'-bis(3,4-dihydroxy-benzyl)-trans-1,2-diaminocyclohexane; N,N'-bis(3,4-dihydroxybenzyl)-trans-1,4-diaminocyclohexane; N,N'-bis(3,4-dihydroxybenzyl)-cis-1,3-bis(aminomethyl)cyclohexane; N-(3,4-dihydroxybenzyl)proline 3,4-dihydroxybenzylamide; 2-(3,4-dihydroxybenzyl)isoquinoline-3-carboxylic acid 3,4-dihydroxy-phenethylamide; 2,6-bis(3,4-dihydroxybenzyl)cyclohexanone; 3,5-bis(3,4-dihydroxybenzyl)-1-methyl-4-piperidinone; 2,4-bis(3,4-dihydroxybenzyl)-3-tropinone; tris(3,4-dihydroxybenzyl)methane; α-(3,4-dihydroxybenzamido)-3,4-dihydroxycinnamic acid 3,4-dihydroxybenzyl amide; 4-(3,4-dihydroxybenzylaminomethylene)-2-(3,4-dihydroxyphenyl)oxazolin-5-one; 1,4-bis(3,4-dihydroxybenzoyl)piperazine; N,N'-bis(3,4-dihydroxybenzoyl)-N,N'-dimethylethylenediamine; 2,5-bis(3,4-dihydroxybenzoyl)-2,5-diaza[2.2.1]bicycloheptane; N,N'-bis(3,4-dihydroxybenzoyl)-trans-1,2-diaminocyclohexane; N,N'-bis(3,4-dihydroxybenzoyl)-cis-1,3-bis(aminomethyl)cyclohexane; 3,6-bis(3,4-dihydroxybenzyl)-2,5-diketopiperazine; 3,6-bis(3,4-dihydroxybenzylidene)-1,4-dimethyl-2,5-diketopiperazine; N-(3,4-dihydroxyphenylacetyl)proline-3,4-dihydroxyanilide; 2,3-bis(3,4-dihydroxyphenyl)butane; 1,3-bis(3,4-dihydroxybenzyl)benzene; 1,4-bis(3,4-dihydroxybenzyl)benzene; 2,6-bis(3,4-dihydroxybenzyl)-pyridine; 2,5-bis(3,4-dihydroxybenzyl)thiophene; 2,3-bis(3,4-dihydroxybenzyl)thiophene; 1,2-bis(3,4-dihydroxyphenyl)cyclohexane; 1,4-bis(3,4-dihydroxyphenyl)cyclohexane; 3,7-bis(3,4-dihydroxy-phenyl)bicyclo[3.3.0]octane; 2,3-bis(3,4-dihydroxyphenyl)-1,7,7-trimethyl-bicyclo[2.2.1]heptane; 1,2-bis(3,4-dihydroxyphenoxy)ethane; 1,3-bis(3,4-dihydroxyphenoxy)propane; trans-1,2-bis(3,4-dihydroxyphenoxy)cyclopentane; N-(3,4-dihydroxybenzyl)-3-(3,4-dihydroxyphenoxy)-2-hydroxypropylamine; 3,4-dihydroxyphenoxyacetic acid 3,4-dihydroxyanilide; 3,4-dihydroxyphenoxyacetic acid 3,4-dihydroxy-benzylamide; 3,4-dihydroxyphenoxyacetic acid 3,4-dihydroxyphenethylamide; 3,4-dihydroxybenzoic acid p-(3,4-dihydroxyphenoxy)anilide; 3,4-dihydroxybenzoic acid o-(3,4-dihydroxyphenoxy)anilide; 2,6-bis(3,4-dihydroxyphenoxy)pyridine; 3,4-dihydroxybenzoic acid 3,4-dihydroxyanilide; 3,4-dihydroxy-benzoic acid 3,4-dihydroxybenzylamide; 3,4-dihydroxybenzoic acid 3,4-dihydroxyphenethylamide; 3,4-dihydroxyphenyl acetic acid 3,4-dihydroxyanilide; 3,4-dihydroxyphenylacetic acid 3,4-dihydroxybenzyl-amide; 3,4-dihydroxyphenylacetic acid 3,4-dihydroxyphenethylamide; 3-(3,4-dihydroxyphenyl)propionic acid 3,4-dihydroxyanilide; 3-(3,4-dihydroxyphenyl)propionic acid 3,4-dihydroxybenzylamide; 3-(3,4-dihydroxyphenyl)propionic acid 3,4-dihydroxyphenethylamide; 3,4-dihydroxycinnamic acid 3,4-dihydroxyanilide; 3,4-dihydroxycinnamic acid 3,4-dihydroxybenzylamide; 3,4-dihydroxycinnamic acid 3,4-dihydroxyphenethylamide; oxalic acid bis(3,4-dihydroxyanilide); oxalic acid bis(3,4-dihydroxybenzyl-amide); oxalic acid bis(3,4-dihydroxyphenethylamide); succinic acid bis(3,4-dihydroxyanilide); succinic acid bis(3,4-dihydroxybenzylamide); succinic acid bis(3,4-dihydroxyphenethylamide); maleic acid bis(3,4-dihydroxyanilide); maleic acid bis(3,4-dihydroxybenzylamide); fumaric acid bis(3,4-dihydroxyanilide); fumaric acid bis(3,4-dihydroxybenzylamide); bis(3,4-dihydroxybenzyl)amine; N-(3,4-dihydroxy-benzyl)-3,4-dihydroxyphenethylamine; tris(3,4-dihydroxybenzyl)amine; 1,3-bis(3,4-dihydroxyphenyl)urea; 1-(3,4-dihydroxyphenyl)-3-(3,4-dihydroxybenzyl)urea; 1-(3,4-dihydroxyphenyl)-3-(3,4-dihydroxy-phenethyl)urea; 3-deoxy-3-(3,4-dihydroxybenzyl)aminoepicatechin; 3-deoxy-3-(3,4-dihydroxyphenethyl)-aminoepicatechin; 2,3,6,7-tetrahydroxy-9,10-epoxy-9,10-dihydroacridine; 10-aminoanthracene-1,2,7,8-tetraol; acridine-1,2,6,7-tetraol; phenoxazine-2,3,7,8,10-pentaol; dibenzo[c,f][2,7]napthyridine-2,3,10,11-tetraol; and 6-methyl-5,6,6a,7-tetrahydro-4H-dibenzo[de,g]quinoline-2,10,11-triol;

(2) the methylenedioxy analogs and pharmaceutically acceptable esters thereof; and (3) the pharmaceutically acceptable salts of the compounds of (1) and (2).

Within this second group, a subgroup of compounds is:

(1) the compounds that are:
3,4,3',4'-tetrahydroxybenzoin; 3,4,3',4'-tetrahydroxydesoxybenzoin; 3,4,3',4'-tetrahydroxydiphenylmethane; 1,2-bis(3,4-dihydroxyphenyl)ethane; 1,3-bis(3,4-dihydroxyphenyl)propane; 3,4,3',4'-tetrahydroxychalcone; 3,5-bis(3,4-dihydroxyphenyl)-1-methyl-2-pyrazoline; 4,6-bis(3,4-dihydroxyphenyl)-3-cyano-2-methylpyridine; 1,4-bis(3,4-dihydroxybenzyl)piperazine; N,N'-bis(3,4-dihydroxybenzyl)-N,N'-dimethyl-ethylenediamine; 2,5-bis(3,4-dihydroxybenzyl)-2,5-diaza[2.2.1]bicycloheptane; N,N'-bis(3,4-dihydroxy-benzyl)-trans-1,2-diaminocyclohexane; N,N'-bis(3,4-dihydroxybenzyl)-trans-1,4-diaminocyclohexane; N,N'-bis(3,4-dihydroxybenzyl)-cis-1,3-bis(aminomethyl)cyclohexane; N-(3,4-dihydroxybenzyl) proline 3,4-dihydroxybenzylamide; 2-(3,4-dihydroxybenzyl)isoquinoline-3-carboxylic acid 3,4-dihydroxy-phenethylamide; 2,6-bis(3,4-dihydroxybenzyl)cyclohexanone; 3,5-bis(3,4-dihydroxybenzyl)-1-methyl-4-piperidinone; 2,4-bis(3,4-dihydroxybenzyl)-3-tropinone; tris(3,4-dihydroxybenzyl)methane; α-(3,4-dihydroxybenzamido)-3,4-dihydroxycinnamic acid 3,4-dihydroxybenzyl amide; 4-(3,4-dihydroxybenzylaminomethylene)-2-(3,4-dihydroxyphenyl)oxazolin-5-one; 1,4-bis(3,4-dihydroxybenzoyhpiperazine; N,N'-bis(3,4-dihydroxybenzoyl)-N,N'-dimethylethylenediamine; 2,5-bis(3,4-dihydroxybenzoyl)-2,5-diaza[2.2.1]bicycloheptane; N,N'-bis(3,4-dihydroxybenzoyl)-trans-1,2-diaminocyclohexane; N,N'-bis(3,4-dihydroxybenzoyl)-cis-1,3-bis(aminomethyl)cyclohexane; 3,6-bis(3,4-dihydroxybenzyl)-2,5-diketopiperazine; 3,6-bis(3,4-dihydroxybenzylidene)-1,4-dimethyl-2,5-diketopiperazine; N-(3,4-dihydroxyphenylacetyl)proline-3,4-dihydroxyanilide; 2,3-bis(3,4-dihydroxyphenyl)butane; 1,3-bis(3,4-dihydroxybenzyl)benzene; 1,4-bis(3,4-dihydroxybenzyl)benzene; 2,6-bis(3,4-dihydroxybenzyl)-pyridine; 2,5-bis(3,4-dihydroxybenzyl)thiophene; 2,3-bis(3,4-dihydroxybenzyl)thiophene; 1,2-bis(3,4-dihydroxyphenyl)cyclohexane; 1,4-bis(3,4-dihydroxyphenyl)cyclohexane; 3,7-bis(3,4-dihydroxy-phenyl)bicyclo[3.3.0]octane; 2,3-bis(3,4-dihydroxyphenyl)-1,7,7-trimethyl-bicyclo[2.2.1]heptane; 1,2-bis(3,4-dihydroxyphenoxy)ethane; 1,3-bis(3,4-dihydroxyphenoxy)propane; trans-1,2-bis(3,4-dihydroxyphenoxy)cyclopentane; N-(3,4-dihydroxybenzyl)-3-(3,4-dihydroxyphenoxy)-2-hydroxypropylamine; 3,4-dihydroxyphenoxyacetic acid 3,4-dihydroxyanilid; 3,4-dihydroxyphenoxyacetic acid 3,4-dihydroxy-benzylamide; 3,4-dihydroxyphenoxyacetic acid 3,4-dihydroxyphenethylamide; 3,4-dihydroxybenzoic acid p-(3,4-dihydroxyphenoxy)anilide; 3,4-dihydroxybenzoic acid o-(3,4-dihydroxyphenoxy)anilide; 2,6-bis(3,4-dihydroxyphenoxy)pyridine; 3,4-dihydroxybenzoic acid 3,4-dihydroxyanilide; 3,4-dihydroxy-benzoic acid 3,4-dihydroxybenzylamide; 3,4-dihydroxybenzoic acid 3,4-dihydroxyphenethylamide; 3,4-dihydroxyphenyl acetic acid 3,4-dihydroxyanilide; 3,4-dihydroxyphenylacetic acid 3,4-dihydroxybenzyl-amide; 3,4-dihydroxyphenylacetic acid 3,4-dihydroxyphenethylamide; 3-(3,4-dihydroxyphenyl)propionic acid 3,4-dihydroxyanilide; 3-(3,4-dihydroxyphenyl)propionic acid 3,4-dihydroxybenzylamide; 3-(3,4-dihydroxyphenyl)propionic acid 3,4-dihydroxyphenethylamide; 3,4-dihydroxycinnamic acid 3,4-dihydroxyanilide; 3,4-dihydroxycinnamic acid 3,4-dihydroxybenzylamide; 3,4-dihydroxycinnamic acid 3,4-dihydroxyphenethylamide; oxalic acid bis(3,4-dihydroxyanilide); oxalic acid bis(3,4-dihydroxybenzyl-amide); oxalic acid bis(3,4-dihydroxyphenethylamide); succinic acid bis(3,4-dihydroxyanilide); succinic acid bis(3,4-dihydroxybenzylamide); succinic acid bis(3,4-dihydroxyphenethylamide); maleic acid bis(3,4-dihydroxyanilide); maleic acid bis(3,4-dihydroxybenzylamide); fumaric acid bis(3,4-dihydroxyanilide); fumaric acid bis(3,4-dihydroxybenzylamide); bis(3,4-dihydroxybenzyl)amine; N-(3,4-dihydroxy-benzyl)-3,4-dihydroxyphenethylamine; tris(3,4-dihydroxybenzyl)amine; 1,3-bis(3,4-dihydroxyphenyl)urea; 1-(3,4-dihydroxyphenyl)-3-(3,4-dihydroxybenzyl)urea; 1-(3,4-dihydroxyphenyl)-3-(3,4-dihydroxy-phenethyl)urea; 3-deoxy-3-(3,4-dihydroxybenzyl)aminoepicatechin; and 3-deoxy-3-(3,4-dihydroxy-phenethyl)aminoepicatechin;

(2) the methylenedioxy analogs and pharmaceutically acceptable esters thereof; and (3) the pharmaceutically acceptable salts of the compounds of (1) and (2).

Within this subgroup, a further subgroup is:

(1) the compounds that are:
3,4,3',4'-tetrahydroxybenzoin; 3,4,3',4'-tetrahydroxydiphenylmethane; 1,2-bis(3,4-dihydroxyphenyl)ethane; 4,6-bis(3,4-dihydroxyphenyl)-3-cyano-2-methylpyridine; 1,4-bis(3,4-dihydroxybenzyl)piperazine; N,N'-bis(3,4-dihydroxybenzyl)-trans-1,2-diaminocyclohexane; 2,4-bis(3,4-dihydroxybenzyl)-3-tropinone; α-(3,4-dihydroxybenzamido)-3,4-dihydroxycinnamic acid 3,4-dihydroxybenzyl amide; 1,4-bis(3,4-dihydroxybenzoyl)piperazine; N,N'-bis(3,4-dihydroxybenzoyl)-trans-1,2-diaminocyclohexane; 3,4-dihydroxybenzoic acid 3,4-dihydroxyanilide; 3,4-dihydroxybenzoic acid 3,4-dihydroxybenzylamide; 3-(3,4-dihydroxyphenyl)propionic acid 3,4-dihydroxyanilide; 3-(3,4-dihydroxyphenyl)propionic acid 3,4-dihydroxybenzylamide; 3,4-dihydroxycinnamic acid 3,4-dihydroxybenzylamide; oxalic acid bis(3,4-dihydroxyanilide); succinic acid bis(3,4-dihydroxyanilide); succinic acid bis(3,4-dihydroxy-benzylamide); bis(3,4-dihydroxybenzyl)amine; tris(3,4-dihydroxybenzyl)amine; 1,3-bis(3,4-dihydroxy-phenyl)urea; and 1-(3,4-dihydroxyphenyl)-3-(3,4-dihydroxyphenethyl)urea;

(2) the methylenedioxy analogs and pharmaceutically acceptable esters thereof; and (3) the pharmaceutically acceptable salts of the compounds of (1) and (2).

Within each of these groups and subgroups, there are especially the compounds of the invention that are the bis- and tris(dihydroxyaryl) compounds (i.e. the compounds of the formula or of the list) and compound #86, and their pharmaceutically acceptable salts.

Synthesis of the Compounds of the Invention

The compounds of this invention may be prepared by methods generally known to the person of ordinary skill in the art, having regard to that knowledge and the disclosure of this application including Examples 1-24.

The starting materials and reagents used in preparing these compounds are either available from commercial suppliers such as the Aldrich Chemical Company (Milwaukee, Wis.), Bachem (Torrance, Calif.), Sigma (St. Louis, Mo.), or Lancaster Synthesis Inc. (Windham, N.H.) or are prepared by methods well known to a person of ordinary skill in the art, following procedures described in such references as Fieser and Fieser's *Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; Organic Reactions, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

In most cases, protective groups for the hydroxy groups are introduced and finally removed. Suitable protective groups are described in Greene et al., *Protective Groups in Organic Synthesis*, Second Edition, John Wiley and Sons, New York, 1991. A preferred protective group is the methylenedioxy group, as seen in many of Examples 1-23, and a wide variety of methylenedioxyphenyl compounds (such as 3,4-methylenedioxyacetophenone, 3,4-methylenedioxyaniline, 3,4-methylenedioxybenzaldehyde, 3,4-methylenedioxybenzoic acid, 3,4-methylenedioxybenzonitrile, 3,4-methylenedioxybenzoic acid, 3,4-methylenedioxybenzoyl chloride, 3,4-methylenedioxycinnamic acid, 3,4-methylenedioxynitrobenzene, 3,4-methylenedioxyphenol, 3,4-methylenedioxyphenylacetic acid, 3,4-methylenedioxyphenylacetonitrile, 3,4-methylenedioxyphenyl isocyanate, 3,4-methylenedioxyphenylmagnesium bromide, and 3,4-methylenedioxyphenylmethanol) are commercially available. Other protecting groups, such as the benzyl and methoxymethyl groups, may also be used.

Other starting materials or early intermediates may be prepared by elaboration of the materials listed above, for example, by methods well known to a person of ordinary skill in the art.

The starting materials, intermediates, and compounds of this invention may be isolated and purified using conventional techniques, including precipitation, filtration, distillation, crystallization, chromatography, and the like. The compounds may be characterized using conventional methods, including physical constants and spectroscopic methods.

Pharmacology and Utility

The compounds of this invention, either as the dihydroxyaryl compounds per se, or as the methylenedioxy analogs or pharmaceutically acceptable esters (once de-protected either in the body or in vitro), act to inhibit or prevent amyloid fibril formation, inhibit or prevent amyloid fibril growth, and/or cause disassembly, disruption, and/or disaggregation of pre-formed amyloid fibrils and amyloid protein deposits. Their activity can be measured in vitro by methods such as those discussed in Examples 25-27, while their activity in vivo against amyloid diseases can be measured in animal models, such as those APP transgenic mouse models that mimic many of the neuropathological hallmarks of Alzheimer's disease, and in humans.

"Amyloid diseases" or "amyloidoses" suitable for treatment with the compounds of this invention are diseases associated with the formation, deposition, accumulation, or persistence of amyloid fibrils, especially the fibrils of an amyloid protein selected from the group consisting of Aβ amyloid, AA amyloid, AL amyloid, IAPP amyloid, PrP amyloid, $\alpha_2$-microglobulin amyloid, transthyretin, prealbumin, and procalcitonin, especially Aβ amyloid and IAPP amyloid. Suitable such diseases include Alzheimer's disease, Down's syndrome, dementia pugilistica, multiple system atrophy, inclusion body myositis, hereditary cerebral hemorrhage with amyloidosis of the Dutch type, Nieman-Pick disease type C, cerebral β-amyloid angiopathy, dementia associated with cortical basal degeneration, the amyloidosis of type 2 diabetes, the amyloidosis of chronic inflammation, the amyloidosis of malignancy and Familial Mediterranean Fever, the amyloidosis of multiple myeloma and B-cell dyscrasias, the amyloidosis of the prion diseases, Creutzfeldt-Jakob disease, Gerstmann-Straussler syndrome, kuru, scrapie, the amyloidosis associated with carpal tunnel syndrome, senile cardiac amyloidosis, familial amyloidotic polyneuropathy, and the amyloidosis associated with endocrine tumors, especially Alzheimer's disease and type 2 diabetes.

The compounds also act to inhibit or prevent α-synuclein/NAC fibril formation, inhibit or prevent α-synuclein/NAC fibril growth, and/or cause disassembly, disruption, and/or disaggregation of preformed α-synuclein/NAC fibrils and α-synuclein/NAC-associated protein deposits. Their activity can be measured in vitro by methods similar to those discussed in Examples 24-26, or in vivo in animal models, such as those α-synuclein transgenic mouse models that mimic some of the neuropathological hallmarks of Parkinson's disease, and in humans.

"Synuclein diseases" or "synucleinopathies" suitable for treatment with the compounds of this invention are diseases associated with the formation, deposition, accumulation, or persistence of synuclein fibrils, especially α-synuclein fibrils. Suitable such diseases include Parkinson's disease, familial Parkinson's disease, Lewy body disease, the Lewy body variant of Alzheimer's disease, dementia with Lewy bodies, multiple system atrophy, and the Parkinsonism-dementia complex of Guam.

The therapeutic ratio of a compound can be determined, for example, by comparing the dose that gives effective anti-fibril (anti-amyloid or anti-α-synuclein/NAC) activity in a suitable in vivo model in a suitable animal species such as the mouse, with the dose that gives significant weight loss (or other observable side-effects) in the test animal species.

Compounds of special interest for treating the formation, deposition, accumulation, or persistence of Aβ amyloid fibrils, or for treating Alzheimer's disease, are selected from the group consisting of (1) the compounds that are:
3,4,3',4'-tetrahydroxybenzoin; 3,4,3',4'-tetrahydroxydiphenylmethane; 1,2-bis(3,4-dihydroxyphenyl)ethane; N,N'-bis(3,4-dihydroxybenzyl)-trans-1,2-diaminocyclohexane; α-(3,4-dihydroxybenzamido)-3,4-dihydroxycinnamic acid 3,4-dihydroxybenzylamide; 3,4-dihydroxybenzoic acid 3,4-dihydroxyanilide; bis(3,4-dihydroxybenzyl)amine; 1,3-bis(3,4-dihydroxyphenyl)urea; and 1-(3,4-dihydroxyphenyl)-3-(3,4-dihydroxyphenethyl)urea;

(2) the methylenedioxy analogs and pharmaceutically acceptable esters thereof; and (3) the pharmaceutically acceptable salts of the compounds of (1) and (2).

Especially of interest are the compounds of (1) above and their pharmaceutically acceptable salts.

Compounds of special interest for treating the formation, deposition, accumulation, or persistence of IAPP amyloid fibrils, or for treating type 2 diabetes, are selected from the group consisting of (1) the compounds that are:
3,4,3',4'-tetrahydroxybenzoin; 3,4,3',4'-tetrahydroxydiphenylmethane; 1,2-bis(3,4-dihydroxyphenyl)ethane; 2,4-bis(3,4-dihydroxybenzyl)-3-tropinone; 1,4-bis(3,4-dihydroxybenzoyl)piperazine; 3,4-dihydroxybenzoic acid 3,4-dihydroxyanilide; 3,4-dihydroxybenzoic acid 3,4-dihydroxybenzylamide; 3-(3,4-dihydroxyphenyl)propionic acid 3,4-dihydroxybenzylamide; oxalic acid bis(3,4-dihydroxyanilide); succinic acid bis(3,4-dihydroxyanilide); tris(3,4-dihydroxybenzyl)amine; and 1-(3,4-dihydroxyphenyl)-3-(3,4-dihydroxyphenethyl)urea;

(2) the methylenedioxy analogs and pharmaceutically acceptable esters thereof; and (3) the pharmaceutically acceptable salts of the compounds of (1) and (2).

Especially of interest are the compounds of (1) above and their pharmaceutically acceptable salts.

Compounds of special interest for treating the formation, deposition, accumulation, or persistence of α-synuclein fibrils, or for treating Parkinson's disease or other synucleinopathies, are selected from the group consisting of (1) the compounds that are:
3,4,3',4'-tetrahydroxybenzoin; 3,4,3',4'-tetrahydroxydiphenylmethane; 1,2-bis(3,4-dihydroxyphenyl)ethane; N,N'-bis(3,4-dihydroxybenzyl)-trans-1,2-diaminocyclohexane; N,N'-bis(3,4-dihydroxybenzoyl)-trans-1,2-diaminocyclohexane; 3,4-dihydroxybenzoic acid 3,4-dihydroxyanilide; 3,4-dihydroxybenzoic acid 3,4-dihydroxybenzylamide; succinic acid bis(3,4-dihydroxyanilide); bis(3,4-dihydroxybenzyl)amine; and 1-(3,4-dihydroxyphenyl)-3-(3,4-dihydroxyphenethyl)urea;

(2) the methylenedioxy analogs and pharmaceutically acceptable esters thereof; and (3) the pharmaceutically acceptable salts of the compounds of (1) and (2).

Especially of interest are the compounds of (1) above and their pharmaceutically acceptable salts.

Pharmaceutical Compositions and Administration

In general, compounds of the invention will be administered in therapeutically effective amounts by any of the usual modes known in the art, either singly or in combination with at least one other compound of this invention and/or at least one other conventional therapeutic agent for the disease being treated. A therapeutically effective amount may vary widely depending on the disease, its severity, the age and relative health of the animal being treated, the potency of the compound(s), and other factors. As anti-fibril agents, therapeutically effective amounts of compounds of this invention may range from 0.1-1000 mg/Kg body weight/day, such as from 1-100 mg/Kg/day; for example, 10-100 mg/Kg/day. A person of ordinary skill in the art will be conventionally able, and without undue experimentation, having regard to that skill and to this disclosure, to determine a therapeutically effective amount of a compound for the treatment of an amyloid disease such as an amyloidosis or α-synuclein/NAC fibril formation.

Preferred compositions will contain a compound of this invention that is at least substantially pure. In general "pure" means better than 95% pure, and "substantially pure" means a compound synthesized such that the compound, as made as available for consideration into a therapeutic dosage, has only those impurities that can not readily nor reasonably be removed by conventional purification processes.

In general, the compounds of this invention will be administered as pharmaceutical compositions by one of the following routes: oral, topical, systemic (e.g. transdermal, intranasal, or by suppository), or parenteral (e.g. intramuscular, subcutaneous, or intravenous injection). Compositions may take the form of tablets, pills, capsules, semisolids, powders, sustained release formulations, solutions, suspensions, elixirs, aerosols, or any other appropriate compositions; and comprise at least one compound of this invention in combination with at least one pharmaceutically acceptable excipient. Suitable excipients are well known to persons of ordinary skill in the art, and they, and the methods of formulating the compositions, may be found in such standard references as *Remington: The Science and Practice of Pharmacy*, A. Gennaro, ed., 20th edition, Lippincott, Williams & Wilkins, Philadelphia, Pa. Suitable liquid carriers, especially for injectable solutions, include water, aqueous saline solution, aqueous dextrose solution, and glycols.

In particular, the compound(s)—optimally only one such compound is administered in any particular dosage form—can be administered, orally, for example, as tablets, troches, lozenges, aqueous or oily suspension, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

Tablets contain the compound in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, maize starch or alginic acid; binding agents, for example, maize starch, gelatin or acacia, and lubricating agents, for example, magnesium stearate or stearic acid or talc. The tablets may be uncoated or they may be coated by known techniques to delay disintegration and absorption in the gastrointestinal tract and thereby provide a sustained action over a longer period. For example, a time delay material such as glycerol monostearate or glycerol distearate may be employed. Formulations for oral use may also be presented as hard gelatin capsules wherein the compound is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Aqueous suspensions contain the compound in admixture with excipients suitable for the manufacture of aqueous suspensions. Such excipients are suspending agents, for example, sodium carboxymethylcellulose, methylcellulose, hydroxypropylmethyl cellulose, sodium alginate, polyvinylpyrrolidone, gum tragacanth and gum acacia; dispersing or wetting agents may be naturally occurring phosphatides, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids such as hexitol such as polyoxyethylene sorbitol monooleate, or condensation products of ethylene oxide with partial esters from fatty acids and a hexitol anhydrides, for example, polyethylene sorbitan monooleate. The aqueous suspensions may also contain one or more preservatives, for example, ethyl or n-propyl p-hydroxybenzoate, one or more coloring agents, one or more flavoring agents, or one or more sweetening agents, such as sucrose or saccharin.

Oily suspensions may be formulated by suspending the compound in a vegetable oil, for example arachis oil, olive oil, sesame oil, or coconut oil or in a mineral oil such as liquid paraffin. The oily suspensions may contain a thickening agent, for example beeswax, hard paraffin or cetyl alcohol. Sweetening agents, such as those set forth below, and flavoring agents may be added to provide a palatable oral preparation. These compositions may be preserved by the addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already described above. Additional excipients, for example sweetening, flavoring and agents, may also be present.

The compounds of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally occurring phosphatides, for example soy bean, lecithin, and occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsion may also contain sweetening and flavoring agents. Syrups and elixirs may be formulated with sweetening agents, for example, glycerol, sorbitol or sucrose. Such formulations may also contain a demulcent, a preservative and flavoring and coloring agents.

Other oral delivery systems such as self-microemulsifying drug delivery systems (SMEDDS) in liquid and pellet forms that result in improved solubility, dissolution, and in vivo oral absorption of the poorly water-soluble compounds can be formulated such as those developed for curcumin. (European Journal of Pharmaceutics and Biopharmaceutics 76 (2010) 475-485).

The compounds of the invention can also be administered by injection or infusion, either subcutaneously or intravenously, or intramuscularly, or intrasternally, or intranasally, or by infusion techniques in the form of sterile injectable or oleaginous suspension. The compound may be in the form of a sterile injectable aqueous or oleaginous suspensions. These suspensions may be formulated according to the known art using suitable dispersing of wetting agents and suspending agents that have been described above. The sterile injectable preparation may also be a sterile injectable solution or suspension in a non-toxic parenterally-acceptable diluent or solvent for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oils may be conventionally employed including synthetic mono- or diglycerides. In addition fatty acids such as oleic acid find use in the preparation of injectables. Dosage regimens can be adjusted to provide the optimum therapeutic response. For example, several divided dosages may be administered daily or the dosage may be proportionally reduced as indicated by the exigencies of the therapeutic situation.

It is especially advantageous to formulate the compounds in dosage unit form for ease of administration and uniformity of dosage. Dosage unit form as used herein refers to physically discrete units suited as unitary dosages for the subjects to be treated; each containing a therapeutically effective quantity of the compound and at least one pharmaceutical excipient. A drug product will comprise a dosage unit form within a container that is labeled or accompanied by a label indicating the intended method of treatment, such as the treatment of an amyloid disease, for example an amyloidosis such as Alzheimer's disease or a disease associated with α-synuclein/NAC fibril formation such as Parkinson's disease.

Sustained Release Formulations

The invention also includes the use of sustained release formulations to deliver the compounds of the present invention to the desired target (i.e. brain or systemic organs) at high circulating levels (between $10^{-9}$ and $10^{-4}$ M) are also disclosed. In a preferred embodiment for the treatment of Alzheimer's or Parkinson's disease, the circulating levels of the compounds is maintained up to $10^{-7}$ M. The levels are either circulating in the patient systemically, or in a preferred embodiment, present in brain tissue, and in a most preferred embodiments, localized to the amyloid or α-synudein fibril deposits in brain or other tissues.

It is understood that the compound levels are maintained over a certain period of time as is desired and can be easily determined by one skilled in the art using this disclosure and compounds of the invention. In a preferred embodiment, the invention includes a unique feature of administration comprising a sustained release formulation so that a constant level of therapeutic compound is maintained between $10^{-8}$ and $10^{-6}$M between 48 to 96 hours in the sera.

Such sustained and/or timed release formulations may be made by sustained release means of delivery devices that are well known to those of ordinary skill in the art, such as those described in U.S. Pat. Nos. 3,845,770; 3,916,899; 3,536,809; 3,598,123; 4,008,719; 4,710,384; 5,674,533; 5,059,595; 5,591,767; 5,120,548; 5,073,543; 5,639,476; 5,354,556 and 5,733,566, the disclosures of which are each incorporated herein by reference. These pharmaceutical compositions can be used to provide slow or sustained release of one or more of the active compounds using, for example, hydroxypropylmethyl cellulose, other polymer matrices, gels, permeable membranes, osmotic systems, multilayer coatings, microparticles, liposomes, microspheres, or the like. Suitable sustained release formulations known to those skilled in the art, including those described herein, may be readily selected for use with the pharmaceutical compositions of the invention. Thus, single unit dosage forms suitable for oral administration, such as, but not limited to, tablets, capsules, gelcaps, caplets, powders and the like, that are adapted for sustained release are encompassed by the present invention.

In a preferred embodiment, the sustained release formulation contains active compound such as, but not limited to, microcrystalline cellulose, maltodextrin, ethylcellulose, and magnesium stearate. As described above, all known methods for encapsulation which are compatible with properties of the disclosed compounds are encompassed by this invention. The sustained release formulation is encapsulated by coating particles or granules of the pharmaceutical composition of the invention with varying thickness of slowly soluble polymers or by microencapsulation. In a preferred embodiment, the sustained release formulation is encapsulated with a coating material of varying thickness (e.g. about 1 micron to 200 microns) that allow the dissolution of the pharmaceutical composition about 48 hours to about 72 hours after administration to a mammal. In another embodiment, the coating material is a food-approved additive.

In another embodiment, the sustained release formulation is a matrix dissolution device that is prepared by compressing the drug with a slowly soluble polymer carrier into a tablet. In one preferred embodiment, the coated particles have a size range between about 0.1 to about 300 microns, as disclosed in U.S. Pat. Nos. 4,710,384 and 5,354,556, which are incorporated herein by reference in their entireties. Each of the particles is in the form of a micromatrix, with the active ingredient uniformly distributed throughout the polymer.

Sustained release formulations such as those described in U.S. Pat. No. 4,710,384, which is incorporated herein by reference in its entirety, having a relatively high percentage of plasticizer in the coating in order to permit sufficient flexibility to prevent substantial breakage during compression are disclosed. The specific amount of plasticizer varies depending on the nature of the coating and the particular plasticizer used. The amount may be readily determined empirically by testing the release characteristics of the tablets formed. If the medicament is released too quickly, then more plasticizer is used. Release characteristics are also a function of the thickness of the coating. When substantial amounts of plasticizer are used, the sustained release capacity of the coating diminishes. Thus, the thickness of the coating may be increased slightly to make up for an increase in the amount of plasticizer. Generally, the plasticizer in such an embodiment will be present in an amount of about 15 to 30% of the sustained release material in the coating, preferably 20 to 25%, and the amount of coating will be from 10 to 25% of the weight of the active material, preferably 15 to 20%. Any conventional pharmaceutically acceptable plasticizer may be incorporated into the coating.

The compounds of the invention can be formulated as a sustained and/or timed release formulation. All sustained release pharmaceutical products have a common goal of improving drug therapy over that achieved by their non-sustained counterparts. Ideally, the use of an optimally designed sustained release preparation in medical treatment is characterized by a minimum of drug substance being employed to cure or control the condition. Advantages of sustained release formulations may include: 1) extended activity of the composition, 2) reduced dosage frequency, and 3) increased patient compliance. In addition, sustained release formulations can be used to affect the time of onset of action or other characteristics, such as blood levels of the composition, and thus can affect the occurrence of side effects.

The sustained release formulations of the invention are designed to initially release an amount of the therapeutic composition that promptly produces the desired therapeutic effect, and gradually and continually release of other amounts of compositions to maintain this level of therapeutic effect over an extended period of time. In order to maintain this constant level in the body, the therapeutic composition must be released from the dosage form at a rate that will replace the composition being metabolized and excreted from the body.

The sustained release of an active ingredient may be stimulated by various inducers, for example pH, temperature, enzymes, water, or other physiological conditions or compounds. The term "sustained release component" in the context of the present invention is defined herein as a compound or compounds, including, but not limited to, polymers, polymer matrices, gels, permeable membranes, liposomes, microspheres, or the like, or a combination thereof, that facilitates the sustained release of the active ingredient.

If the complex is water-soluble, it may be formulated in an appropriate buffer, for example, phosphate buffered saline, or other physiologically compatible solutions. Alternatively, if the resulting complex has poor solubility in aqueous solvents, then it may be formulated with a non-ionic surfactant such as Tween, or polyethylene glycol. Thus, the compounds and their physiologically solvents may be formulated for administration by inhalation or insufflation (either through the mouth or the nose) or oral, buccal, parenteral, or rectal administration, as examples.

Preparations for oral administration may be suitably formulated to give controlled release of the active compound. In a preferred embodiment, the compounds of the present invention are formulated as controlled release powders of discrete microparticles that can be readily formulated in liquid form. The sustained release powder comprises particles containing an active ingredient and optionally, an excipient with at least one non-toxic polymer.

The powder can be dispersed or suspended in a liquid vehicle and will maintain its sustained release characteristics for a useful period of time. These dispersions or suspensions have both chemical stability and stability in terms of dissolution rate. The powder may contain an excipient comprising a polymer, which may be soluble, insoluble, permeable, impermeable, or biodegradable. The polymers may be polymers or copolymers. The polymer may be a natural or synthetic polymer. Natural polymers include polypeptides (e.g., zein), polysaccharides (e.g., cellulose), and alginic acid. Representative synthetic polymers include those described, but not limited to, those described in column 3, lines 33-45 of U.S. Pat. No. 5,354,556, which is incorporated by reference in its entirety. Particularly suitable polymers include those described, but not limited to those described in column 3, line 46-column 4, line 8 of U.S. Pat. No. 5,354,556 which is incorporated by reference in its entirety.

The sustained release compounds of the invention may be formulated for parenteral administration, e.g., by intramuscular injections or implants for subcutaneous tissues and various body cavities and transdermal devices. In one embodiment, intramuscular injections are formulated as aqueous or oil suspensions. In an aqueous suspension, the sustained release effect is due to, in part, a reduction in solubility of the active compound upon complexation or a decrease in dissolution rate. A similar approach is taken with oil suspensions and solutions, wherein the release rate of an active compound is determined by partitioning of the active compound out of the oil into the surrounding aqueous medium. Only active compounds which are oil soluble and have the desired partition characteristics are suitable. Oils that may be used for intramuscular injection include, but are not limited to, sesame, olive, arachis, maize, almond, soybean, cottonseed and castor oil.

A highly developed form of drug delivery that imparts sustained release over periods of time ranging from days to years is to implant a drug-bearing polymeric device subcutaneously or in various body cavities. The polymer material used in an implant, which must be biocompatible and non-toxic, include but are not limited to hydrogels, silicones, polyethylenes, ethylene-vinyl acetate copolymers, or biodegradable polymers.

The following non-limiting Examples are given by way of illustration only and are not considered a limitation of this invention, many apparent variations of which are possible without departing from the spirit or scope thereof.

EXAMPLES

General Experimental Procedures

All solvents were distilled before use and were removed by rotary evaporation at temperatures up to 35° C. Octadecyl functionalized silica gel (C18) was used for reversed-phase (RP) flash chromatography, and Merck silica gel 60, 200-400 mesh, 40-63 μm, was used for silica gel flash chromatography. Thin layer chromatography (TLC) was carried out using Merck DC-plastikfolien Kieselgel 60 $F_{254}$, first visualized with a UV lamp, and then by dipping in a vanillin solution (1% vanillin, 1% $H_2SO_4$ in ethanol), and heating. Optical rotations were measured on a Perkin-Elmer 241 polarimeter. Mass spectra were recorded on a Kratos MS-80 instrument. NMR spectra, at 25° C., were recorded at 500 or 300 MHz for $^1$H and 125 or 75 MHz for $^{13}$C on Varian INOVA-500 or VXR-300 spectrometers. Chemical shifts are given in ppm on the delta scale referenced to the solvent peaks $CHCl_3$ at 7.25 and $CDCl_3$ at 77.0 ppm, $(CH_3)_2CO$ at 2.15 and $(CD_3)_2CO$ at 30.5 ppm, or $CH_3OD$ at 3.30 and $CD_3OD$ at 39.0 ppm.

HPLC Conditions

The analytical HPLC equipment consisted of a Waters 717 autosampler, 600 pump and controller, and a 2487 UV detector controlled by Omega software. Samples were analyzed by using an RP-18 semi-preparative column (Phenomenex Prodigy 5 mm C18 100A, 250×4.6 mm) with a guard column (Phenomenex SecurityGuard cartridge containing a C18 ODS 4×3 mm, 5 mm column) fitted at 30° C. Samples (5 ml) were analyzed using a mobile phase flow rate of 5.0 ml/min, with UV detection at 280 nm.

Method 1

| Time (minutes) | $CH_3CN$ | $H_2O$ containing 0.1% TFA |
|---|---|---|
| 0 | 11 | 89 |
| 20 | 11 | 89 |
| 30 | 100 | 0 |
| 31 | 11 | 89 |
| 40 | 11 | 89 |

Method 2

| Time (minutes) | $CH_3CN/H_2O$ (95:5) containing 0.1% TFA | $H_2O$ containing 0.1% TFA |
|---|---|---|
| 0 | 11 | 89 |
| 20 | 11 | 89 |
| 30 | 100 | 0 |
| 31 | 11 | 89 |
| 40 | 11 | 89 |

Example 1

3,4,3',4'-Tetrahydroxybenzoin (Compound 1; DC-0001)

Bis(3,4-methylenedioxy)benzoin (compound 1B; DC-0001B)

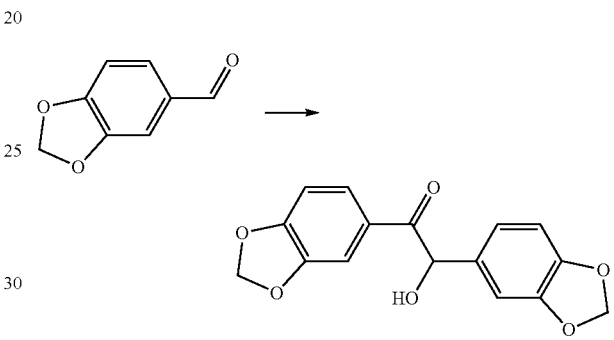

A solution of piperonal (5 g) in ethanol (6.5 ml) was treated with a solution of potassium cyanide (0.5 g) in water (5 ml), then refluxed for 5 h. The resultant precipitate was filtered off, washed with water then crystallized from ethanol to give DC-0001B (2.24 g, 45%) as an off white crystalline solid.

$^1$H-NMR ($CDCl_3$) 7.52 (1H, dd, J 2, 8 Hz), 7.39 (1H, d, J 2 Hz), 6.73-6.82 (4H, m), 6.02 (2H, s), 5.91 (2H, m), 5.76 (1H, d, J 6 Hz) and 4.51 (1H, d, J 6 Hz).

M/z 287 ((M-CH), 100%).

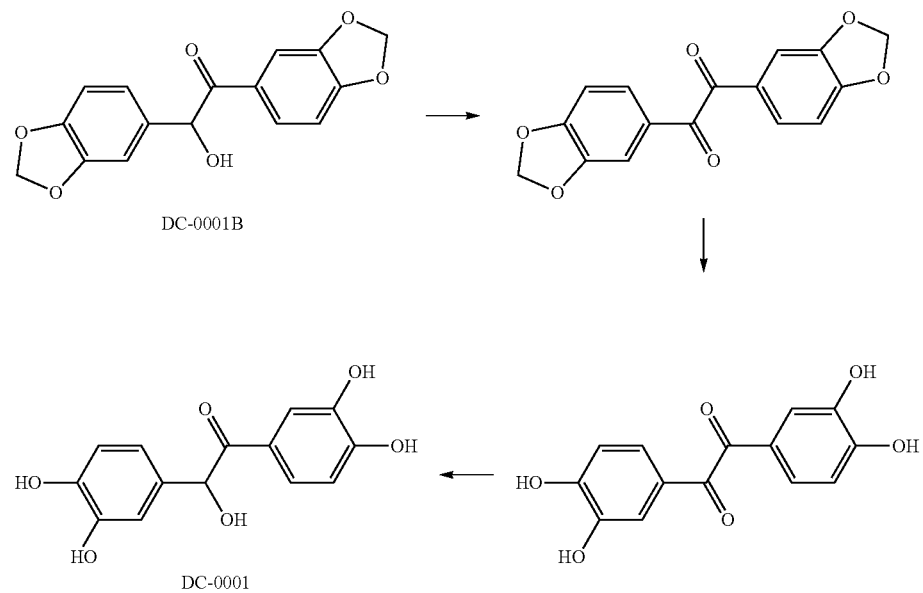

Bis(3,4-methylenedioxy)benzil

A mixture of copper acetate (20 mg), ammonium nitrate (660 mg) and DC-0001B (2 g) in aq. acetic acid (80%, 10 ml) were refluxed together for 90 minutes. The mixture was cooled then poured into water (100 ml) and the product extracted into ethyl acetate (2×100 ml), dried and evaporated in vacuo to give a yellow gum. Trituration from ethanol gave bis(3,4-methylenedioxy)benzil (1.35 g, 68%) as a pale yellow solid.

$^1$H-NMR 7.48 (2H, dd, J 2, 8 Hz) 7.47 (2H, d, J 2 Hz), 6.86 (2H, d, J 8 Hz) and 6.08 (4H, s).

3,4,3',4'-Tetrahydroxybenzil

To a stirred solution of bis(3,4-methylenedioxy)benzil (500 mg) in dry $CH_2Cl_2$ (50 ml) under nitrogen, was slowly added boron tribromide (1.6 ml) then stirring continued for a further 3.5 hours. Methanol (100 ml) was added carefully, then the solvent evaporated in vacuo to a volume of 1 ml, this addition and evaporation was repeated twice more. The product was purified by column chromatography over silica gel when elution with diethylether in dichloromethane gave 3,4,3',4'-tetrahydroxybenzil (217 mg, 47%) as a yellow powder.

$^1$H-NMR 9.35 (2H, bs), 8.80 (2H, bs), 7.48 (2H, d, J 2 Hz), 7.34 (2H, dd, J 2, 8 Hz) and 7.02 (2H, d, J 8 Hz).

M/z 273 ((M−H)$^+$, 100%).

HPLC (method 2) 31.3 minutes.

3,4,3',4'-Tetrahydroxybenzoin (Compound 1; DC-0001)

A solution of the tetrahydroxybenzil (200 mg) in methanol (20 ml) with palladium hydroxide on carbon (20%, 10 mg) was stirred under an atmosphere of hydrogen for 5 minutes. The mixture was filtered through Celite, and the solvents removed in vacuo to give an orange gum. Separation by column chromatography over silica gel eluting with 20% ethyl acetate in dichloromethane gave DC-0001 as an off-white gum (55 mg, 27%). Recrystallization from methanol/dichloromethane gave pure DC-0001 as an off-white powder (27 mg, 13%).

$^1$H-NMR (($CD_3$)$_2$CO) 7.41 (1H, d, J 2 Hz), 7.35 (1H, dd, J 2, 8 Hz), 6.75 (1H, d, J 8 Hz), 6.73 (1H, d, J 2 Hz), 6.69 (1H, d, J 8 Hz), 6.64 (1H, dd, J 2, 8 Hz), 5.69 (1H, bd) and 4.60 (1H, bd).

$^{13}$C-NMR (($CD_3$)$_2$CO) 198.22, 151.41, 145.77, 145.68, 145.43, 132.79, 127.07, 123.92, 120.52, 116.69, 116.20, 115.59, 115.36 and 75.97.

M/Z 275 ((M−H)$^+$, 100%).

HPLC (Method 1) 7.1 minutes.

Example 2

3,4,3',4'-Tetrahydroxydiphenylmethane (compound 3; DC-0003)

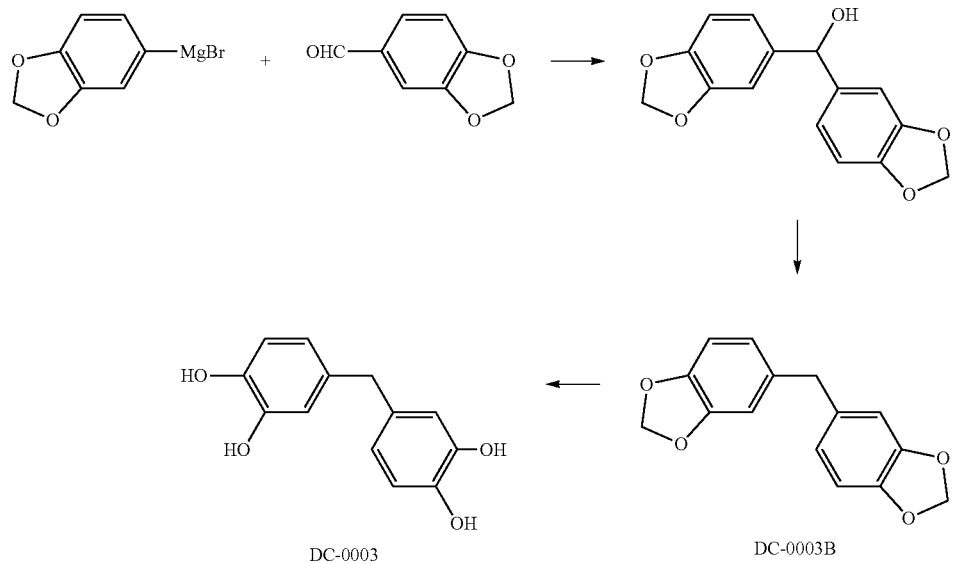

Bis(3,4-methylenedioxyphenyl)methanol

To a solution of piperonal (0.75 g) in solution in dichloromethane (25 ml) was added dropwise 3,4-(methylenedioxy)phenylmagnesium bromide (5 ml, 1M solution in toluene/THF). The mixture was stirred at room temperature overnight, then poured onto water, extracted with dichloromethane, dried and evaporated in vacuo to give the crude alcohol as a brown gum. Purification by column chromatography over silica gel eluting with ethyl acetate in $CH_2Cl_2$ (10 to 20%) gave the pure alcohol as a white gum (1.18 g, 87%).

$^1$H-NMR (CDCl$_3$) 6.7-6.8 (6H, m), 5.93 (4H, s), 5.66 (1H, bs) and 2.18 (bs).

Bis(3,4-methylenedioxyphenyl)methane (compound 3B; DC-0003B)

A solution of the alcohol (2.61 g) in methanol (25 ml)/tetrahydrofuran (30 ml) was shaken with Pd(OH)$_2$/C (20%, 100 mg) under an atmosphere of hydrogen for 12 hours. The mixture was filtered through Celite, then the solvents removed in vacuo to give a brown gum (2.4 g). Crystallization from acetone gave DC-0003B as white crystals (1.14 g, 44%).

$^1$H-NMR (CDCl$_3$) 6.6-6.8 (6H, m), 5.90 (4H, s) and 3.79 (2H, s).

3,4,3',4'-Tetrahydroxydiphenylmethane (compound 3; DC-0003)

To a stirred solution of DC-0003B (0.214 mg) in dry CH$_2$Cl$_2$ (25 ml) under nitrogen, was slowly added boron tribromide (0.4 ml) then stirring was continued for a further 3.5 hours. Methanol (50 ml) was added carefully, then the solvent evaporated in vacuo to a volume of 1 ml; this was then repeated 2 more times. The product was purified by column chromatography over silica gel when elution with ethyl acetate in dichloromethane gave DC-0003 (48%) as an off-white solid.

$^1$H-NMR ((CD$_3$)$_2$CO) 7.73 (2H, s), 7.66 (2H, s), 6.74 (2H, d, J 8 Hz), 6.67 (2H, d, J 2 Hz), 6.56 (2H, dd, J 2, 8 Hz) and 3.70 (2H, s).
$^{13}$C-NMR ((CD$_3$)$_2$CO) 146.51, 144.80, 135.34, 121.59, 117.45, 116.64 and 41.90.
M/z 232 (M$^+$, 100%).
HPLC (Method 1) 31.1 minutes.

Example 3

1,2-bis(3,4-dihydroxyphenyl)ethane (compound 4; DC-0004)

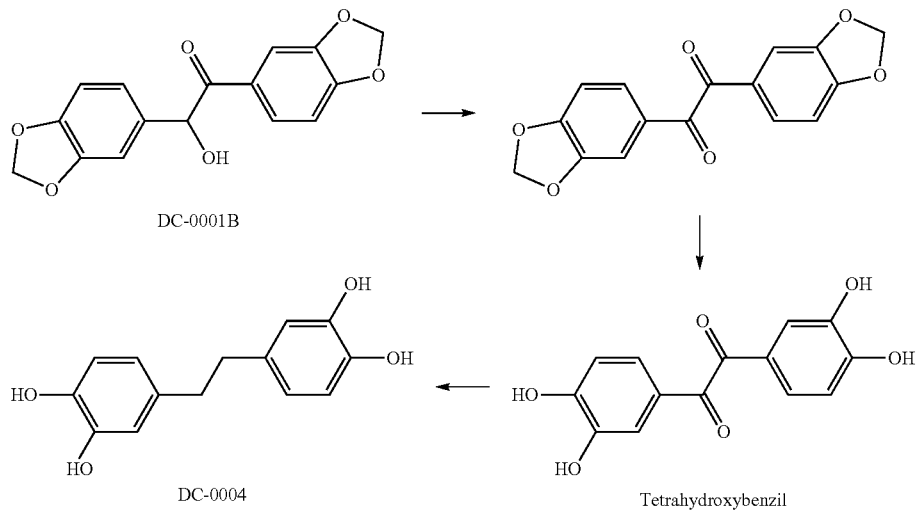

1,2-bis-(3,4-dihydroxyphenyl)ethane (compound 4; DC-0004)

A solution of the tetrahydroxybenzil (see Example 1) (70 mg) in methanol (10 ml) with palladium hydroxide on carbon (20%, 10 mg) was stirred under an atmosphere of hydrogen for 2 hours. The mixture was filtered through Celite, and the solvents removed in vacuo to give an orange gum. Separation by column chromatography over silica gel eluting with 20% ethyl acetate in dichloromethane gave DC-0004 as an off white gum (43 g, 68%).

$^1$H-NMR ((CD$_3$)$_2$CO) 7.73 (4H, bs), 6.80 (2H, d, J 8 Hz), 6.79 (2H, d, J 2 Hz), 6.62 (2H, dd, J 2, 8 Hz) and 2.79 (4H, s).

M/z 245 ((M–H)$^+$, 100%).
HPLC (Method 2) 31.7 minutes.

Example 4

4,6-bis(3,4-dihydroxyphenyl)-3-cyano-2-methylpyridine (compound 8; DC-0008)

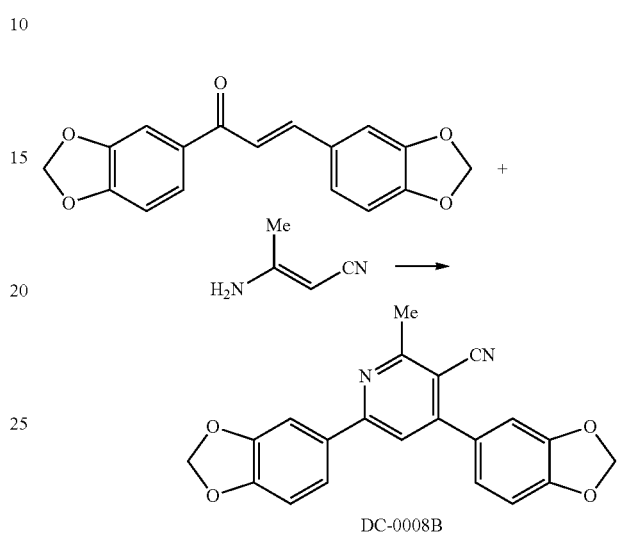

-continued

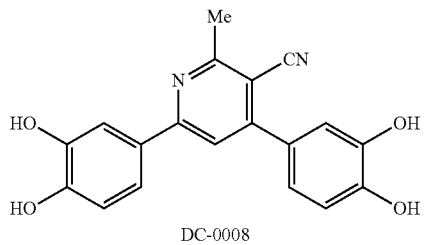

4,6-bis(3,4-methylenedioxyphenyl)-3-cyano-2-methylpyridine (compound 8B; DC-0008B)

To a solution of the chalcone (see below) (300 mg, 1.0 mmol) and 3-aminocrotonitrile (82 mg, 1.2 mmol) in dry acetonitrile was added potassium tert-butoxide (560 mg) and the mixture stirred for 18 h. The mixture was then poured into water, extracted with ethyl acetate, dried and evaporated in vacuo. Recrystallization from dichloromethane/ether gave DC-0008B (152 mg, 42%) as an off-white powder.

$^1$H-NMR (CDCl$_3$) 7.60 (2H, m), 7.52 (1H, s), 7.10 (2H, m), 6.93 (2H, m), 6.07 (2H, s), 6.05 (2H, s) and 2.87 (3H, s).

M/z 359 ((M+1)$^+$, 100%).

4,6-bis(3,4-dihydroxyphenyl)-3-cyano-2-methylpyridine (compound 8; DC-0008)

To a stirred solution of DC-0008B (0.10 g) in dry CH$_2$Cl$_2$ (25 ml) under nitrogen, was slowly added boron tribromide (0.2 ml) then stirring continued for a further 2 hours. Methanol (50 ml) was added carefully, then the solvent evaporated in vacuo to a volume of 1 ml; this was then repeated 2 more times. The product was recrystallized from methanol/acetone to give pure DC-0008 as small yellow crystals (64 mg, 69%).

$^1$H-NMR ((CD$_3$)$_2$CO) 8.19 (1H, s), 7.86 (1H, d, J 2 Hz), 7.75 (1H, dd, J 2, 8 Hz), 7.58 (1H, d, J 2 Hz), 7.45 (1H, dd, J 2, 8 Hz), 7.16 (1H, d, J 8 Hz), 7.13 (1H, d, J 8 Hz), and 2.73 (3H, s).

M/z 335 ((M+1)$^+$, 100%)

HPLC (method 2) 31.8 minutes.

Bis(3,4-methylenedioxy)chalcone (compound 6B; DC-0006B)

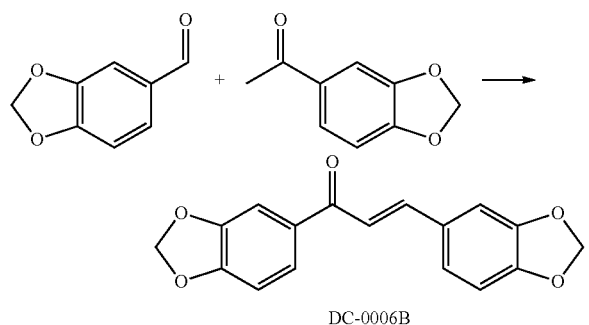

DC-0006B

A mixture of piperonal (460 mg) and 3,4-methylenedioxy-acetophenone (500 mg) in ethanol (20 ml) was treated with 1M NaOH solution (4 ml), then the mixture was stirred overnight. The pale yellow crystalline solid was filtered off, washed with water then cold aqueous ethanol and dried to give pure bis(3,4-methylenedioxy)chalcone DC-0006B (476 mg, 53%).

$^1$H-NMR (CDCl$_3$) 7.72 (1H, d, J 16 Hz), 7.64 (1H, dd, J 2, 8 Hz), 7.52 (1H, d, J 2 Hz), 7.33 (1H, d, J 16 Hz), 7.16 (1H, d, J 2 Hz), 7.12 (1H, dd, J 2, 8 Hz), 6.89 (1H, d, J 8 Hz), 6.84 (1H, d, J 8 Hz), 6.06 (2H, s) and 6.03 (2H, s).

M/z 297 ((M+1)$^+$, 100%).

Example 5

1,4-bis(3,4-dihydroxybenzyl)piperazine (compound 9; DC-0009)

Method 1—Via Methylenedioxy-Protected Compounds

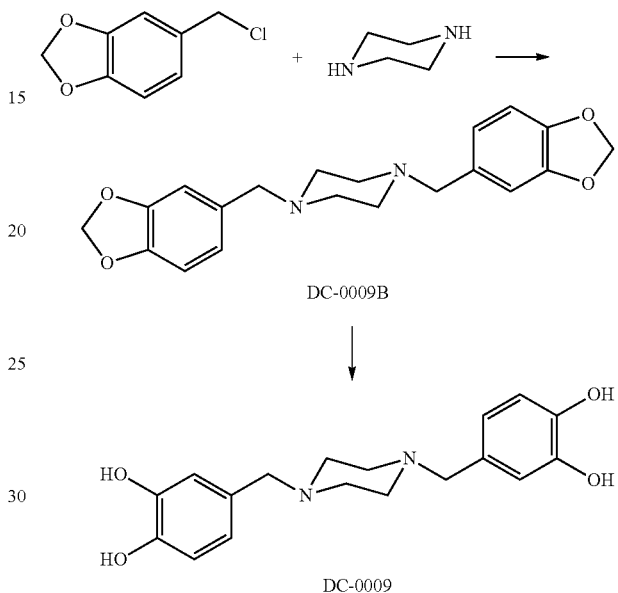

1,4-bis-(3,4-methylenedioxybenzyl)piperazine (DC-0009B)

To a solution of piperazine (207 mg) in dry DMF (5 ml) under nitrogen was added sodium hydride (80% w/w in oil, 250 mg), followed by 3,4-methylenedioxybenzylchloride (0.90 g) and the mixture stirred at room temperature overnight. Aqueous NaOH (50 ml, 1M) was added slowly, then saturated NaCl solution (50 ml) and the product extracted with dichloromethane (2×100 ml). The organic layer was washed with water (2×100 ml), dried and evaporated in vacuo to give a white solid. Column chromatography eluting with increasing proportions of ether in dichloromethane gave pure DC-0009B (0.68 g, 80%) as a white powder.

$^1$H NMR (CDCl$_3$) 6.85 (2H, s), 6.70 (4H, s), 5.94 (4H, s), 3.42 (4H, s) and 2.45 (8H, bs).

M/z 355 ((M+1)$^+$, 100%).

1,4-bis-(3,4-dihydroxybenzyl)piperazine (DC-0009)

To a stirred solution of DC-0009B (200 mg) in dry CH$_2$Cl$_2$ (25 ml) under nitrogen, was slowly added boron tribromide (0.6 ml) then stirring continued for a further 30 minutes. Methanol (50 ml) was added carefully, then the solvent evaporated in vacuo to a volume of 1 ml, and this addition and evaporation was repeated twice more. Purification by column chromatography over silica gel eluting with 20% methanol in chloroform gave a fraction containing crude product DC-0009 (51 mg, 27%) as a white powder.

$^1$H NMR (CD$_3$)$_2$CO) 6.88 (2H, d, J 2 Hz), 6.78 (2H, d, J 8 Hz), 6.67 (2H, dd, J 2, 8 Hz), 3.36 (4H, s) and 2.50 (8H, bs).
$^{13}$C NMR (CD$_3$)$_2$CO) 146.50, 145.85, 131.17, 122.15, 117.78, 116.44, 63.72 and 54.23.
M/z 331 ((M+H)$^+$, 100%).
HPLC (Method 2) 3.79, 3.22 minutes for the mono and di protonated forms.

Method 2—Via Methoxy-Protected Compounds

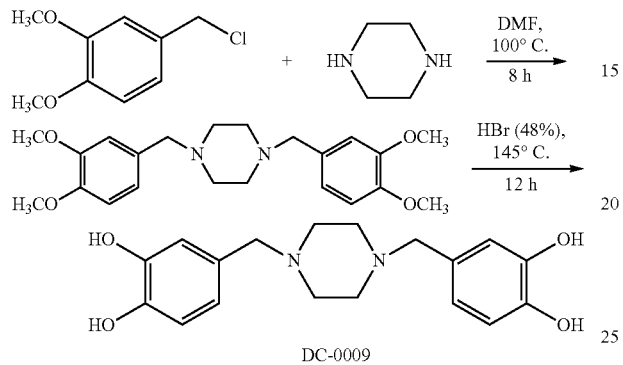

DC-0009

3,4-Dimethoxybenzyl chloride 3,4-dimethoxybenzyl alcohol (20 g, 119 mmol) was dissolved in toluene (60 ml) and cooled to 0° C. Thionyl chloride (7.48 g, 61.4 mmol) was added dropwise to the cooled solution of the alcohol over a period of 30 minutes, and the reaction was maintained at 0° C. for an additional 30 minutes. The reaction was quenched by pouring onto an ice/water mix (100 ml), and the organic phase was separated. The aqueous phase was then extracted into toluene (2×20 ml) and the combined toluene solution was dried over anhydrous sodium sulfate. The toluene was removed at reduced pressure to afford an oil which solidified upon standing, with a yield of 21 g. The material was characterized as a single spot by thin layer chromatography (TLC).

1,4-Bis(3,4-dimethoxybenzyl)piperazine 3,4-dimethoxybenzyl chloride (10 g, 53.6 mmol) was combined with piperazine (2.3 g, 26.8 mmol) in anhydrous DMF (30 ml) and heated with stirring under nitrogen for 8 hours at 95-100° C. The cooled reaction mixture was diluted with water (100 ml) and acidified to pH 1 with concentrated hydrochloric acid. The white precipitate was collected by filtration and washed with water (50 ml). The solid was re-suspended in water (50 ml) and the pH adjusted to >9 by the dropwise addition of sodium hydroxide solution (50% NaOH in water). The resultant white solid was collected by filtration and dried under vacuum at 50° C., yield 10 g.

1,4-Bis(3,4-dihydroxybenzyl)piperazine (DC-0009)

1,4-Bis(3,4-dimethoxybenzyl)piperazine (5 g, 12.95 mmol) was combined with hydrobromic acid (50 ml of 48% w/w solution in water) and the solution heated slowly over 1 hour to 145° C. Reaction was maintained at 145° C. for 12 h at which time TLC revealed disappearance of starting material. The cooled solution was diluted with water (200 ml), carefully neutralized with saturated aqueous sodium hydrogen carbonate, and ethyl acetate (100 ml) added. The crude aqueous solvent mixture was filtered through Celite and the ethyl acetate layer separated. The aqueous layer was extracted with ethyl acetate (2×50 ml), and the combined extracts washed with water (50 ml), and dried (Na$_2$SO$_4$). The solvent was removed under reduced pressure and the residue recrystallized from toluene and methyl ethyl ketone to afford the product, DC-0009, 100 mg (98%, pure by HPLC analysis).

Example 6

N,N'-bis(3,4-dihydroxybenzyl)-trans-1,2-diaminocyclohexane (compound 12; DC-0012)

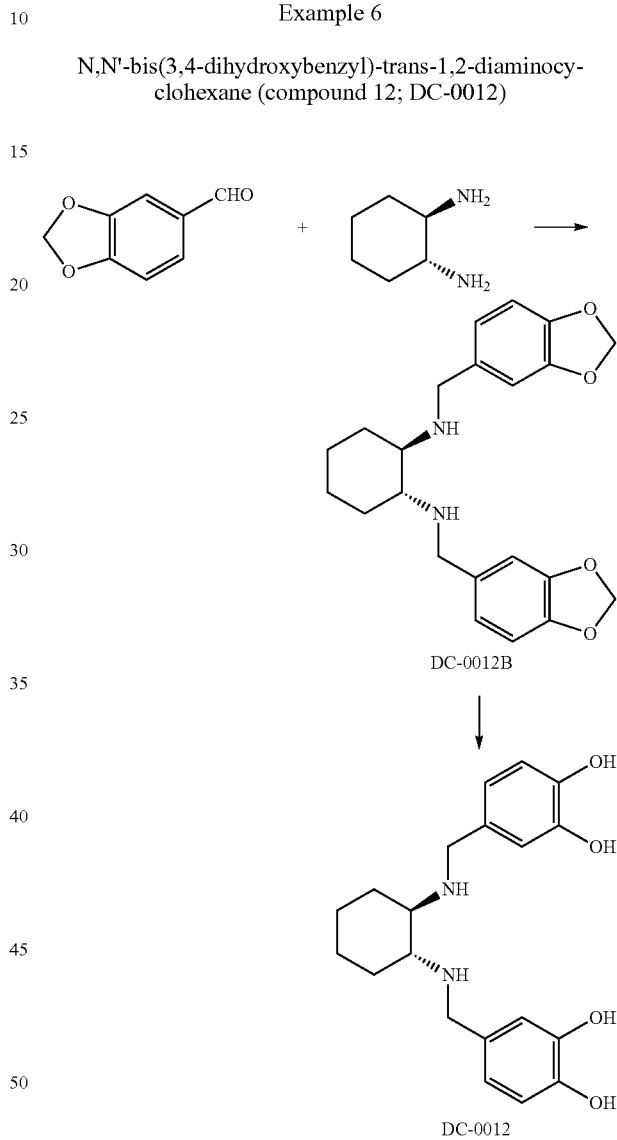

N,N'-bis(3,4-methylenedioxybenzyl)-trans-1,2-diaminocyclohexane (compound 12B; DC-0012B)

To a solution of piperonal (0.8 g, 5.3 mmol) and 1,2-diaminocyclohexane (0.296 g, 2.6 mmol) in dry methanol (25 ml) was added sodium cyanoborohydride (0.38 g, 6 mmol) and the mixture stirred for 48 h. The mixture was filtered and the solvents removed in vacuo to give the crude product. Crystallization from methanol gave DC-0012B as an off-white crystalline solid (0.298 g, 30%).

$^1$H-NMR (CDCl$_3$) 6.83 (2H, s), 6.75 (4H, s), 5.94 (4H, m), 3.80 (2H, d, J 13 Hz), 3.56 (2H, d, J 13 Hz), 2.22 (2H, m), 2.18 (2H, m), 1.74 (4H, m), 1.22 (2H, m) and 1.02 (2H, m).

N,N'-bis(3,4-dihydroxybenzyl)-trans-1,2-diaminocyclohexane (compound 12; DC-0012)

To a stirred solution of DC-0012B (0.25 g) in dry $CH_2Cl_2$ (25 ml) under nitrogen, was slowly added boron tribromide (0.31 ml), then stirring was continued for a further 4 hours. Methanol (100 ml) was added carefully, then the solvent evaporated in vacuo to a volume of 1 ml; this addition and evaporation was then repeated twice more, and then water (2 ml) was added and the product lyophilized to give DC-0012 as a pale brown solid (150 mg, 64%).

$^1$H-NMR ($D_2O$) 6.88 (2H, br s), 6.84 (2H, d, J 8 Hz), 6.76 (2H, br d, J 8 Hz), 4.20 (2H, d, J 13 Hz), 3.98 (2H, d, J 13 Hz), 3.41 (2H, br s), 2.24 (2H, br s), 1.74 (2H, br s), 1.63 (2H, br s) and 1.40 (2H, br s).

M/z 359 ((M+1)$^+$, 100%).
HPLC (Method 2) 8.2 minutes.

Example 7

2,4-bis(3,4-dihydroxybenzyl)-3-tropinone (compound 19; DC-0019)

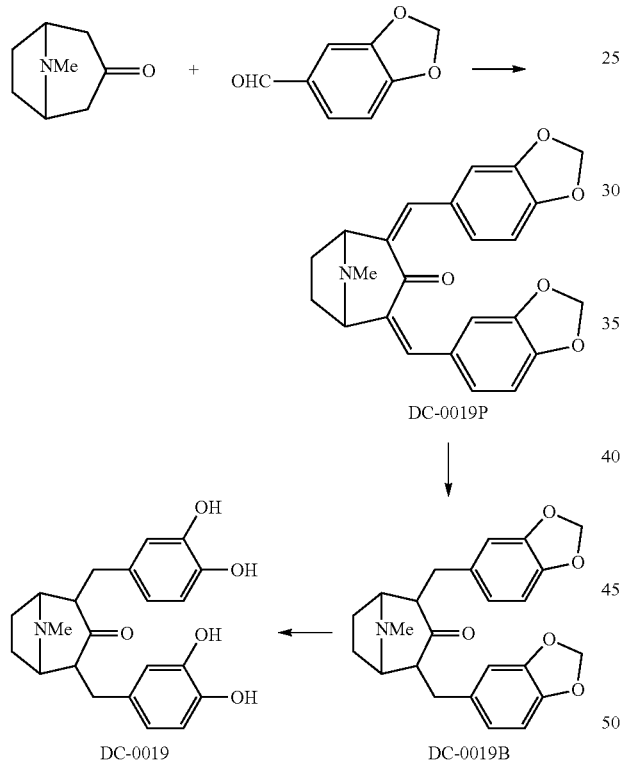

A mixture of tropinone (418 mg, 3 mmol) and 3,4-methylenedioxybenzaldehyde (900 mg, 6 mmol) in ethanol (20 ml) was treated with 1M NaOH solution (4 ml), and then the mixture was stirred overnight. The yellow crystalline solid was filtered off, washed with water, then cold aqueous ethanol, and dried to give pure DC-0019P (938 mg, 77%).

$^1$H-NMR (CDCl$_3$) 7.73 (2H, s), 6.88 (6H, m), 6.02 (4H, s), 4.39 (2H, m), 2.60 (2H, m), 2.31 (3H, s) and 1.98 (2H, q, J 8 Hz).

M/z 404 ((M+1)$^+$, 100%).

2,4-bis(3,4-methylenedioxybenzyl)-3-tropinone (compound 19B; DC-0019B)

A mixture of DC-0019P (500 mg, 1.24 mmol) and 10% Pd/C (100 mg) in ethyl acetate (50 ml) was stirred overnight under an atmosphere of hydrogen. The mixture was filtered through Celite and evaporated in vacuo. Crystallization of the residue from dichloromethane/ether gave pure DC-0019B (366 mg, 72%) as a white crystalline solid.

$^1$H-NMR (CDCl$_3$) 6.69 (2H, d, J 8 Hz), 6.61 (2H, d, J 2 Hz), 6.58 (2H, dd, J 2, 8 Hz), 5.90 (4H, s), 3.17 (4H, m), 2.86 (2H, m), 2.36 (3H, s), 2.24 (2H, dd, J 8, 12 Hz), 1.83 (2H, m) and 1.60 (2H, q, J 8 Hz).

M/z 408 ((M+1)$^+$, 100%).

2,4-bis(3,4-dihydroxybenzyl)-3-tropinone (compound 19; DC-0019)

To a stirred solution of DC-0019B (0.10 g) in dry $CH_2Cl_2$ (25 ml) under nitrogen, was slowly added boron tribromide (0.2 ml) then stirring continued for a further 2 hours. Methanol (50 ml) was added carefully, then the solvent evaporated in vacuo to a volume of 1 ml, this was repeated 2 more times. The product was crystallized from methanol to give pure DC-0019 (42 mg, 45%) as a white solid.

$^1$H-NMR ($D_2O$) 6.75 (2H, d, J 8 Hz), 6.68 (2H, d, J 2 Hz), 6.59 (2H, dd, J 2, 8 Hz), 3.84 (2H, bs), 3.31 (4H, s), 3.07 (2H, dd, 6, 14 Hz), 2.82 (3H, s), 2.37 (dd, J 8, 14 Hz) and 2.05 (2H, d 8 Hz).

M/z 384 ((M+1)$^+$, 100%).
HPLC (method 2) 30.9 minutes.

Example 8

α-(3,4-Dihydroxybenzamido)-3,4-dihydroxycinnamic acid 3,4-dihydroxybenzylamide (compound 21; DC-0021)

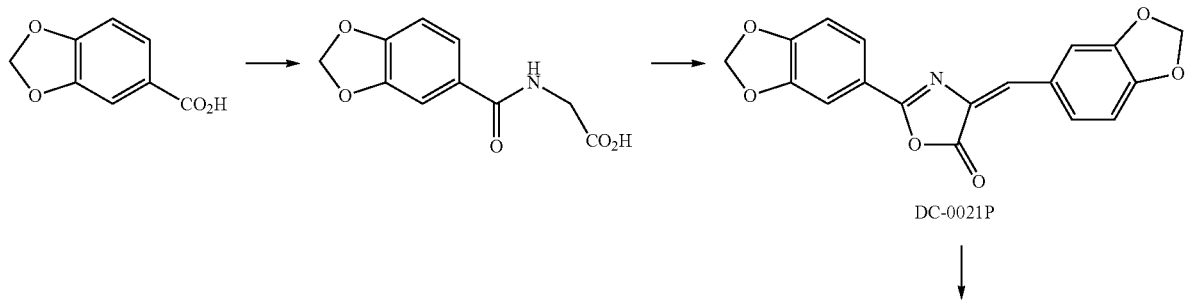

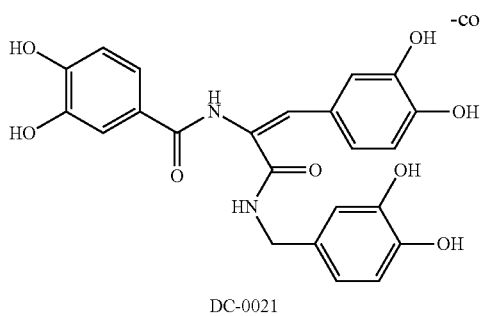
DC-0021

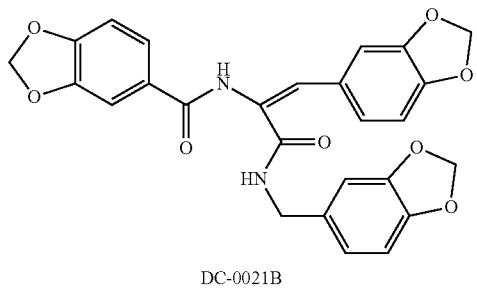
DC-0021B

2-(3,4-methylenedioxyphenyl)-4-(3,4-methylenedioxybenzylamino)methylene-4H-oxazol-5-one (DC-0021P)

DC-0021P is also referred to as DC-0022B, and is commercially available. It was prepared from (3,4-methylenedioxybenzoyl)aminoacetic acid [3,4-methylenedioxyhippuric acid] (prepared by the method of Acheson et al., *J. Chem. Soc. Abstracts*, 1960:3457-3461, from 3,4-methylenedioxybenzoic acid), by reaction with piperonaldehyde using the method described by Van der Eycken et al., *Tet. Lett.*, 30(29): 3873-3876, 1989.

$^1$H-NMR (CDCl$_3$) 8.09 (1H, d, J 2 Hz), 7.75 (1H, dd, J 2, 8 Hz), 7.62 (1H, d, J 2 Hz), 7.45 (1H, dd, J2, 8 Hz), 7.12 (1H, s), 6.94 (1H, d, J 8 Hz), 6.90 (1H, d, J 8 Hz), 6.11 (2H, s) and 6.08 (2H, s).

m/z 338 (M+H)$^+$.

α-(3,4-methylenedioxybenzamido)-3,4-methylenedioxycinnamic acid 3,4-methylenedioxybenzylamide (compound 21B; DC-0021B)

A mixture of DC-0021P (250 mg, 0.74 mmol) and 3,4-methylenedioxybenzylamine (0.112 g, 0.74 mmol) in acetic acid (glacial, 3 ml) were heated together under reflux for 30 minutes. The reaction was quenched with ethyl acetate, washing with sodium bicarbonate, dried and evaporated in vacuo to give the crude product. Purification by column chromatography, eluting with hexane/ethyl acetate (50/50), followed by recrystallization from ethanol/water gave pure DC-0021B (218 mg, 60%).

$^1$H-NMR ((CD$_3$)$_2$CO) 9.09 (1H, bs), 8.06 (1H, bt, J 7 Hz), 7.70 (1H, dd, J 2, 8 Hz), 7.56 (1H, d, J 2 Hz), 7.37 (1H, s), 7.16 (1H, d, J 2 Hz), 7.08 (1H, dd, J 2, 8 Hz), 7.00 (1H, d, J 8 Hz), 6.94 (1H, d, J 2 Hz), 6.86 (1H, d, J 8 Hz), 6.84 (1H, dd, J2, 8 Hz), 6.77 (1H, d, J 8 Hz), 6.14 (2H, s), 6.02 (2H, s), 5.98 (2H, s) and 4.43 (2H, d, J 7 Hz).

M/z 489 ((M+1)$^+$, 100%).

α-(3,4-dihydroxybenzamido)-3,4-dihydroxycinnamic acid 3,4-dihydroxybenzylamide (compound 21; DC-0021)

To a stirred solution of DC-0021B (85 mg) in dry CH$_2$Cl$_2$ (20 ml) under nitrogen, was slowly added boron tribromide (0.2 ml) then stirring continued for a further 2 hours. Methanol (50 ml) was added carefully, then the solvent evaporated in vacuo to a volume of 1 ml; this was repeated 2 more times. Purification by column chromatography over silica gel eluting with 20% methanol in chloroform gave pure DC-0021 as a pale yellow solid (42 mg, 53%).

$^1$H-NMR ((CD$_3$)$_2$CO) 7.75 (1H, d, J 2 Hz), 7.63 (1H, dd, J 2, 8 Hz), 7.50 (1H, s), 7.34 (1H, d, J 2 Hz), 7.12 (1H, dd, J 2, 8 Hz), 7.00-7.04 (2H, m), 6.91 (1H, d, J 8 Hz), 6.80-6.85 (2H, m) and 4.68 (2H, s).

M/z 451 ((M−1)$^+$, 100%).

HPLC (method 2) 27.1 minutes.

Example 9

1,4-bis(3,4-dihydroxybenzoyl)piperazine (compound 23; DC-0023)

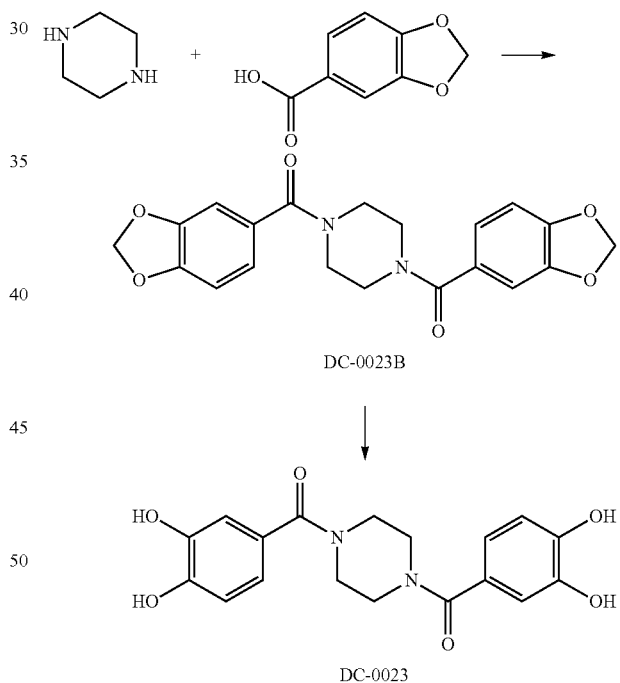
DC-0023B

DC-0023

1,4-bis(3,4-methylenedioxybenzoyl)piperazine (compound 23B; DC-0023B)

A suspension of piperonylic acid (0.5 g) in thionyl chloride (15 ml) was refluxed for 1 h under nitrogen, when a clear solution had been formed. The solvents were removed in vacuo to give the acid chloride as a white solid. The solid was dissolved in dry dichloromethane (7 ml) and added dropwise to a stirred solution of piperazine (0.13 g) in dry dichloromethane (20 ml) containing pyridine (0.5 ml). The mixture was refluxed for 30 minutes, diluted with more dichloromethane (50 ml), then washed with aqueous HCl (1M, 50 ml) followed by aqueous NaOH (1M, 50 ml), dried and evaporated in vacuo to give the crude product. Crystallization from methanol/water gave DC-0023B as a white solid (532 mg, 92%).

$^1$H-NMR (CDCl$_3$) 6.80-6.96 (6H, m), 6.00 (4H, s), and 3.62 (8H, bs).

1,4-bis(3,4-dihydroxybenzoyl)piperazine (compound 23; DC-0023)

To a stirred solution of DC-0023B (0.20 g) in dry CH$_2$Cl$_2$ (25 ml) under nitrogen, was slowly added boron tribromide (0.4 ml) then stirring continued for a further 2 hours. Methanol (50 ml) was added carefully, then the solvent evaporated in vacuo to a volume of 1 ml, this was repeated 2 more times. The product was crystallized from methanol/dichloromethane to give pure DC-0023 (141 mg, 75%) as a white solid.

$^1$H-NMR (CD$_3$OD) 6.88 (2H, s), 6.81 (4H, s) and 3.66 (8H, s).

M/z 357 ((M–H)$^+$, 100%).

Example 10

N,N'-bis(3,4-dihydroxybenzoyl)-trans-1,2-diaminocyclohexane (compound 26; DC-0026)

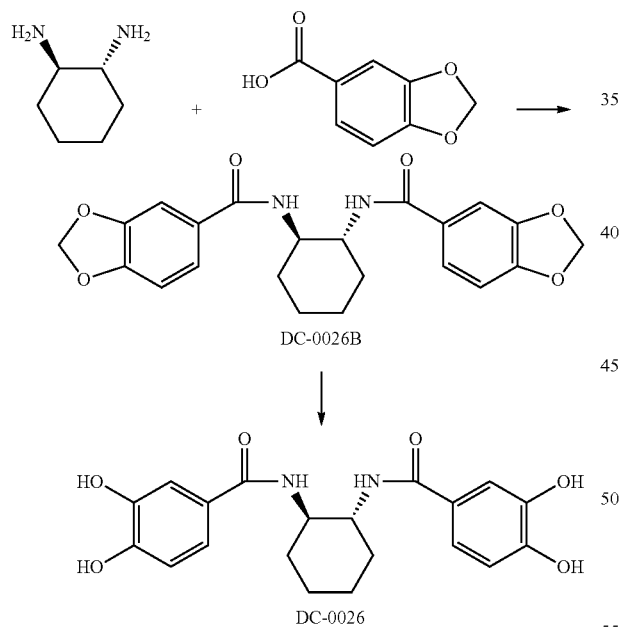

N,N'-bis(3,4-methylenedioxybenzoyl)-trans-1,2-diaminocyclohexane (compound 26B; DC-0026B)

A suspension of piperonylic acid (0.5 g) in thionyl chloride (15 ml) was refluxed for 1 h under nitrogen, when a clear solution had been formed. The solvents were removed in vacuo to give the acid chloride as a white solid. The solid was dissolved in dry dichloromethane (7 ml) and added dropwise to a stirred solution of trans-1,2-diaminocyclohexane (0.17 g) in dry dichloromethane (20 ml) containing pyridine (0.5 ml). The mixture was refluxed for 30 minutes, diluted with more dichloromethane (50 ml), then washed with aqueous HCl (1M, 50 ml), followed by aqueous NaOH (1M, 50 ml), dried and evaporated in vacuo to give the crude product. Crystallization from methanol/water gave DC-0026B as a white solid (544 mg, 94%).

$^1$H-NMR (CDCl$_3$) 7.27 (2H, m), 6.77 (2H, d, J 8 Hz), 6.67 (2H, bs), 5.98 (4H, s), 3.92 (2H, bs), 2.20 (2H, bd), 1.80 (2H, bs) and 1.38 (4H, bm).

N,N'-bis(3,4-dihydroxybenzoyl)-trans-1,2-diaminocyclohexane (compound 26; DC-0026)

To a stirred solution of DC-0026B (0.20 g) in dry CH$_2$Cl$_2$ (25 ml) under nitrogen, was slowly added boron tribromide (0.4 ml) then stirring continued for a further 2 hours. Methanol (50 ml) was added carefully, then the solvent evaporated in vacuo to a volume of 1 ml, this addition and evaporation was repeated twice more. The product was crystallized from methanol/dichloromethane to give pure DC-0026 (161 mg, 86%) as a white solid.

$^1$H-NMR (CD$_3$OD) 7.18 (2H, s), 7.11 (2H, d, J 8 Hz), 6.73 (2H, d, J 8 Hz), 3.89 (2H, m), 2.06 (2H, m), 1.83 (2H, m) and 1.44 (2H, m).

M/z 385 ((M–H)$^+$, 100%).

HPLC (Method 1) 30.9 minutes.

Example 11

3,4-dihydroxybenzoic acid 3,4-dihydroxyanilide (compound 51; DC-0051)

Method 1—Via Methylenedioxy-Protected Compounds

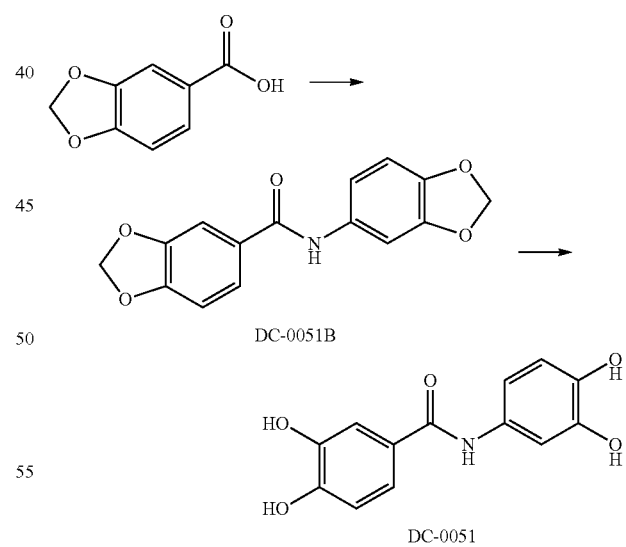

3,4-methylenedioxybenzoic acid 3,4-methylenedioxyanilide (compound 51; DC-0051B)

To a solution of piperonylic acid (500 mg, 3 mmol) in dry CH$_2$Cl$_2$ (25 ml) under nitrogen, was added oxalyl chloride (573 mg, 4.5 mmol) with three drops of dry DMF, and the mixture was stirred for 1 hour. Solvents were removed in vacuo giving the acid chloride as a white solid. To a solution of the acid chloride in dry CH$_2$Cl$_2$ (50 ml) under nitrogen, cooled to 0° C., was added dropwise, a solution made up of 3,4-(methylenedioxy)aniline (498 mg, 30.1 mmol) and pyridine (0.5 ml) in CH$_2$Cl$_2$ (5 ml). The reaction mixture was stirred for 30 minutes at room temperature, then diluted by the addition of CH$_2$Cl$_2$ (100 ml), washed with aqueous HCl (50 ml, 10%) and sodium bicarbonate solution (50 ml) then dried. Solvents were removed in vacuo to give the crude product as a brown crystalline material. Recrystallization from aqueous ethanol gave DC-0051B as small silvery crystals (0.516 g, 60%).

$^1$H-NMR (CDCl$_3$) 7.60 (1H, br s), 7.35 (3H, m), 6.88 (2H, m), 6.78 (1H, d, J 9 Hz), 6.06 (2H, s) and 5.98 (2H, s).

3,4-dihydroxybenzoic acid 3,4-dihydroxyanilide (compound 51; DC-0051)

To a solution of DC-0051B (100 mg) in dry CH$_2$Cl$_2$ (25 ml) under nitrogen was added BBr$_3$ (0.2 ml) and the mixture was stirred for 6 hours. After stirring, aqueous 3M HCl (25 ml) was carefully added to the reaction mixture. The product was extracted into EtOAc (200 ml), dried and evaporated in vacuo to give the crude product. Purification by column chromatography (Silica: Hexane/EtOAc 30:70) gave DC-0051 as an off-white solid (71 mg, 77%).

$^1$H-NMR (CD$_3$OD) 7.60 (1H, br s), 7.38 (1H, d, J 2 Hz), 7.33 (1H, dd, J 2, 8 Hz), 7.21 (1H, d, J 2 Hz), 6.89 (1H, dd, J 2, 8 Hz), 6.86 (1H, d, J 8 Hz) and 6.76 (1H, d, J 8 Hz).

M/z 262 ((M+1)$^+$, 100%)

HPLC (method 2) 15.1 minutes.

Method 2—Via Benzyloxy- and Methoxymethoxy-Protected Compounds

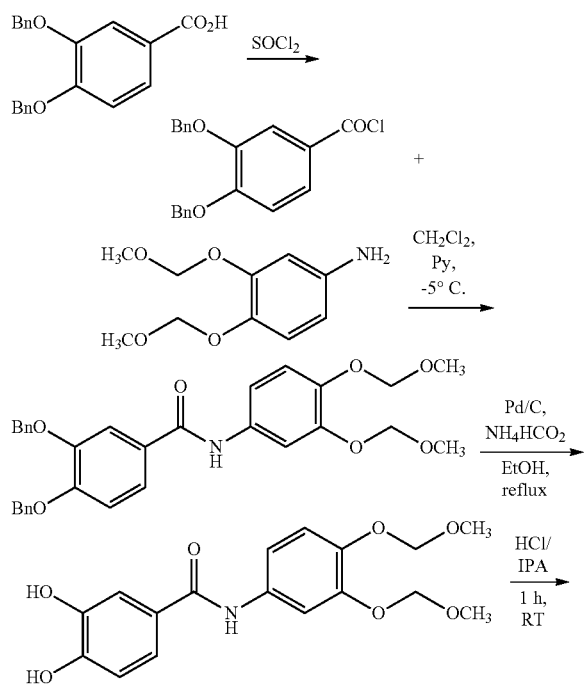

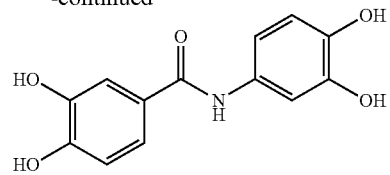

3,4-dibenzyloxybenzoyl chloride 3,4-dibenzyloxybenzoic acid (3.1 g. 9.3 mmol) was combined with pyridine (5 drops, catalytic) and thionyl chloride (15 ml, 205 mmol). The solution was heated at reflux for 4 h, cooled, and excess thionyl chloride removed under reduced pressure. The crude product was dissolved in benzene (50 ml), and stripped of solvent under vacuum. The benzoyl chloride (theoretical yield 3.4 g) was then dissolved in dichloromethane and used directly in the next step.

3,4-dibenzyloxybenzoic acid 3,4-di(methoxymethoxy)anilide 3,4-di(methoxymethoxy)aniline (0.484 g, 2.2 mmol) was dissolved in dichloromethane (5 ml) and pyridine (3 ml) and cooled to −5° C., while stirring under nitrogen. A solution of 3,4-dibenzyloxybenzoyl chloride in dichloromethane (0.8 g, 2.2 mmol of acid chloride) was added dropwise over 30 minutes. The reaction was allowed to stir at 0° C. for 30 minutes then warmed to room temperature over 30 minutes. The reaction was diluted with dichloromethane (100 ml), washed with aqueous citric acid (3×300 ml of a 2% w/v solution), aqueous sodium hydroxide (2×35 ml of a 2% w/v solution) and dried (Na$_2$SO$_4$). Removal of the solvent under reduced pressure afforded a solid, 0.97 g. The crude product was triturated with warm methanol (10 ml) and filtered to afford the desired product, 0.5 g.

3,4-dihydroxybenzoic acid 3,4-di(methoxymethoxy)anilide 3,4-dibenzyloxybenzoic acid 3,4-di(methoxymethoxy) benzanilide (0.2 g, 0.4 mmol) was combined with ethanol (10 ml), and palladium on charcoal (40 mg of 10% Pd/C). The reaction was heated to reflux with stirring under nitrogen, and ammonium formate (0.8 g, 12.7 mmol) was added portion wise over 15 min and then held at reflux for two hours. The cooled reaction solution was filtered to remove the catalyst and concentrated under reduced pressure to afford the crude product, 0.13 g.

3,4-dihydroxybenzoic acid 3,4-dihydroxyanilide (compound 51; DC-0051)

3,4-dihydroxybenzoic acid 3,4-di(methoxymethoxy)benzanilide (0.17 g, 0.49 mmol) was combined with a 25% solution of hydrogen chloride in isopropyl alcohol (15 ml) and water (1 ml). The reaction was stirred at room temperature for 1 h and the solvent removed under reduced pressure.

Trituration with diethyl ether (5 ml) afforded DC-0051 as a solid which was dried under vacuum at 30° C., yield 60 mg.

Example 12

3,4-dihydroxybenzoic acid 3,4-dihydroxybenzylamide (compound 52; DC-0052)

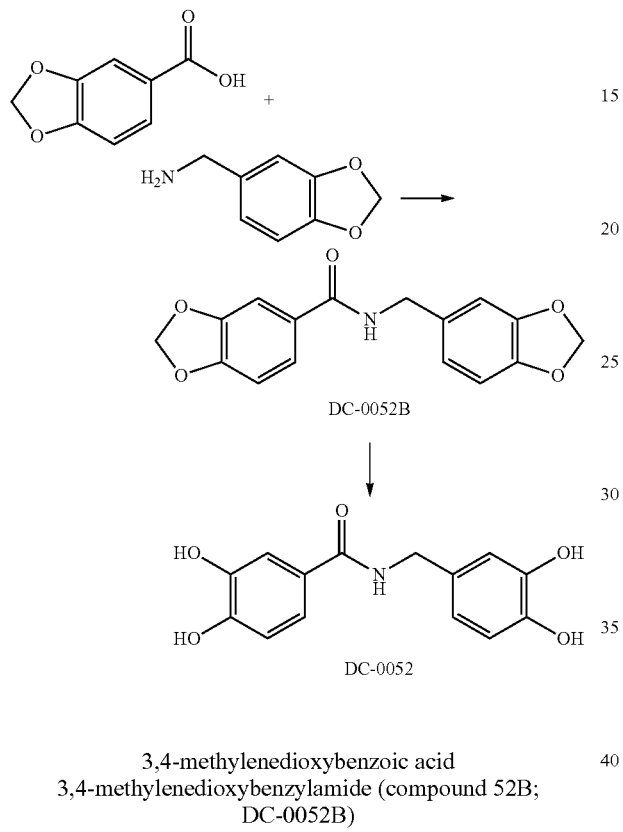

3,4-methylenedioxybenzoic acid 3,4-methylenedioxybenzylamide (compound 52B; DC-0052B)

A suspension of piperonylic acid (0.5 g) in thionyl chloride (15 ml) was refluxed for 1 h under nitrogen, when a clear solution had been formed. The solvents were removed in vacuo to give the acid chloride as a white solid. The solid was dissolved in dry dichloromethane (7 ml) and added dropwise to a stirred solution of piperonylamine (0.45 g) in dry dichloromethane (20 ml) containing pyridine (0.5 ml). The mixture was refluxed for 30 minutes, diluted with more dichloromethane (50 ml), then washed with aqueous HCl (1M, 50 ml) followed by aqueous NaOH (1M, 50 ml), dried and evaporated in vacuo to give the crude product. Crystallization from methanol/water gave DC-0052B as a white solid (733 mg, 79%).

$^1$H-NMR (CDCl$_3$) 7.27 (2H, m), 6.79 (4H, m), 6.01 (2H, s), 5.94 (2H, s) and 4.51 (2H, d, J 5 Hz).

3,4-dihydroxybenzoic acid 3,4-dihydroxybenzylamide (compound 52; DC-0052)

To a stirred solution of DC-0052B (0.20 g) in dry CH$_2$Cl$_2$ (25 ml) under nitrogen, was slowly added boron tribromide (0.4 ml) then stirring continued for a further 2 hours. Methanol (50 ml) was added carefully, then the solvent evaporated in vacuo to a volume of 1 ml; this was then repeated 2 more times. The product was crystallized from methanol/dichloromethane to give pure DC-0052 (65 mg, 35%) as a white solid.

$^1$H-NMR (CD$_3$OD) 7.29 (2H, s), 7.22 (2H, d, J 8 Hz), 6.78 (4H, m), 6.67 (4H, m) and 4.38 (4H, d, J 5 Hz).

M/z 274 ((M−H)$^+$, 100%)

HPLC (Method 1) 10.4 minutes.

Example 13

3-(3,4-dihydroxyphenyl)propionic acid 3,4-dihydroxyanilide (compound 57; DC-0057)

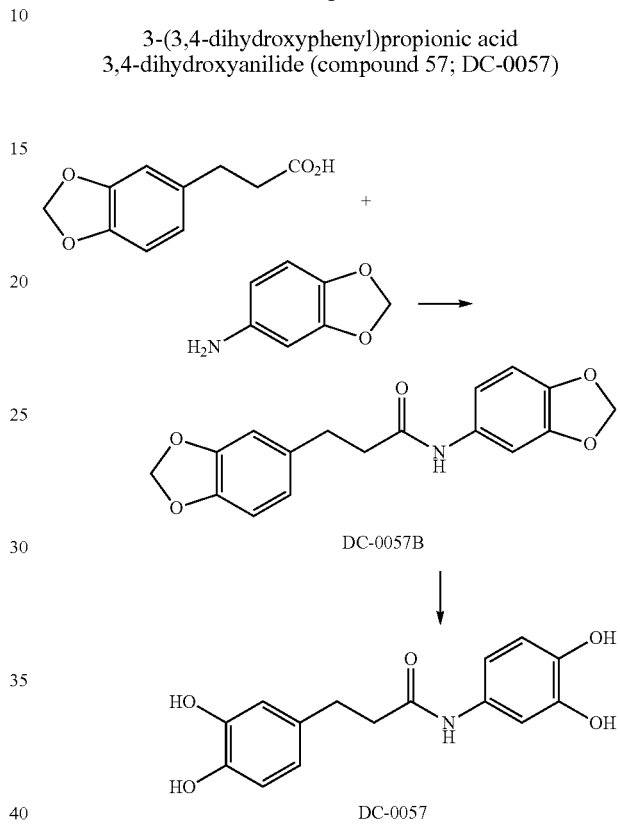

3-(3,4-methylenedioxyphenyl)propionic acid 3,4-methylenedioxyanilide (compound 57B; DC-0057B)

To a solution of 3,4-(methylenedioxy)dihydrocinnamic acid (0.4 g) in dry CH$_2$Cl$_2$ (25 ml) under nitrogen, was added oxalyl chloride (0.5 ml) with three drops of dry DMF and the mixture stirred for 1 hour. Solvents were removed in vacuo giving the acid chloride as a yellow solid. To a solution of the acid chloride in dry CH$_2$Cl$_2$ (50 ml) under nitrogen, cooled to 0° C., was added dropwise, a solution of 3,4-(methylenedioxy)aniline (0.35 g) and pyridine (0.2 ml) in CH$_2$Cl$_2$ (5 ml). The reaction mixture was stirred for 30 minutes at room temperature, diluted with CH$_2$Cl$_2$ (100 ml), washed with aqueous HCl (100 ml, 10%) and sodium bicarbonate solution (100 ml) then dried and evaporated in vacuo to give DC-0057B as a dark brown powder (0.549 g, 85%).

$^1$H-NMR (CDCl$_3$) 7.15 (1H, d, J 2 Hz), 6.86 (1H, bs), 6.60-6.75 (5H, m), 5.93 (2H, s), 5.92 (2H, s), 2.95 (2H, t, J 4 Hz) and 2.57 (2H, t, J 4 Hz).

3-(3,4-dihydroxyphenyl)propionic acid 3,4-dihydroxyanilide (compound 57; DC-0057)

To a stirred solution of DC-0057B (0.20 g) in dry CH$_2$Cl$_2$ (25 ml) under nitrogen, was slowly added boron tribromide (0.4 ml), then stirring was continued for a further 2 hours. Methanol (50 ml) was added carefully, then the solvent evaporated in vacuo to a volume of 1 ml, this was repeated 2 more times to give pure DC-0057 as a brown solid (143 mg, 77%).

$^1$H-NMR ((CD$_3$)$_2$CO) 7.31 (1H, s), 6.98 (3H, m), 6.84 (1H, d, J 8 Hz), 6.78 (1H, dd, J 2, 8 Hz), 3.24 (2H, m) and 3.16 (2H, m).

M/z 370, 368 (M+HBr)$^+$, 288 ((M–H)$^+$, 100%)

HPLC (Method 2) 20.6 minutes.

Example 14

3-(3,4-dihydroxyphenyl)propionic acid 3,4-dihydroxybenzylamide (compound 58; DC-0058)

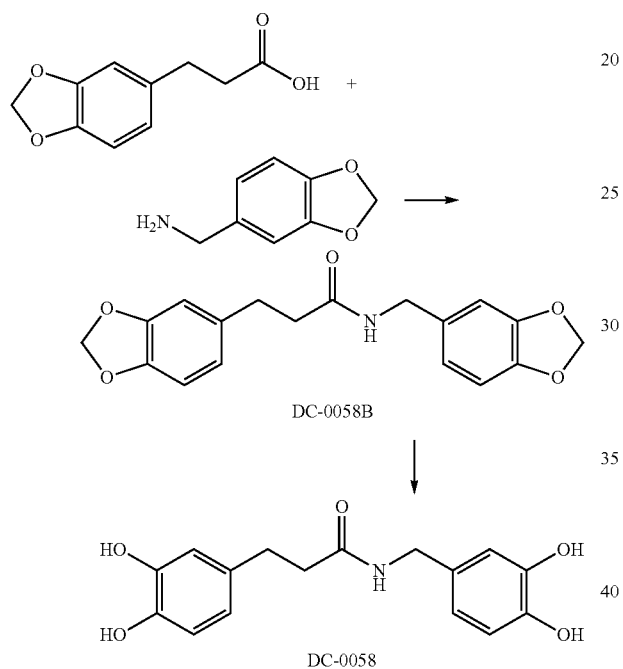

3-(3,4-methylenedioxyphenyl)propionic acid 3,4-methylenedioxybenzylamide (compound 58B; DC-0058B)

To a solution of 3,4-methylenedioxydihydrocinnamic acid (0.4 g) in dry CH$_2$Cl$_2$ (25 ml) under nitrogen, was added oxalyl chloride (0.5 ml) with three drops of dry DMF and the mixture was stirred for 1 hour. Solvents were removed in vacuo giving the acid chloride as a yellow solid. To a solution of the acid chloride in dry CH$_2$Cl$_2$ (50 ml) under nitrogen, cooled to 0° C., was added dropwise, a solution of 3,4-(methylenedioxy)benzylamine (0.35 g) and pyridine (0.2 ml) in CH$_2$Cl$_2$ (5 ml). The reaction mixture was stirred for 30 minutes at room temperature, diluted with CH$_2$Cl$_2$ (100 ml), washed with aqueous HCl (100 ml; 10%) and sodium bicarbonate solution (100 ml) then dried and evaporated in vacuo to give DC-0058B as an off white powder (0.536 g, 80%).

3-(3,4-dihydroxyphenyl)propionic acid 3,4-dihydroxybenzylamide (compound 58; DC-0058)

To a stirred solution of DC-0058B (0.20 g) in dry CH$_2$Cl$_2$ (25 ml) under nitrogen, was slowly added boron tribromide (0.4 ml), then stirring was continued for a further 2 hours. Methanol (50 ml) was added carefully, then the solvent evaporated in vacuo to a volume of 1 ml; this was repeated 2 more times to give pure DC-0058 as a brown solid (143 mg, 77%).

$^1$H-NMR ((CD$_3$)$_2$CO) 9.62 (1H, bs), 6.95 (1H, d, J 2 Hz), 6.91 (1H, d, J 2 Hz), 6.88 (1H, d, J 8 Hz), 6.83 (1H, d, J 8 Hz), 6.67 (2H, m), 6.35 (4H, bs) 4.47 (2H, s) and 3.00 (4H, m).

M/z 302 ((M–H)$^+$, 100%)

HPLC (Method 2) 19.4 minutes.

Example 15

3,4-dihydroxycinnamic acid 3,4-dihydroxybenzylamide (compound 61; DC-0061)

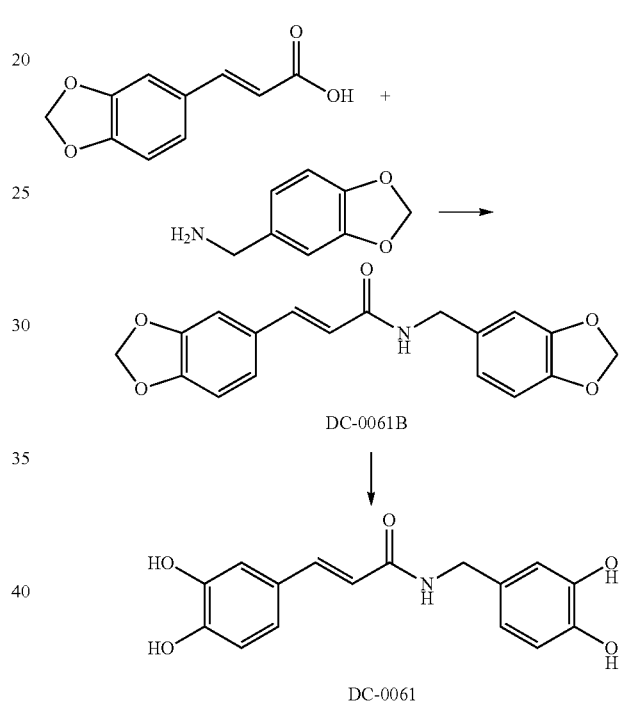

3,4-methylenedioxycinnamic acid 3,4-methylenedioxybenzylamide (compound 61B; DC-0061B)

To a solution of 3,4-methylenedioxycinnamic acid (0.5 g, 2.6 mmol) in dry CH$_2$Cl$_2$ (25 ml) under nitrogen, was added oxalyl chloride (0.33 g, 2.6 mmol) with three drops of dry DMF and the mixture was stirred for 1 hour. Solvents were removed in vacuo giving the acid chloride as a yellow solid. To a solution of the acid chloride in dry CH$_2$Cl$_2$ (50 ml) under nitrogen, cooled to 0° C., was added dropwise, a solution of 3,4-(methylenedioxy)benzylamine (0.393 g, 2.6 mmol) and pyridine (0.205 g, 2.6 mmol in CH$_2$Cl$_2$ (5 ml). The reaction mixture was stirred for 30 minutes at room temperature, diluted with CH$_2$Cl$_2$ (100 ml), washed with aqueous HCl (100 ml, 10%) and sodium bicarbonate solution (100 ml) then dried and evaporated in vacuo to give DC-0061B as a dull yellow powder (0.523 g, 62%).

$^1$H-NMR (CDCl$_3$) 7.58 (1H, d, J 16 Hz), 6.98 (2H, m), 6.70-6.84 (4H, m), 6.22 (1H, d, J 16 Hz), 6.00 (2H, s), 5.96 (2H, s) and 4.47 (2H, d, J 6 Hz).

M/z 326 ((M+1)⁺, 100%)

3,4-dihydroxycinnamic acid 3,4-dihydroxybenzylamide (compound 61; DC-0061)

To a stirred solution of DC-0061B (0.3 g, 0.94 mmol) dissolved in dry CH$_2$Cl$_2$ (25 ml) was slowly added boron tribromide (1.16 g, 4.6 mmol), then stirring continued for a further 12 hours. Dilute HCl (25 ml) was carefully added, then 200 ml of water, and the product was extracted into ethyl acetate (2×100 ml), dried and evaporated in vacuo to give the crude product. Purification by column chromatography eluting with hexane/ethyl acetate (1:4) gave DC-0061 as an off-white solid (36 mg, 13%).

$^1$H-NMR ((CD$_3$)$_2$CO) 7.54 (1H, d, J 16 Hz), 7.12 (1H, d, J 2 Hz), 6.96 (1H, dd, J 2, 8 Hz), 6.85-6.94 (2H, m), 6.80 (1H, d, J 8 Hz), 6.70 (1H, dd, J 2, 8 Hz), 6.58 (1H, d, J 16 Hz) and 4.41 (2H, s).

M/z 300 ((M−1)⁺, 100%)
HPLC (method 2) 30.0 minutes.

Example 16

Oxalic acid bis(3,4-dihydroxyanilide) (compound 63; DC-0063)

Method 1—Via Methylenedioxy-Protected Compounds

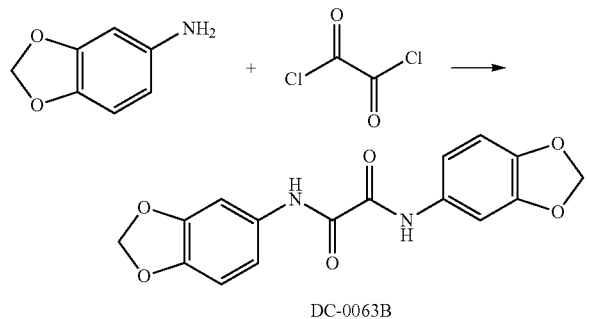

DC-0063B

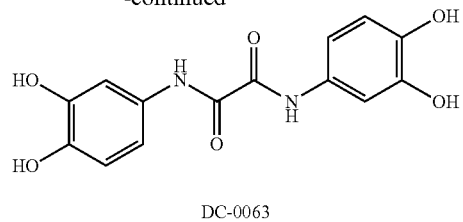

DC-0063

Oxalic acid bis(3,4-methylenedioxyanilide) (compound 63B; DC-0063B)

To a solution of oxalyl chloride (165 mg, 1.3 mmol) in dry CH$_2$Cl$_2$ (50 ml) under nitrogen, cooled to 0° C., was added dropwise, a solution of 3,4-(methylenedioxy)aniline (400 mg, 2.92 mmol) and pyridine (230 mg, 2.92 mmol) dissolved in dry CH$_2$Cl$_2$ (50 ml). The reaction mixture was stirred for further 30 min at room temperature, then washed with dilute aqueous HCl (50 ml). The organic layer was separated, dried and evaporated in vacuo to give DC-0063B as a gray powder (0.351 g, 82%).

$^1$H-NMR (CDCl$_3$) 10.78 (2H, s), 7.53 (2H, d, J 2 Hz), 7.39 (2H, dd, J 2, 8 Hz), 6.96 (2H, d, J 8 Hz) and 6.06 (4H, s).

Oxalic acid bis(3,4-dihydroxyanilide) (compound 63: DC-0063)

To a stirred solution of DC-0063B (0.3 g, 0.91 mmol) dissolved in dry CH$_2$Cl$_2$ (25 ml) was slowly added boron tribromide (1.14 g, 4.7 mmol) then stirring continued for a further 4 hours. Dilute HCl (25 ml) was carefully added, then water (200 ml) and the product extracted into ethyl acetate (2×200 ml), dried and evaporated in vacuo to give the crude product. The crude product was dissolved in acetone (25 ml) and filtered. The acetone was evaporated in vacuo to give DC-0063 as an off-white solid (171 mg, 62%).

$^1$H-NMR ((CD$_3$)$_2$CO) 9.72 (2H, br s), 8.05 (2H, br s), 7.89 (2H, br s), 7.52 (2H, d, J 2 Hz), 7.20 (2H, dd, J 2, 8 Hz) and 6.83 (2H, d, J 8 Hz).

M/z 303 ((M−1)⁺, 100%)
HPLC (method 2) 29.1 minutes.

Method 2—Via Methoxymethoxy-Protected Compounds

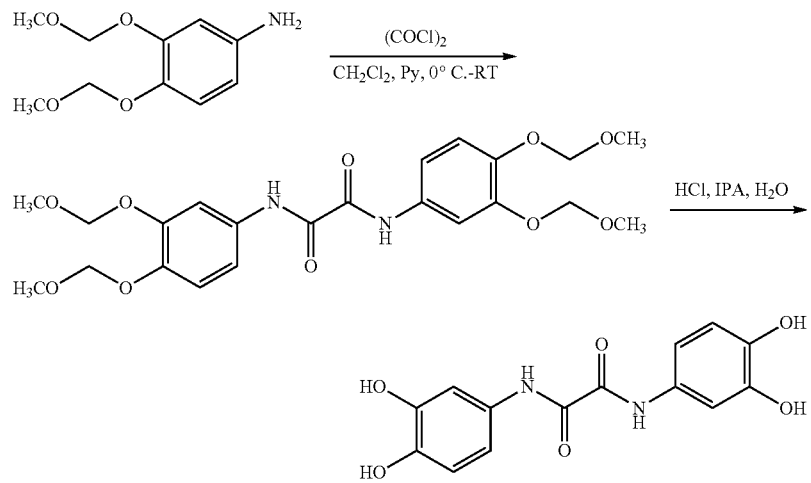

Oxalic acid bis(3,4-di(methoxymethoxy)anilide)

3,4-di(methoxymethoxy)aniline (1.5 g, 7 mmol) was dissolved in dichloromethane (50 ml) and cooled to 0° C., while stirring under nitrogen. Pyridine (3.75 ml, 46 mmol) was added followed by dropwise addition of oxalyl chloride (0.4 g, 3.5 mmol) in dichloromethane (5 ml) over 20 minutes. The reaction was stirred for a further 10 min and allowed to warm to room temperature. The suspension was filtered. The residue was washed with hexane (5 ml) to remove excess pyridine. The crude product was triturated with methanol (5 ml) and filtered to afford the pure protected anilide, 420 mg.

Oxalic acid bis(3,4-dihydroxyanilide)

Oxalic acid bis(3,4-di(methoxymethoxy)anilide) (0.17 g, 0.36 mmol) was combined with a 25% solution of hydrogen chloride in isopropyl alcohol (1.7 ml). The reaction was stirred at room temperature overnight, and the solvent was removed under reduced pressure. Trituration with diethyl ether (5 ml) afforded DC-0063, 60 mgs.

Example 17

Succinic acid bis(3,4-dihydroxyanilide) (compound 66; DC-0066)

Method 1—Via Methylenedioxy-Protected Compounds

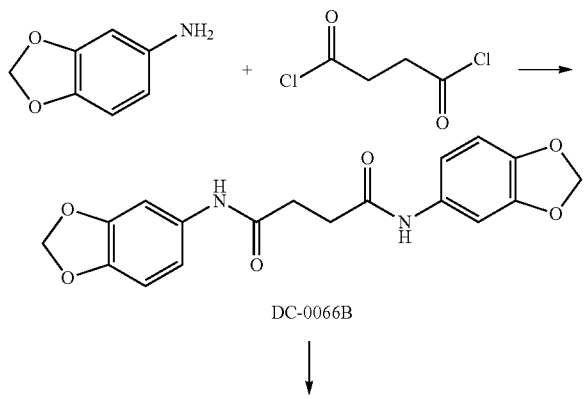

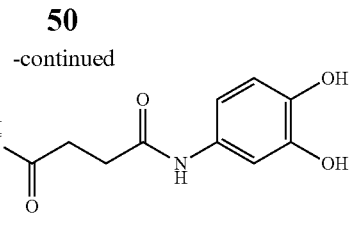

DC-0066

Succinic acid bis(3,4-methylenedioxyanilide) (compound 66B; DC-0066B)

To a suspension of succinic acid (200 mg, 1.7 mmol) in dry $CH_2Cl_2$ (25 ml) under nitrogen was added oxalyl chloride (645 mg, 5.08 mmol) with three drops of dry DMF, and the mixture was stirred for 1 hour. Solvents were removed in vacuo giving the acid chloride as a yellowish solid. To a stirred solution of 3,4-(methylenedioxy)aniline (582 mg, 4.25 mmol) and pyridine (400 mg, 5.08 mmol) in dry $CH_2Cl_2$ (50 ml) under nitrogen at 0° C. was added drop-wise a solution of the acid chloride in dry $CH_2Cl_2$ (25 ml) and stirred for a further 2 hours. The solvents were removed in vacuo to give the crude product. The crude material was resuspended in EtOAc (250 ml) then washed with dilute aqueous HCl (2×150 ml), saturated sodium bicarbonate (2×150 ml) and water (1×150 ml). The EtOAc was then removed by rotary evaporation. The product was scooped out onto filter paper and washed with water and allowed to dry to give DC-0066B as a white solid (514 mg, 78%).

$^1$H-NMR ($CDCl_3$) 9.97 (2H, s), 7.34 (2H, d, J 2 Hz), 6.99 (2H, dd, J 2, 8 Hz), 6.86 (2H, d, J 8 Hz), 6.00 (4H, s) and 2.63 (4H, s).

Succinic acid bis(3,4-dihydroxyanilide) (compound 66; DC-0066)

To a stirred solution of DC-0066B (0.3 g, 0.78 mmol) in dry $CH_2Cl_2$ (25 ml) was slowly added $BBr_3$ (0.978 g, 3.9 mmol) then stirring continued for a further 4 hours. Dilute HCl (25 ml) was carefully added, then 200 ml of water and the product extracted into ethyl acetate (2×100 ml), dried and evaporated in vacuo to give DC-0066 as an off white solid (97 mg, 35%).

$^1$H-NMR (($CD_3$)$_2$CO) 8.88 (2H, br s), 7.83 (2H, br s), 7.57 (2H, br s), 7.34 (2H, d, J 2 Hz), 6.90 (2H, dd, J 2, 8 Hz), 6.71 (2H, d, J 8 Hz) and 2.65 (4H, s).

M/z 331 ((M−1)$^+$, 100%)

HPLC (method 2) 10.6 minutes.

Method 2—Via Methoxymethoxy-Protected Compounds

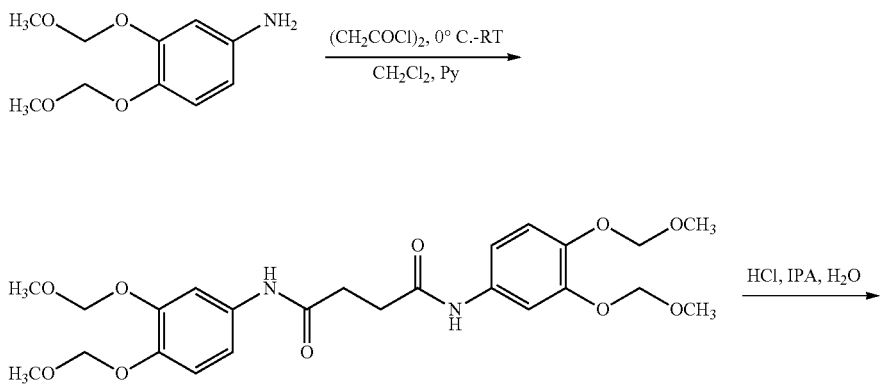

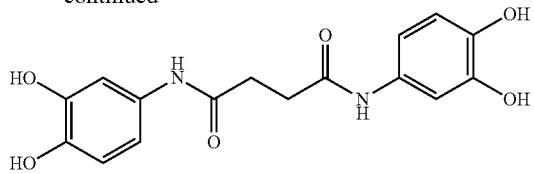

Succinic acid bis(3,4-di(methoxymethoxy)anilide)

3,4-di(methoxymethoxy)aniline (1 g, 4.7 mmol) was dissolved in dichloromethane (25 ml) and cooled to 0° C., while stirring under nitrogen. Pyridine (1 ml, 12 mmol) was added followed by dropwise addition of succinyl chloride (0.35 g, 2.3 mmol) in dichloromethane (10 ml) over 20 minutes. The reaction was stirred for a further 2 hours and allowed to warm to room temperature. The suspension was filtered, and the white solid collected washed with hexane (10 ml) and then methanol (4 ml) to afford the anilide, 350 mg.

Succinic acid bis(3,4-dihydroxyanilide) (compound 66; DC-0066)

Succinic acid bis(3,4-di(methoxymethoxy)anilide) (0.15 g, 0.3 mmol) was combined with a 25% solution of hydrogen chloride in isopropyl alcohol (1.5 ml) and water (1.5 ml). The reaction was stirred at room temperature for 3 h and the solvent was removed under reduced pressure. Trituration with diethyl ether afforded DC-0066 as a solid which was dried under vacuum at 30° C., yield 60 mg.

Example 18

Succinic acid bis(3,4-dihydroxybenzylamide) (compound 67; DC-0067)

Method 1—Via Methylenedioxy-Protected Compounds

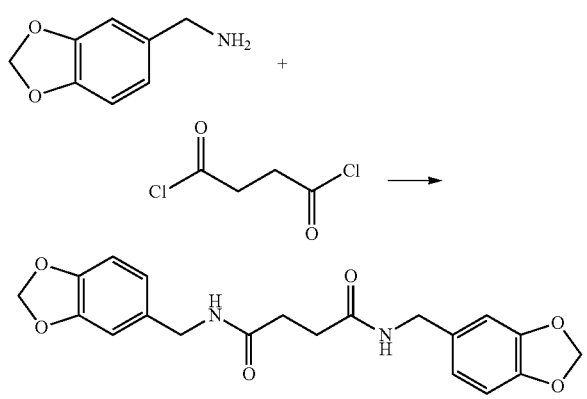

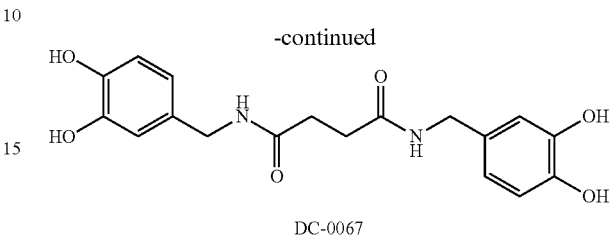

Succinic acid bis(3,4-methylenedioxybenzylamide) (compound 67B; DC-0067B)

To a solution of succinic acid (200 mg, 1.7 mmol) in dry $CH_2Cl_2$ (25 ml) under nitrogen, was added oxalyl chloride (645 mg, 5.1 mmol) with three drops of dry DMF and the mixture was stirred for 1 hour. Solvents were removed in vacuo giving the acid chloride as a yellow solid. To a solution of the acid chloride in dry $CH_2Cl_2$ (50 ml) under nitrogen, cooled to 0° C., was added dropwise, a solution of 3,4-methylenedioxybenzylamine (634 mg, 4.2 mmol) and pyridine (0.33 ml) in $CH_2Cl_2$ (50 ml). The reaction mixture was stirred for a further 2 hours at room temperature, then the solvents removed in vacuo to give the crude product. The crude material was resuspended in EtOAc (250 ml) then washed with dilute aqueous HCl (2×150 ml), saturated sodium bicarbonate (2×150 ml) and water (1×150 ml). The EtOAc was evaporated in vacuo. Recrystallization from ethanol and water gave DC-0067B as white flaky crystals (275 mg, 42%).

$^1$H-NMR (DMSO-$d_6$) 8.31 (2H, t, J 6 Hz), 6.85 (4H, m), 6.74 (2H, dd, J 2, 8 Hz), 6.01 (4H, s), 4.19 (4H, d, J 6 Hz) and 2.42 (4H, s).

Succinic acid bis(3,4-dihydroxybenzylamide) (compound 67; DC-0067)

To a stirred solution of DC-0067B (0.25 g, 0.65 mmol) dissolved in dry $CH_2Cl_2$ (25 ml) was slowly added boron tribromide (0.81 g, 0.31 ml), then stirring continued for a further 4 hours. Dilute HCl (25 ml) was carefully added, then brine (125 ml) and the product extracted into ethyl acetate (2×100 ml), dried and evaporated in vacuo to give DC-0067 as an off-white solid (180 mg, 77%).

$^1$H-NMR ((CD$_3$)$_2$CO) 7.90 (2H, br s), 7.74 (2H, br s), 7.42 (2H, br s), 6.79 (2H, d, J 2 Hz), 6.77 (2H, d, J 8 Hz), 6.62 (2H, dd, J 2, 8 Hz), 4.22 (4H, d, J 7 Hz) and 2.53 (4H, s).

M/z 359 ((M−1)$^+$, 100%).

HPLC (method 2) 12.3 minutes.

Method 2—Via Benzyloxy-Protected Compounds

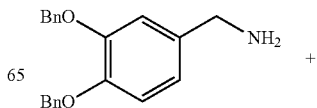

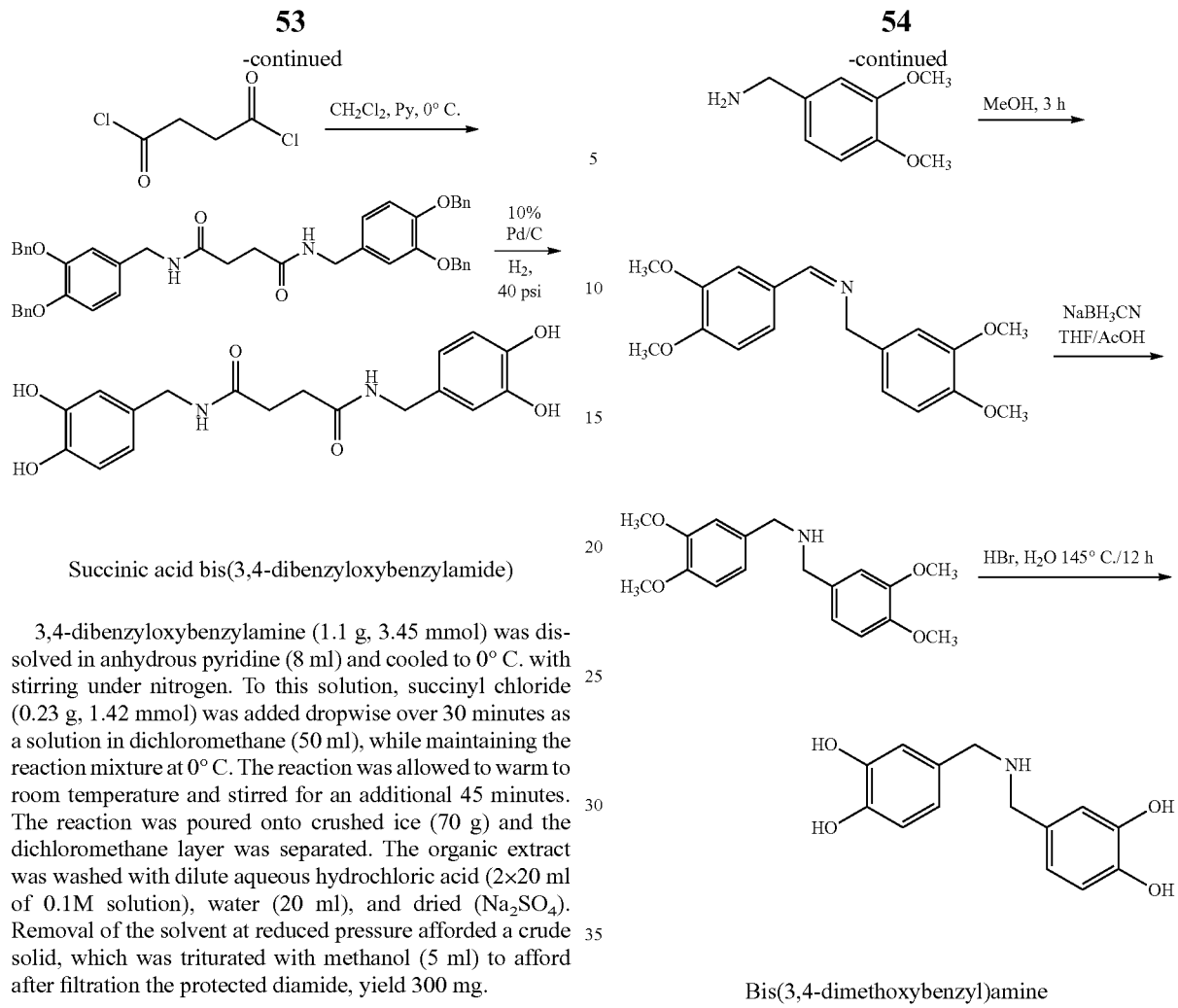

Succinic acid bis(3,4-dibenzyloxybenzylamide)

3,4-dibenzyloxybenzylamine (1.1 g, 3.45 mmol) was dissolved in anhydrous pyridine (8 ml) and cooled to 0° C. with stirring under nitrogen. To this solution, succinyl chloride (0.23 g, 1.42 mmol) was added dropwise over 30 minutes as a solution in dichloromethane (50 ml), while maintaining the reaction mixture at 0° C. The reaction was allowed to warm to room temperature and stirred for an additional 45 minutes. The reaction was poured onto crushed ice (70 g) and the dichloromethane layer was separated. The organic extract was washed with dilute aqueous hydrochloric acid (2×20 ml of 0.1M solution), water (20 ml), and dried ($Na_2SO_4$). Removal of the solvent at reduced pressure afforded a crude solid, which was triturated with methanol (5 ml) to afford after filtration the protected diamide, yield 300 mg.

Succinic acid bis(3,4-dihydroxybenzylamide) (compound 67; DC-0067)

Succinic acid bis(3,4-dibenzyloxybenzylamide) (300 mg, 0.42 mmol) was dissolved in THF (50 ml) in a pressure bottle and warmed to 35 C to ensure dissolution of the solid. Palladium on carbon (50 mg 10% Pd/C) was added, and the vessel was pressurized with hydrogen (to 3 atm). The reaction was agitated for 1 hour at room temperature, whereupon TLC revealed reaction had gone to completion. The catalyst was removed by filtration, and the solvent removed under reduced pressure to afford DC-0067 as a crude solid (20 mg). This material was recrystallized from toluene and methanol to afford DC-0067.

Example 19

Bis(3,4-dihydroxybenzyl)amine (compound 73; DC-0073)

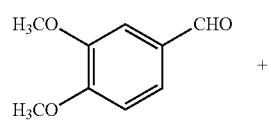

To a solution of 3,4-dimethoxybenzaldelyde (1 g, 6 mmol) in anhydrous methanol (10 ml) was added 3,4-dimethoxybenzylamine (1 g, 5.9 mmol) and the solution stirred under nitrogen at room temperature for 3 hours. The methanol was removed under reduced pressure to afford the crude imine, 1.9 g. The imine was dissolved in THF (10 ml) and acetic acid (4 ml), and sodium cyanoborohydride (0.38 g, 6 mmol) was added portionwise over 30 minutes. The solution was stirred for an additional 30 minutes at room temperature, and the solvents were removed under reduced pressure. The residue was neutralized with saturated aqueous sodium hydrogen carbonate, and the solid crude product was isolated by filtration, and dried under vacuum at 50° C. overnight, yield 0.6 g.

Bis(3,4-dihydroxybenzyl)amine (compound 73; DC-0073)

The crude bis(3,4-dimethoxybenzyl)amine (0.6 g) was combined with hydrobromic acid (6 ml of 48% w/w solution in water) and slowly heated with stirring, to 145° C. over 1 h. The reaction was maintained at 145° C. for 12 h, allowed to cool to room temperature, and poured into water (25 ml). The reaction mixture was neutralized with saturated aqueous sodium hydrogen carbonate, and extracted with ethyl acetate (25 ml). The organic layer was washed into water (2×25 ml), dried ($Na_2SO_4$) and the solvent removed under reduced pressure to afford DC-0073 as a solid, 160 mg.

Example 20

Tris(3,4-dihydroxybenzyl)amine (compound 75; DC-0075)

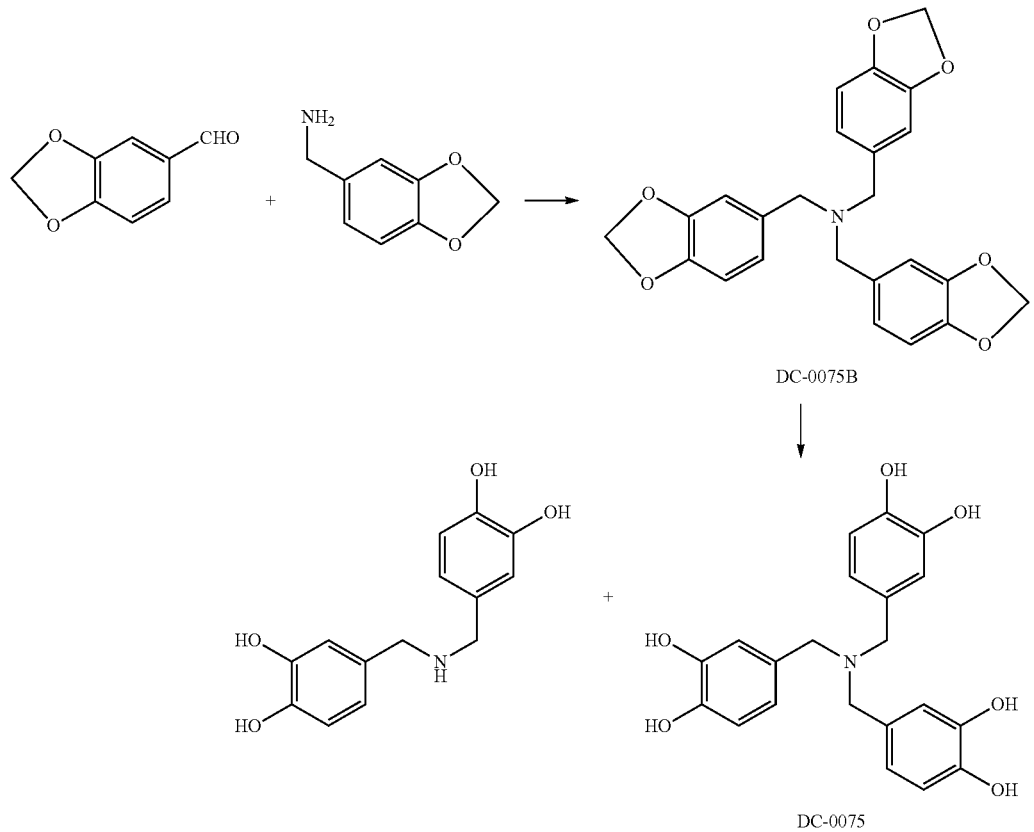

Tris(3,4-methylenedioxybenzyl)amine (compound 75B; DC-0075B)

To a stirred solution of piperonal (0.9 g, 6 mmol) and ammonium acetate (0.15 g, 2 mmol) in acetonitrile (25 ml) was added sodium cyanoborohydride (0.44 g, 7 mmol) and the mixture was stirred for 4 days. The solvent was removed in vacuo, then the residue dissolved in dichloromethane (100 ml) and washed with sat. sodium bicarbonate, dried and the solvent removed in vacuo to give a brown gum. Purification by column chromatography over silica gel eluting with 50% dichloromethane in hexane gave the pure DC-0075B as a pale brown gum (135 mg, 5%).

$^1$H-NMR (CDCl$_3$) 6.91 (3H, m), 6.73-6.80 (6H, m), 5.94 (6H, s) and 3.42 (2H, m)

M/z 420 ((M+1)$^+$, 100%).

Tris(3,4-dihydroxybenzyl)amine (compound 75; DC-0075)

To a stirred solution of DC-0075B (135 mg) in dry CH$_2$Cl$_2$ (20 ml) under nitrogen, was slowly added boron tribromide (0.2 ml) then stirring continued for a further 2 hours. Methanol (50 ml) was added carefully, then the solvent evaporated in vacuo to a volume of 1 ml, this addition and evaporation was repeated twice more. Purification by column chromatography over silica gel eluting with 20% methanol in chloroform gave mostly pure DC-0075 (72 mg, 58%) as a pale brown gum. Preparative HPLC then gave the pure DC-0075 as a white gum (26 mg, 21%).

$^1$H-NMR (CD$_3$OD) 6.82-6.86 (2H, m), 6.74 (1H, dd, J 2, 8 Hz) and 4.07 (2H, s).

M/z 384 ((M+1)$^+$, 100%).

HPLC (method 2) 12.3 minutes.

Example 21

1,3-Bis(3,4-dihydroxyphenyl)urea (compound 76; DC-0076)

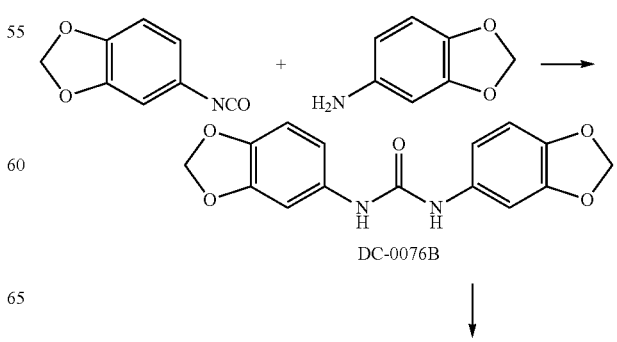

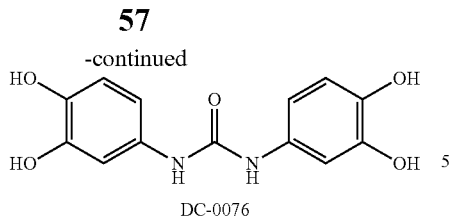
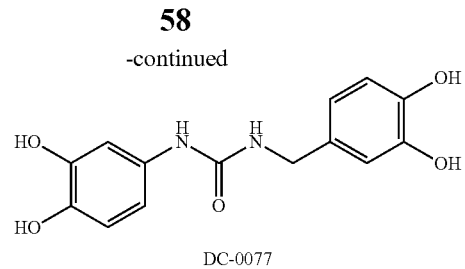

1,3-Bis(3,4-methylenedioxyphenyl)urea (compound 67B; DC-0076B)

A solution of 3,4-methylenedioxyaniline (0.35 g) and 3,4-methylenedioxyphenyl isocyanate (0.4 g) in benzene (25 ml) was refluxed for 1 hour. The precipitate formed was filtered, washed with benzene then dried to give pure DC-0076B (0.697 g, 95%) as a pale brown solid.

$^1$H-NMR (CDCl$_3$/(CD$_3$)$_2$CO) 7.35 (2H, bs), 6.93 (2H, s), 6.45 (4H, s) and 5.67 (4H, s).

1,3-Bis(3,4-dihydroxyphenyl)urea (compound 76; DC-0076)

To a stirred solution of DC-0076B (150 mg) in dry CH$_2$Cl$_2$ (20 ml) under nitrogen, was slowly added boron tribromide (0.2 ml) then stirring continued for a further 2 hours. Methanol (50 ml) was added carefully, then the solvent evaporated in vacuo to a volume of 1 ml, and this addition and evaporation was repeated twice more. Purification by column chromatography over silica gel eluting with 20% methanol in chloroform gave pure DC-0076 (113 mg, 82%) as a pale brown solid.

$^1$H-NMR (D$_2$O/(CD$_3$)$_2$CO) 7.09 (2H, d, J 2 Hz), 6.76 (2H, d, J 8 Hz) and 6.70 (2H, dd, J 2, 8 Hz).

M/z 551 ((2M−H)$^+$, 100%), 275 ((M−H)$^+$, 85%).

HPLC (Method 2) 5.8 min.

Example 22

1-(3,4-dihydroxyphenyl)-3-(3,4-dihydroxybenzyl)urea (DC-0077)

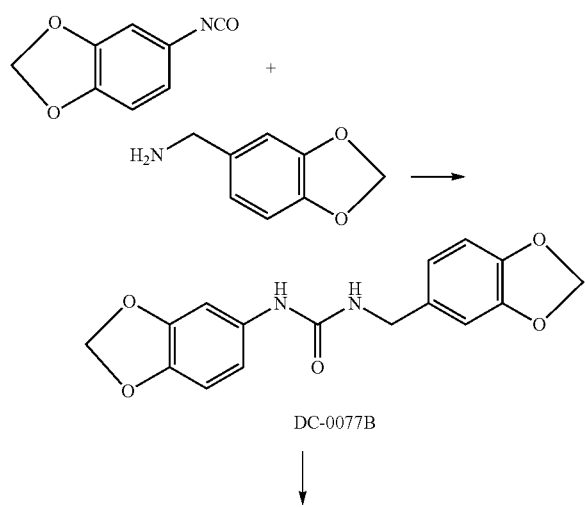

1-(3,4-methylenedioxyphenyl)-3-(3,4-methylenedioxybenzyl)urea (DC-0077B)

A solution of 3,4-methylenedioxybenzylamine (0.37 g) and 3,4-methylenedioxyphenyl isocyanate (0.4 g) in benzene (25 ml) was refluxed for 1 hour. The precipitate formed was filtered, washed with benzene then dried to give pure DC-0077B (0.78 g, 98%) as a pale brown solid.

$^1$H NMR (CDCl$_3$) 8.42 (1H, s, NH), 7.21 (1H, d, J 2 Hz), 6.88 (2H, m), 6.79 (2H, m), 6.71 (1H, dd, J 2, 8 Hz), 6.49 (1H, t, J 6 Hz, NH), 6.01 (2H, s), 5.97 (2H, s) and 4.21 (2H, d, J 6 Hz).

M/z 315 ((M+1)$^+$, 100%).

1-(3,4-dihydroxyphenyl)-3-(3,4-dihydroxybenzyl)urea (DC-0077)

To a stirred solution of DC-0077B (200 mg) in dry CH$_2$Cl$_2$ (50 ml) under nitrogen, was slowly added boron tribromide (0.4 ml) then stirring continued for a further 3 hours. Methanol (50 ml) was added carefully, then the solvent evaporated in vacuo to a volume of 1 ml, this was repeated 2 more times. Purification by column chromatography over silica gel eluting with 20% methanol in chloroform gave a fraction containing crude product. Preparative HPLC gave pure DC-0077 (19 mg, 11%) as a pale brown solid.

$^1$H NMR (D$_2$O) 6.55-6.80 (6H, m) and 4.12 (2H, s).

M/z 290 ((M)$^+$, 100%).

HPLC (method 2) 12.7 min.

Example 23

1-(3,4-Dihydroxyphenyl)-3-(3,4-dihydroxyphenethyl)urea (compound 78; DC-0078)

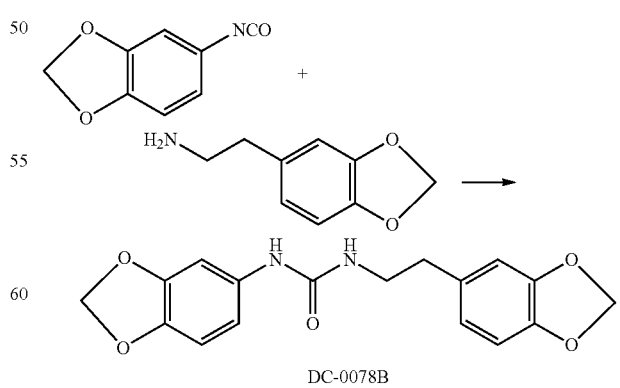

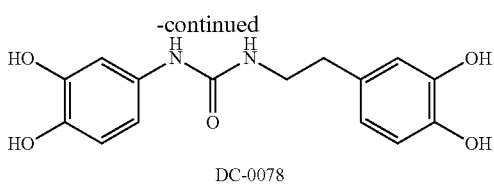

DC-0078

1-(3,4-methylenedioxyphenyl)-3-(3,4-methylene-dioxyphenethyl)urea (compound 78B; DC-0078B)

A solution of 3,4-methylenedioxyphenylethylamine (0.25 g, 1.5 mmol) and 3,4-methylenedioxy-phenyl isocyanate (0.25 g, 1.5 mmol) in benzene (25 ml) was refluxed for 1 hour. The precipitate formed was filtered, washed with benzene then dried to give pure DC-0078B (0.43 g, 85%) as a pale brown solid.

$^1$H-NMR ((CD$_3$)$_2$CO) 7.83 (1H, bs), 7.31 (1H, d, J 2 Hz), 6.72-6.82 (5H, m), 5.99 (2H, s), 5.95 (2H, s), 5.68 (1H, bt, J 7 Hz), 3.44 (2H, q, J 7 Hz), and 2.74 (2H, t, J 7 Hz).

M/z 327 ((M−1)$^+$, 100%).

1-(3,4-dihydroxyphenyl)-3-(3,4-dihydroxyphenethyl)urea (compound 78: DC-0078)

To a stirred solution of DC-0078B (105 mg) in dry CH$_2$Cl$_2$ (20 ml) under nitrogen, was slowly added boron tribromide (0.2 ml), then stirring continued for a further 2 hours. Methanol (50 ml) was added carefully, then the solvent evaporated in vacuo to a volume of 1 ml; this addition and evaporation was repeated twice more. Purification by column chromatography over silica gel eluting with 20% methanol in chloroform gave pure DC-0078 (78 mg, 80%) as a pale brown solid.

$^1$H-NMR ((CD$_3$)$_2$CO) 6.97 (2H, m), 6.86-6.89 (3H, m), 6.68 (1H, dd, J 2, 8 Hz), 3.66 (2H, t, J 7 Hz), and 2.87 (2H, t, J 7 Hz).

M/z 303 ((M−1)$^+$, 100%).

HPLC (method 2) 33.7 min.

Example 24

Dibenzo[c,f][2,7]naphthyridine-2,3,10,11-tetraol (compound 85; DC-0085)

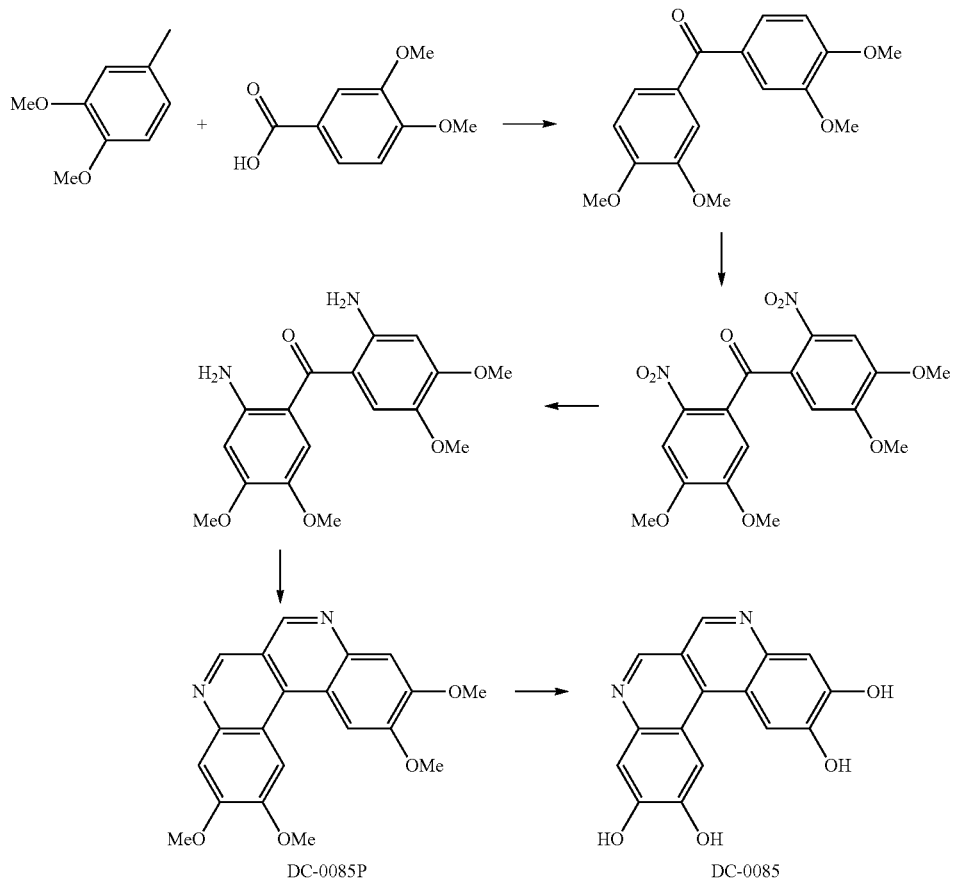

2,3,10,11-Tetramethoxydibenzo[c,f][2,7]naphthyridine (DC-0085P)

DC-0085P was prepared as described by Upton et al., *J. Pharm. Pharmacol.*, 50(5):475-482, 1998. Veratrole was reacted with veratric acid to give the protected benzophenone, which was nitrated to give the dinitro compound, and this was reduced to the diamine by treatment with tin in hydrochloric acid and acetic acid. The diamine was isolated, and then condensed with malonaldehyde bis(dimethyl acetal) to give DC-0085P.

Dibenzo[c,f][2,7]naphthyridine-2,3,10,11-tetraol
(DC-0085)

To a stirred solution of DC-0085P (100 mg) in dry $CH_2Cl_2$ (20 ml) under nitrogen, was slowly added boron tribromide (0.2 ml), then stirring continued for a further 2 hours. Methanol (50 ml) was added carefully, then the solvent evaporated in vacuo to a volume of 1 ml, and this addition and evaporation was repeated twice more. Purification by crystallization from methanol/chloroform gave DC-0085 (36 mg, 38%) as an orange crystalline solid.

$^1$H-NMR ($CD_3OD$) 9.63 (2H, s), 8.63 (2H, s) and 7.64 (2H, s).

M/z 296 (($M+2$)$^+$, 100%)

HPLC (method 1) 24.3 min.

Example 25

Compounds of this Invention are Potent Disrupters of Alzheimer's Aβ 1-42 Fibrils The compounds prepared in the preceding Examples were found mostly to be potent disruptors/inhibitors of Alzheimer's disease β-amyloid protein (Aβ) fibrils. In a set of studies, the efficacy of the compounds to cause a disassembly/disruption of pre-formed amyloid fibrils of Alzheimer's disease (i.e. consisting of Aβ 1-42 fibrils) was analyzed.

Part A—Thioflavin T Fluorometry Data

In one study, Thioflavin T fluorometry was used to determine the effects of the compounds, and of EDTA (as a negative control). In this assay Thioflavin T binds specifically to fibrillar amyloid, and this binding produces a fluorescence enhancement at 485 nm that is directly proportional to the amount of amyloid fibrils formed. The higher the fluorescence, the greater the amount of amyloid fibrils formed (Naki et al., *Lab. Invest.* 65:104-110, 1991; Levine III, *Protein Sci.* 2:404-410, 1993; *Amyloid: Int. J. Exp. Clin. Invest.* 2:1-6, 1995).

In this study, 25 μM of pre-fibrillized Aβ 1-42 (Bachem Inc) was incubated at 37° C. for 3 days either alone, or in the presence of one of the compounds or EDTA (at Aβ:test compound weight ratios of 1:1, 1:0.1, 1:0.01 or 1:0.001). Following 3-days of co-incubation, 50 μl of each incubation mixture was transferred into a 96-well microtiter plate containing 150 μl of distilled water and 50 μl of a Thioflavin T solution (i.e. 500 mM Thioflavin T in 250 mM phosphate buffer, pH 6.8). The fluorescence was read at 485 nm (444 nm excitation wavelength) using an ELISA plate fluorometer after subtraction with buffer alone or compound alone, as blank.

The results of the 3-day incubations are presented below. For example, whereas EDTA caused no significant inhibition of Aβ 1-42 fibrils at all concentrations tested, the compounds all caused a dose-dependent disruption/disassembly of pre-formed Aβ 1-42 fibrils to some extent. The most efficacious compounds to disrupt pre-formed Aβ 1-42 fibrils appeared to be compounds #3, 4, 21, 51, 73 and 78. For example, compound #4 caused a significant (p<0.01) 97.4±0.40% inhibition when used at an Aβ:test compound wt/wt ratio of 1:0.1, and a 69.4±1.17% disruption when used at an Aβ:compound wt/wt ratio of 1:0.01. Under the same conditions (i.e. Aβ:test compound wt/wt ratio of 1:0.1), compound #3 caused an 57.8±6.36% disruption, compound #21 caused a 81.0±1.31% disruption, compound #51 caused 94.9±0.24% disruption, compound #73 caused a 70.9±3.04% disruption, and compound #78 caused a 89.7±1.8% disruption. This study indicated that the compounds of this invention are potent disruptors/inhibitors of Alzheimer's disease type Aβ fibrils, and usually exert their effects in a dose-dependent manner.

TABLE 1

Thioflavin T fluorometry data - disruption of Aβ 1-42 Alzheimer's fibrils
% Inhibition Aβ (result ± S.D.) at Aβ:test compound wt/wt ratio given

| Test Compound # | 1:1 | 1:0.1 | 1:0.01 | 1:0.001 |
|---|---|---|---|---|
| EDTA (control) | 11.3 ± 9.67 | 0.0 ± 7.12 | 0.0 ± 4.88 | 0.0 ± 3.01 |
| 1 | 97.3 ± 0.23 | 64.8 ± 1.98 | 19.2 ± 4.31 | 0.0 ± 3.07 |
| 3 | 99.5 ± 0.10 | 57.8 ± 6.36 | 53.1 ± 1.67 | 5.5 ± 1.99 |
| 4 | 98.5 ± 0.77 | 97.4 ± 0.40 | 69.4 ± 1.17 | 26.8 ± 4.80 |
| 8 | 70.8 ± 2.57 | 65.5 ± 0.17 | 24.7 ± 3.51 | 4.9 ± 2.27 |
| 9 | 95.1 ± 0.13 | 34.9 ± 1.69 | 2.0 ± 10.75 | 10.6 ± 0.93 |
| 12 | 99.7 ± 0.17 | 82.0 ± 1.13 | 10.8 ± 21.9 | 0.0 ± 34.9 |
| 19 | 99.1 ± 0.56 | 91.1 ± 0.66 | 46.2 ± 2.98 | 10.8 ± 1.38 |
| 21 | 98.6 ± 0.54 | 81.0 ± 1.31 | 48.2 ± 8.29 | 8.9 ± 2.13 |
| 23 | 46.7 ± 4.62 | 26.2 ± 4.37 | 16.5 ± 4.02 | 0.0 ± 3.72 |
| 26 | 37.8 ± 5.50 | 11.7 ± 3.67 | 0.0 ± 2.19 | 0.0 ± 3.24 |
| 51 | 99.4 ± 0.05 | 94.9 ± 0.24 | 55.3 ± 5.23 | 29.0 ± 25.2 |
| 52 | 93.7 ± 0.41 | 53.6 ± 2.42 | 12.1 ± 0.78 | 0.0 ± 6.67 |
| 57 | 88.4 ± 2.73 | 60.2 ± 3.12 | 19.0 ± 6.33 | 17.7 ± 7.43 |
| 58 | 94.8 ± 1.67 | 76.0 ± 2.57 | 33.2 ± 5.16 | 20.5 ± 6.27 |
| 61 | 100.0 ± 0.41 | 80.1 ± 4.76 | 16.9 ± 1.39 | 26.0 ± 7.51 |
| 63 | 85.3 ± 0.91 | 23.6 ± 25.75 | 57.5 ± 10.64 | 1.6 ± 9.47 |
| 66 | 100.0 ± 0.68 | 78.3 ± 4.17 | 42.0 ± 2.36 | 27.1 ± 3.51 |
| 67 | 98.3 ± 2.19 | 50.9 ± 8.32 | 34.0 ± 14.07 | 13.7 ± 6.05 |
| 73 | 99.4 ± 0.42 | 70.9 ± 3.04 | 28.7 ± 10.27 | 0.0 ± 29.43 |
| 75 | 99.0 ± 0.63 | 84.4 ± 0.94 | 31.6 ± 4.74 | 17.0 ± 4.20 |
| 76 | 99.3 ± 1.35 | 86.5 ± 1.18 | 40.9 ± 3.76 | 12.2 ± 5.98 |
| 78 | 100 ± 0.78 | 89.7 ± 1.18 | 57.8 ± 4.63 | 22.4 ± 5.63 |

Part B: SDS-PAGE/Western Blot Data

The disruption of Aβ 1-42, even in its monomeric form, was confirmed by a study involving the use of SDS-PAGE and Western blotting methods (not shown). In this latter study, triplicate samples of pre-fibrillized Aβ 1-42 (25 μM) was incubated at 37° C. for 3 days, alone or in the presence of the compounds or EDTA. Five micrograms of each sample was then filtered through a 0.2 μm filter. Protein recovered from the filtrate was then loaded, and ran on a 10-20% Tris-Tricine SDS-PAGE, blotted to nitrocellulose and detected using an Aβ-antibody (clone 6E10; Senetek). In this study, Aβ 1-42 was detected as a ~4 kilodalton band (i.e. monomeric Aβ) following incubation alone, or in the presence of EDTA, at 3 days. For example, Aβ 1-42 monomers were not detected following incubation of Aβ 1-42 with compounds 4, 19, 21, 51, 58, 66, 75, 76 and 78 suggesting that these compounds were capable of causing a disappearance of monomeric Aβ 1-42. This study confirmed that these compounds are also capable of causing a disruption/removal of monomeric Aβ 1-42.

Part C: Congo Red Binding Data

In the Congo red binding assay the ability of a test compound to alter amyloid (in this case, Aβ) binding to Congo red is quantified. In this assay, Aβ 1-42 and test compounds were incubated for 3 days and then vacuum filtered through a 0.2 μm filter. The amount of Aβ 1-42 retained in the filter was then quantitated following staining of the filter with Congo red. After appropriate washing of the filter, any lowering of the Congo red color on the filter in the presence of the test compound (compared to the Congo red staining of the amyloid protein in the absence of the test compound) was indicative of the test compound's ability to diminish/alter the amount of aggregated and congophilic A.

In one study, the ability of Aβ fibrils to bind Congo red in the absence or presence of increasing amounts of the compounds or EDTA (at Aβ:test compound weight ratios of 1:1, 1:0.1, 1:0.01 or 1:0.001) was determined. The results of 3-day incubations are presented in Table 2 below. Whereas EDTA caused no significant inhibition of Aβ 1-42 fibril binding to Congo red at all concentrations tested, the compounds caused a dose-dependent inhibition of Aβ binding to Congo red. For example, compound #4 caused a significant (p<0.01) 73.0±0.90% inhibition of Congo red binding to Aβ 1-42 fibrils when used at an Aβ:test compound wt/wt ratio of 1:1, and a significant (p<0.01) 46.8±1.28% inhibition of Congo red binding when used at an Aβ:test compound wt/wt ratio of 1:0.1, and a significant (p<0.01) 16.4±2.02% inhibition of Congo red binding when used at an Aβ:test compound wt/wt ratio of 1:0.01. In another example, synthetic analog compound #3 caused a significant (p<0.01) 91.6±5.19% inhibition of Congo red binding to Aβ 1-42 fibrils when used at an Aβ:test compound wt/wt ratio of 1:1, and a significant (p<0.01) 35.7±3.29% inhibition of Congo red binding when used at an Aβ:test compound wt/wt ratio of 1:0.01. This study also indicated that compounds of this invention are potent inhibitors of Aβ fibril binding to Congo red, and usually exert their effects in a dose-dependent manner.

TABLE 2

Congo red binding data
% Inhibition Aβ (result ± S.D.) at Aβ:test compound wt/wt ratio given

| Test Compound # | 1:1 | 1:0.1 | 1:0.01 | 1:0.001 |
|---|---|---|---|---|
| EDTA (control) | 1.1 ± 7.02 | 3.6 ± 8.68 | 0.0 ± 3.91 | 7.91 ± 3.61 |
| 1 | 42.4 ± 1.58 | 8.0 ± 1.80 | 3.9 ± 0.66 | 0.0 ± 3.54 |
| 3 | 91.6 ± 5.19 | 35.7 ± 3.29 | 7.4 ± 1.51 | 1.7 ± 4.21 |
| 4 | 73.0 ± 0.90 | 46.8 ± 1.28 | 16.4 ± 2.02 | 2.3 ± 1.80 |
| 8 | 17.7 ± 1.86 | 9.7 ± 0.69 | 1.1 ± 0.96 | 0.0 ± 3.55 |
| 9 | 46.8 ± 1.50 | 10.9 ± 2.18 | 0.0 ± 2.15 | 3.1 ± 3.66 |
| 12 | 63.0 ± 1.63 | 20.8 ± 2.22 | 17.9 ± 7.33 | 4.1 ± 6.60 |
| 19 | 48.1 ± 2.00 | 22.4 ± 2.19 | 7.4 ± 2.20 | 0.0 ± 1.01 |
| 21 | 66.2 ± 1.26 | 33.9 ± 1.02 | 9.3 ± 5.68 | 3.6 ± 0.58 |
| 23 | 10.7 ± 2.84 | 2.9 ± 0.43 | 0.0 ± 0.72 | 12.3 ± 6.57 |
| 26 | 4.5 ± 2.03 | 0.0 ± 1.35 | 6.1 ± 4.26 | 0.0 ± 2.64 |
| 51 | 78.6 ± 1.49 | 46.7 ± 1.29 | 20.5 ± 11.48 | 6.0 ± 11.47 |

TABLE 2-continued

Congo red binding data
% Inhibition Aβ (result ± S.D.) at Aβ:test compound wt/wt ratio given

| Test Compound # | 1:1 | 1:0.1 | 1:0.01 | 1:0.001 |
|---|---|---|---|---|
| 52 | 35.4 ± 1.28 | 12.7 ± 2.35 | 0.0 ± 1.29 | 0.0 ± 3.68 |
| 57 | 44.8 ± 0.77 | 14.2 ± 1.56 | 0.1 ± 2.09 | 0.0 ± 4.73 |
| 58 | 52.2 ± 2.65 | 21.1 ± 3.67 | 6.6 ± 3.49 | 2.5 ± 4.22 |
| 61 | 48.9 ± 4.69 | 24.6 ± 10.85 | 2.0 ± 2.89 | 0.0 ± 4.06 |
| 63 | 32.5 ± 5.66 | 8.5 ± 8.01 | 20.1 ± 10.35 | 0.0 ± 1.93 |
| 66 | 55.9 ± 6.83 | 27.7 ± 11.26 | 7.7 ± 0.19 | 0.6 ± 6.61 |
| 67 | 31.5 ± 11.25 | 13.8 ± 11.25 | 8.2 ± 7.08 | 0.0 ± 4.98 |
| 73 | 53.4 ± 1.84 | 22.6 ± 3.51 | 0.6 ± 5.04 | 0.0 ± 15.17 |
| 75 | 59.2 ± 3.23 | 12.8 ± 0.59 | 6.8 ± 2.55 | 2.4 ± 2.95 |
| 76 | 66.6 ± 0.68 | 27.8 ± 7.71 | 4.1 ± 2.23 | 0.3 ± 5.1 |
| 78 | 71.1 ± 1.09 | 39.9 ± 3.94 | 15.4 ± 1.39 | 3.5 ± 1.33 |

Part D—Circular Dichroism Spectroscopy Data

Circular dichroism (CD) spectroscopy is a method that can be used to determine the effects of test compounds to disrupt the secondary structure conformation of amyloid fibrils. In one study, as described in this example, circular dichroism spectroscopy was used to determine the effects of different compounds of the invention on β-sheet conformation of Aβ 1-42 fibrils. For this study, Aβ 1-42 (Bachem Inc., Torrance, Calif.) was first dissolved in a 2 mM NaOH solution, maintaining the pH of these solutions above 10. Aβ 1-42 peptides (at 25 μM), in the absence or presence of test compounds, were made up in 150 mM NaF, 50 mM phosphate buffer, pH 7.4 with 10% trifluoroethanol. Aβ 1-42 was then incubated at 37° C. in the absence or presence of different compounds at an Aβ:test compound wt/wt ratios of 1:0.1, 1:1 and 1:10. After 3 days of incubation, CD spectra were recorded on a Jasco 810 spectropolarimeter (Easton, Md.). All CD spectra were collected with 0.05 cm quartz cells. Wavelength traces were scanned from 190-260 nm at 0.5 nm increments with a bandwidth of 5 nm, at a scan speed of 10 nm/minute, a response time of 32 seconds, and a data pitch of 0.5 nm. The whole system was equilibrated and continuously flushed with nitrogen at 10 ml/minute. For data processing, the average of 5 replicates of "test-compound" spectra were subtracted from the average of 5 replicates of "Aβ 1-42+test compound" spectra to determine the effects of each test compound on disruption of Aβ 1-42 fibrils Ellipticity in degrees was converted to MRE ([Q]; molar residue ellipticity) using the formula [Q]=100·Q·RMW/d·c; where Q is the ellipticity in degrees; RMW is the average residue molecular weight (~107 daltons for Aβ 1-42); d is the pathlength in cm (i.e. 0.05 cm); and c is the concentration in mg/ml (i.e. 0.1 mg/ml).

FIG. 1 shows some of the CD spectra generated in this study. Aβ 1-42 alone in 10% TFE PBS buffer usually demonstrated the typical CD spectra of an amyloid protein with significant β-sheet structure, as demonstrated by the minima observed at 218 nm. However, in the presence of test compounds (such as the compounds #4, 12, 51 and 61 shown in FIG. 1) a marked disruption of β-sheet structure in Aβ 1-42 fibrils was evident (with a significant increase in random coil or α-helix) as shown by the flattening out of the minima observed at 218 nm (compare to Aβ 1-42 alone). This was usually observed at both 3 days (as seen in FIG. 1) and 7 days (not shown) following co-incubation of Aβ 1-42 fibrils with the compounds.

FIG. 2 shows the effect of compound #78 on disruption of Aβ 1-42 fibrils. As shown in this figure, Aβ 1-42 alone demonstrates the typical CD spectra of a predominant β-sheet structure, with a marked minima observed at 218 nm. However, in the presence of compound #78 at 3 days, there is a marked decrease in the minima usually observed at 218 nm (with Aβ 1-42 only), indicative of a disruption of the β-sheet structure of Aβ 1-42 fibrils.

FIG. 3 shows the dose-response effects of compounds #12, 51 and 61 on disruption of the β-sheet structure of Aβ 1-42 fibrils. As an example, increasing concentrations of test compounds #12, 51 and 61 (at Aβ:test compounds wt/wt ratios of 1:0.1, 1:1 and 1:10) caused a general disruption of β-sheet structure as demonstrated by the dose-dependent decrease in the minima observed at 218 nm (when compared to the minima at 218 nm observed with Aβ 1-42 only). Compound #51 was particularly effective when used at an Aβ:test compound wt/wt ratio of 1:10 and was shown to completely disrupt the β-sheet structure of Aβ 1-42 fibrils as shown by the complete flattening out of the minima observed at 218 nm (compare to Aβ 1-42 alone) (FIG. 3).

The CD studies demonstrate that the compounds of this invention have the ability to disrupt/disassemble the β-sheet structure characteristic of Alzheimer's Aβ fibrils. The results of the studies also confirm the previous examples using Thioflavin T fluorometry, SDS-PAGE/ECL, and Congo red binding type assays, that the compounds of this invention are potent anti-amyloid agents.

Example 26

Compounds of this Invention are Potent Disrupters of Type 2 Diabetes IAPP Fibrils The compounds prepared in the synthetic Examples were found also to be potent disruptors/inhibitors of type 2 diabetes IAPP fibrils. In a set of studies, the efficacy of the compounds to cause a disassembly/disruption of pre-formed IAPP fibrils of type 2 diabetes was analyzed.

Part A—Thioflavin T Fluorometry Data

In one study, Thioflavin T fluorometry was used to determine the effects of the compounds, and of EDTA (as a negative control). In this assay Thioflavin T binds specifically to fibrillar amyloid, and this binding produces a fluorescence enhancement at 485 nm that is directly proportional to the amount of IAPP fibrils present. The higher the fluorescence, the greater the amount of IAPP fibrils present (Naki et al, *Lab. Invest.* 65:104-110, 1991; Levine III, *Protein Sci.* 2:404-410, 1993; *Amyloid: Int. J. Exp. Clin. Invest.* 2:1-6, 1995).

In this study, 25 µM of pre-fibrillized IAPP (Bachem Inc) was incubated at 37° C. for 3 days either alone, or in the presence of one of the compounds or EDTA (at IAPP:test compound weight ratios of 1:1, 1:0.1, 1:0.01 or 1:0.001). Following 3-days of co-incubation, 50 µl of each incubation mixture was transferred into a 96-well microtiter plate containing 150 µl of distilled water and 50 µl of a Thioflavin T solution (i.e. 500 mM Thioflavin T in 250 mM phosphate buffer, pH 6.8). The fluorescence was read at 485 nm (444 nm excitation wavelength) using an ELISA plate fluorometer after subtraction with buffer alone or compound alone, as blank.

The results are presented in Table 3 below. For example, whereas EDTA caused no significant inhibition of IAPP fibrils at all concentrations tested, the compounds all caused a dose-dependent disruption/disassembly of pre-formed IAPP fibrils to various extents. The most efficacious compounds to disrupt IAPP fibrils appeared to be compounds #3, 4, 23, 63, and 78. For example, compound #3 caused a significant ($p<0.01$) 97.7±0.19% inhibition when used at an IAPP:test compound ratio of 1:0.1, and a 79.9±1.47% disruption when used at a IAPP:compound wt/wt ratio of 1:0.01. Under the same conditions (i.e. IAPP:test compound wt/wt ratio of 1:0.1), compound #4 caused a 96.0±1.0% disruption, compound #23 caused a 67.2±18.35% disruption, compound #63 caused a 84.2±1.16% disruption, compound #78 caused a 92.4±0.27% disruption, and compound #26 caused a 45.9±17.73% disruption. This study indicated that the compounds of this invention are also potent disruptors/inhibitors of type 2 diabetes IAPP fibrils, and usually exert their effects in a dose-dependent manner.

TABLE 3

Thioflavin T fluorometry data - disruption of type 2 diabetes IAPP fibrils
% Inhibition IAPP (result ± S.D.) at IAPP:test compound wt/wt ratio given

| Test Compound # | 1:1 | 1:0.1 | 1:0.01 | 1:0.001 |
| --- | --- | --- | --- | --- |
| EDTA (control) | 4.4 ± 9.23 | 0.1 ± 2.59 | 0.0 ± 5.23 | 4.2 ± 1.05 |
| 1 | 99.0 ± 0.11 | 93.0 ± 1.27 | 57.3 ± 0.16 | 6.4 ± 4.40 |
| 3 | 100 ± 0.20 | 97.7 ± 0.19 | 79.9 ± 1.47 | 30.7 ± 6.71 |
| 4 | 99.7 ± 0.23 | 96.0 ± 0.10 | 63.2 ± 2.09 | 17.3 ± 4.07 |
| 8 | 72.8 ± 1.77 | 67.8 ± 1.74 | 29.6 ± 5.97 | 11.4 ± 12.78 |
| 12 | 99.9 ± 0.19 | 86.0 ± 0.76 | 37.5 ± 0.76 | 13.0 ± 10.34 |
| 19 | 100.0 ± 0.24 | 94.0 ± 0.10 | 51.7 ± 2.98 | 16.7 ± 10.20 |
| 21 | 98.5 ± 0.06 | 85.4 ± 0.86 | 25.8 ± 3.61 | 5.4 ± 15.41 |
| 23 | 85.2 ± 0.55 | 67.2 ± 18.35 | 44.3 ± 32.47 | 27.3 ± 45.38 |
| 26 | 52.5 ± 2.44 | 45.9 ± 17.73 | 24.6 ± 6.77 | 3.7 ± 4.67 |
| 51 | 99.9 ± 0.11 | 96.6 ± 1.00 | 56.6 ± 1.69 | 11.8 ± 6.45 |
| 52 | 97.9 ± 0.19 | 86.9 ± 3.09 | 49.2 ± 4.47 | 16.0 ± 8.42 |
| 57 | 94.1 ± 0.46 | 73.2 ± 1.19 | 37.3 ± 0.78 | 1.9 ± 5.24 |
| 58 | 98.1 ± 1.04 | 87.6 ± 1.16 | 48.8 ± 2.05 | 8.9 ± 6.87 |
| 61 | 96.8 ± 0.47 | 83.6 ± 1.27 | 35.4 ± 5.68 | 0.5 ± 6.33 |
| 63 | 94.9 ± 0.65 | 84.2 ± 1.16 | 56.2 ± 8.77 | 19.0 ± 0.30 |
| 66 | 98.5 ± 0.06 | 94.0 ± 2.88 | 47.6 ± 8.16 | 11.1 ± 5.28 |
| 67 | 98.6 ± 0.22 | 81.4 ± 6.96 | 34.8 ± 1.87 | 16.1 ± 12.40 |
| 75 | 100 ± 0.35 | 90.0 ± 0.27 | 43.9 ± 5.34 | 6.0 ± 6.46 |
| 76 | 99.6 ± 1.01 | 87.5 ± 1.89 | 41.5 ± 6.67 | 9.0 ± 0.32 |
| 78 | 99.5 ± 0.26 | 92.4 ± 0.27 | 58.3 ± 1.20 | 15.3 ± 4.73 |

Part B: Congo Red Binding Data

In the Congo red binding assay the ability of a given test compound to alter amyloid (in this case, IAPP) binding to Congo red is quantified. In this assay, IAPP and test compounds were incubated for 3 days and then vacuum filtered through a 0.2 µm filter. The amount of IAPP retained in the filter was then quantitated following staining of the filter with Congo red. After appropriate washing of the filter, any lowering of the Congo red color on the filter in the presence of the test compound (compared to the Congo red staining of the amyloid protein in the absence of the test compound) was indicative of the test compound's ability to diminish/alter the amount of aggregated and congophilic IAPP.

In the study, the ability of IAPP fibrils to bind Congo red in the absence or presence of increasing amounts of the compounds or EDTA (at IAPP:test compound weight ratios of 1:1, 1:0.1, 1:0.01 or 1:0.001) was determined. The results of 3-day incubations are presented in Table 4 below. Whereas EDTA caused no significant inhibition of IAPP fibril binding to Congo red at all concentrations tested, the compounds usually caused a dose-dependent inhibition of IAPP binding to Congo red. For example, compound #3 caused a significant (p<0.01) 55.5±2.68% inhibition of Congo red binding to IAPP fibrils when used at an IAPP:test compound wt/wt ratio of 1:1, and a significant (p<0.01) 37.9±3.10% inhibition of Congo red binding when used at an IAPP:test compound wt/wt ratio of 1:0.1. Compound #4 caused a significant (p<0.01) 68.9±1.22% inhibition of Congo red binding to IAPP fibrils when used at an IAPP:test compound wt/wt ratio of 1:1, and a 25.4±4.68% inhibition of Congo red binding when used at a NAC:test compound wt/wt ratio of 1:0.01. This study indicated that compounds of this invention are also potent inhibitors of type 2 diabetes IAPP fibril binding to Congo red, and usually exert their effects in a dose-dependent manner.

TABLE 4

Congo red binding data
% Inhibition IAPP (result ± S.D.) at IAPP:test compound wt/wt ratio given

| Test Compound # | 1:1 | 1:0.1 | 1:0.01 | 1:0.001 |
|---|---|---|---|---|
| EDTA (control) | 0.0 ± 3.69 | 0.0 ± 1.91 | 3.6 ± 2.83 | 6.6 ± 2.27 |
| 1 | 40.7 ± 2.49 | 10.6 ± 3.40 | 18.6 ± 4.05 | 6.4 ± 2.07 |
| 3 | 55.5 ± 2.68 | 37.9 ± 3.10 | 16.3 ± 1.13 | 11.1 ± 5.26 |
| 4 | 68.9 ± 1.22 | 25.4 ± 4.68 | 9.0 ± 0.51 | 0.0 ± 1.05 |
| 8 | 0.0 ± 2.84 | 0.0 ± 2.94 | 7.2 ± 2.27 | 0.0 ± 6.46 |
| 12 | 39.8 ± 0.26 | 8.3 ± 0.85 | 6.9 ± 2.45 | 0.0 ± 2.40 |
| 19 | 49.3 ± 3.97 | 21.0 ± 3.70 | 6.0 ± 0.78 | 2.9 ± 4.40 |
| 21 | 35.9 ± 0.21 | 10.4 ± 3.53 | 5.1 ± 4.53 | 0.0 ± 2.10 |
| 23 | 5.5 ± 2.33 | 4.5 ± 4.12 | 9.3 ± 1.40 | 5.1 ± 2.45 |
| 26 | 0.0 ± 1.21 | 7.5 ± 2.83 | 5.3 ± 6.14 | 10.8 ± 2.63 |
| 51 | 55.6 ± 1.48 | 27.5 ± 3.49 | 3.6 ± 2.59 | 1.6 ± 1.01 |
| 52 | 31.3 ± 0.27 | 11.5 ± 1.21 | 11.0 ± 3.27 | 10.2 ± 0.52 |
| 57 | 15.7 ± 3.77 | 8.9 ± 3.90 | 8.5 ± 3.19 | 4.5 ± 0.64 |
| 58 | 24.5 ± 0.57 | 0.7 ± 6.21 | 4.6 ± 2.35 | 0.0 ± 1.93 |
| 61 | 23.7 ± 0.39 | 0.0 ± 7.07 | 4.0 ± 1.78 | 0.0 ± 3.87 |
| 63 | 15.4 ± 1.34 | 4.5 ± 1.62 | 11.7 ± 2.26 | 0.0 ± 2.25 |
| 66 | 41.4 ± 3.84 | 15.7 ± 2.53 | 5.7 ± 4.23 | 4.8 ± 1.86 |
| 67 | 26.3 ± 2.76 | 5.5 ± 2.52 | 10.6 ± 1.29 | 0.0 ± 3.45 |
| 75 | 49.0 ± 1.17 | 7.4 ± 0.70 | 11.3 ± 2.24 | 2.9 ± 0.69 |
| 76 | 53.9 ± 5.44 | 16.5 ± 2.60 | 14.2 ± 2.25 | 3.4 ± 1.07 |
| 78 | 56.3 ± 5.32 | 16.7 ± 6.80 | 19.9 ± 2.12 | 6.6 ± 3.04 |

Example 27

Compounds of this Invention are Potent Disrupters of Parkinson's Disease NAC Fibrils The tested compounds of this invention were found also to be potent disruptors/inhibitors of Parkinson's disease NAC fibrils. NAC is a 35-amino acid fragment of α-synuclein that has been demonstrated to form amyloid-like fibrils when incubated at 37° C. for a few days. It is the amyloidogenic fragment of α-synuclein and is postulated to play an important role in the pathogenesis of Parkinson's disease and other synucleinopathies. In a set of studies, the efficacy of the compounds to cause a disassembly/disruption of pre-formed NAC fibrils of Parkinson's disease was analyzed.

Part A—Thioflavin T Fluorometry Data

In one study, Thioflavin T fluorometry was used to determine the effects of compounds #1, 3, 23, 26, 52, 63, 66, 67, and EDTA (as a negative control). In this assay, Thioflavin T binds specifically to NAC fibrils, and this binding produces a fluorescence enhancement at 485 nm that is directly proportional to the amount of NAC fibrils present. The higher the fluorescence, the greater the amount of NAC fibrils present (Naki et al, *Lab. Invest.* 65:104-110, 1991; Levine III, *Protein Sci.* 2:404-410, 1993; *Amyloid: Int. J. Exp. Clin. Invest.* 2:1-6, 1995).

In this study, 25 µM of pre-fibrillized NAC (Bachem Inc) was incubated at 37° C. for 3 days either alone or in the presence of dihydroxy synthetic analog compounds #1, 3, 23, 26, 52, 63, 66, 67, or EDTA (at NAC:test compound weight ratios of 1:1, 1:0.1, 1:0.01 or 1:0.001). Following 3-days of co-incubation, 50 µl of each incubation mixture was transferred into a 96-well microtiter plate containing 150 µl of distilled water and 50 µl of a Thioflavin T solution (i.e. 500 mM Thioflavin T in 250 mM phosphate buffer, pH 6.8). The fluorescence was read at 485 nm (444 nm excitation wavelength) using an ELISA plate fluorometer after subtraction with buffer alone or compound alone, as blank.

The results of the 3-day incubations are presented below in Table 5. For example, whereas EDTA caused no significant inhibition of NAC fibrils at all concentrations tested, compounds 1, 3, 52, 63, 66, and 67 all caused a dose-dependent disruption/disassembly of pre-formed NAC fibrils to various extents. For example, compound #3 caused a significant (p<0.01) 91.0±1.99% inhibition when used at an NAC:test compound ratio of 1:0.1, and a 93.9±0.77% disruption when used at a NAC:compound wt/wt ratio of 1:0.01. Under the same conditions (i.e. NAC:test compound wt/wt ratio of 1:0.1), compound #1 caused a 99.5±0.53% disruption, compound #26 caused a 61.3±6.52% disruption, compound #52 caused a 89.2±1.49% disruption, compound #66 caused a 82.5±5.37% disruption, and compound #67 caused a 50.0±7.03% disruption. This study indicated that compounds of this invention are potent disruptors/inhibitors of Parkinson's disease NAC fibrils, and usually exert their effects in a dose-dependent manner.

TABLE 5

Thioflavin T fluorometry data - disruption of Parkinson's disease NAC fibrils
% Inhibition NAC (result ± S.D.) at NAC:test compound wt/wt ratio given

| Test Compound # | 1:1 | 1:0.1 | 1:0.01 | 1:0.001 |
|---|---|---|---|---|
| EDTA (control) | 20.0 ± 11.8 | 0.0 ± 5.87 | 0.0 ± 10.87 | 0.0 ± 11.6 |
| 1 | 100.0 ± 1.00 | 99.5 ± 0.53 | 68.2 ± 2.55 | 0.0 ± 7.14 |
| 3 | 98.0 ± 1.78 | 91.0 ± 1.99 | 93.9 ± 0.77 | 67.3 ± 6.37 |
| 23 | 58.0 ± 8.43 | 53.3 ± 12.02 | 35.6 ± 9.73 | 0.0 ± 26.42 |
| 26 | 70.4 ± 3.22 | 61.3 ± 6.52 | 56.8 ± 4.60 | 0.0 ± 16.88 |
| 52 | 99.7 ± 1.93 | 89.2 ± 1.49 | 79.6 ± 6.43 | 13.8 ± 10.49 |
| 63 | 45.6 ± 31.03 | 34.5 ± 17.15 | 33.0 ± 1.69 | 17.3 ± 12.57 |
| 66 | 98.9 ± 0.65 | 82.5 ± 5.37 | 43.4 ± 3.45 | 30.5 ± 9.55 |
| 67 | 97.4 ± 1.19 | 50.0 ± 7.03 | 30.6 ± 5.75 | 11.9 ± 15.98 |

Part B: Congo Red Binding Data

In the Congo red binding assay, the ability of a given test compound to alter amyloid (in this case, NAC) binding to Congo red is quantified. In this assay, NAC and test compounds were incubated for 3 days and then vacuum filtered through a 0.2 µm filter. The amount of NAC retained in the filter was then quantitated following staining of the filter with Congo red. After appropriate washing of the filter, any lowering of the Congo red color on the filter in the presence of the test compound (compared to the Congo red staining of the amyloid protein in the absence of the test compound) was indicative of the test compound's ability to diminish/alter the amount of aggregated and congophilic NAC.

In one study, the ability of NAC fibrils to bind Congo red in the absence or presence of increasing amounts of compounds #1, 3, 23, 26, 63, 66, 67, or EDTA (at NAC:test compound weight ratios of 1:1, 1:0.1, 1:0.01 or 1:0.001) was determined. The results of 3-day incubations are presented in Table 6. Whereas EDTA caused no significant inhibition of NAC fibril binding to Congo red at all concentrations tested, the compounds tested caused a dose-dependent inhibition of NAC binding to Congo red as demonstrated in Table 6 below. For example, compound #3 caused a significant (p<0.01) 94.4±2.48% inhibition of Congo red binding to NAC fibrils when used at a NAC:test compound wt/wt ratio of 1:1, and a significant (p<0.01) 83.2±3.57% inhibition of Congo red binding when used at a NAC:test compound wt/wt ratio of 1:0.1. In comparison, compound #1 caused a 75.4±2.96% inhibition of Congo red binding to NAC fibrils when used at a NAC:test compound wt/wt ratio of 1:1, and an 75.9±2.48% inhibition of Congo red binding when used at a NAC:test compound wt/wt ratio of 1:0.1. In another example, synthetic analog compound #67 caused a significant (p<0.01) 81.2+/−2.87% inhibition of Congo red binding to NAC fibrils when used at an NAC:test compound wt/wt ratio of 1:1, and a significant (p<0.01) 47.7±8.20% inhibition of Congo red binding when used at a NAC:test compound wt/wt ratio of 1:0.01. In another example, compound #26 caused a significant 34.4±10.19% inhibition of Congo red binding when used at a NAC:test compound ratio of 1:1, and a 36.7%±5.59% inhibition of Congo red binding when used at a NAC:test compound ratio of 1:0.1. This study also indicated that compounds of this invention are also potent inhibitors of Parkinson's disease type NAC fibril binding to Congo red, and usually exert their effects in a dose-dependent manner.

TABLE 6

Congo red binding data - disruption of Parkinson's disease NAC fibrils
% Inhibition NAC (result ± S.D.) at NAC:test compound wt/wt ratio given

| Test Compound # | 1:1 | 1:0.1 | 1:0.01 | 1:0.001 |
|---|---|---|---|---|
| EDTA (control) | 0.2 ± 7.33 | 0.0 ± 38.26 | 0.0 ± 22.0 | 0.0 ± 20.57 |
| 1 | 75.4 ± 2.96 | 75.9 ± 2.58 | 40.7 ± 4.23 | 0.0 ± 11.39 |
| 3 | 94.4 ± 2.48 | 83.2 ± 3.57 | 81.7 ± 2.82 | 65.2 ± 5.40 |
| 23 | 41.0 ± 8.54 | 30.3 ± 12.06 | 25.6 ± 5.37 | 0.0 ± 9.00 |
| 26 | 34.4 ± 10.19 | 36.7 ± 5.59 | 36.4 ± 0.67 | 0.0 ± 27.34 |
| 52 | 73.8 ± 3.15 | 71.2 ± 7.17 | 78.9 ± 4.76 | 0.0 ± 24.43 |
| 63 | 54.5 ± 7.56 | 9.3 ± 10.5 | 34.0 ± 3.66 | 0.0 ± 30.84 |
| 66 | 81.1 ± 1.74 | 72.4 ± 1.79 | 51.0 ± 9.50 | 19.5 ± 37.59 |
| 67 | 81.2 ± 2.87 | 47.7 ± 8.20 | 39.2 ± 10.25 | 15.5 ± 41.42 |

Example 28

Other Bis- and Tris-Dihydroxyaryl Compounds of the Invention

Besides the 24 compounds described in detail in Examples 1-24, this Example describes other bis- and tris(dihydroxyaryl) compounds that also serve as potent disruptor/inhibitors of amyloid fibrils in Alzheimer's disease (i.e. Aβ), type 2 diabetes (i.e. IAPP), other amyloid diseases, as well as in Parkinson's disease (i.e. α-synuclein/NAC) and other synuclein fibril diseases. A common structural motif that is present in all of the compounds disclosed herein is the presence of two or three dihydroxyaryl groups. These compounds are compounds #2, 5, 6, 7, 10, 11, 13, 14, 15, 16, 17, 18, 20, 22, 24, 25, 27, 28, 29, 30, 31, 32, 33, 34, 35, 36, 37, 38, 39, 40, 41, 42, 43, 44, 45, 46, 47, 48, 49, 50, 53, 54, 55, 56, 59, 60, 62, 64, 65, 68, 69, 70, 71, 72, 74, 79 and 80. These are also referred respectively to as DC-0002, DC-0005, DC-0006, DC-0007, DC-0010, DC-0011, DC-0013, DC-0014, DC-0015, DC-0016, DC-0017, DC-0018, DC-0020, DC-0022, DC-0024, DC-0025, DC-0027, DC-0028, DC-0029, DC-0030, DC-0031, DC-0032, DC-0033, DC-0034, DC-0035, DC-0036, DC-0037, DC-0038, DC-0039, DC-0040, DC-0041, DC-0042, DC-0043, DC-0044, DC-0045, DC-0046, DC-0047, DC-0048, DC-0049, DC-0050, DC-0053, DC-0054, DC-055, DC-0056, DC-0059, DC-0060, DC-0062, DC-0064, DC-0065, DC-0068, DC-0069, DC-0070, DC-0071, DC-0072, DC-0074, DC-0079 and DC-0080, respectively. [Compound #77 also appears in the compound chart following].

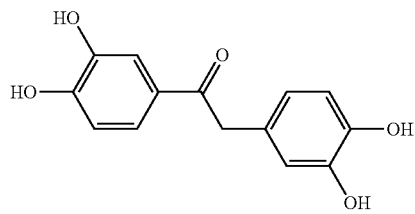

3,4,3',4'-Tetrahydroxydesoxybenzoin

-continued

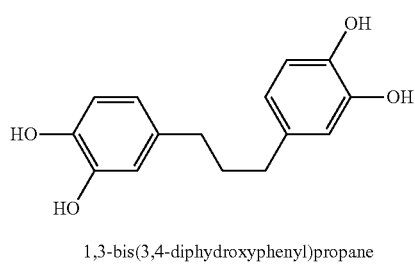

1,3-bis(3,4-diphydroxyphenyl)propane

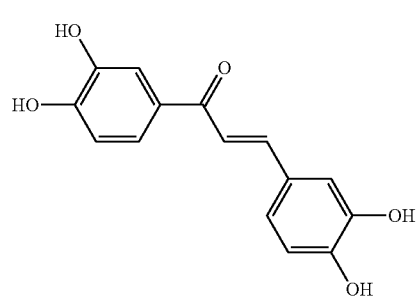

3,4,3',4'-Tetrahydroxychalcone

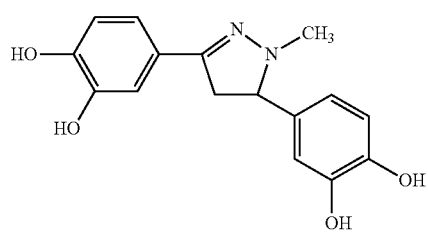

3,5-bis(3,4-dihydroxyphenyl)-1-methyl-1H-pyrazoline

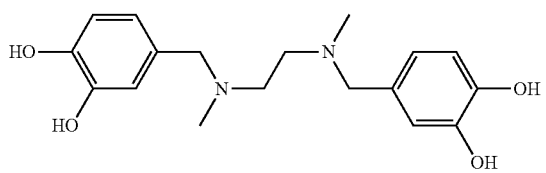

N,N'-bis(3,4-dihydroxybenzyl)-N,N'-dimethyl-ethylenediamine

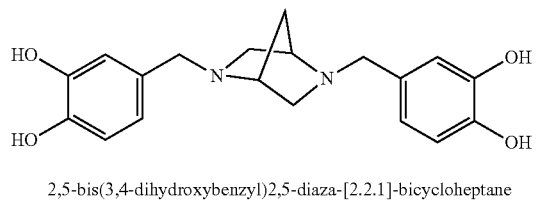

2,5-bis(3,4-dihydroxybenzyl)2,5-diaza-[2.2.1]-bicycloheptane

-continued

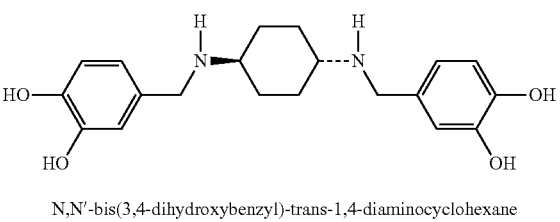

N,N'-bis(3,4-dihydroxybenzyl)-trans-1,4-diaminocyclohexane

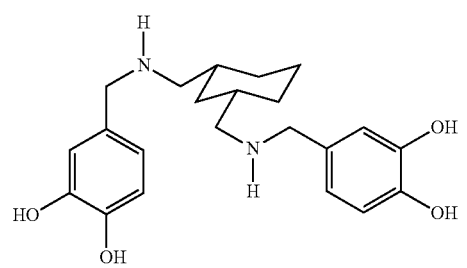

N,N'-bis(3,4-dihydroxybenzyl)-cis-1,3-bis-aminomethylcyclohexane

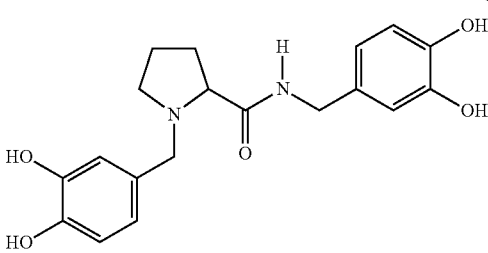

N-(3,4-dihydroxybenzyl)proline 3,4-dihydroxy-benzylamide

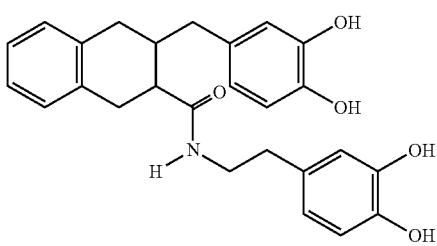

2-(3,4-hydroxybenzyl)isoquinoline-3-carboxylic acid 3,4-dihydroxyphenethylamide

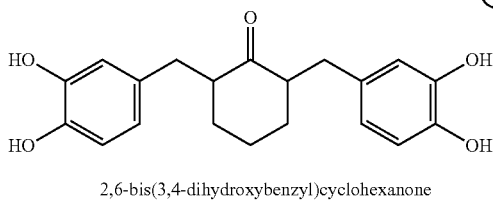

2,6-bis(3,4-dihydroxybenzyl)cyclohexanone

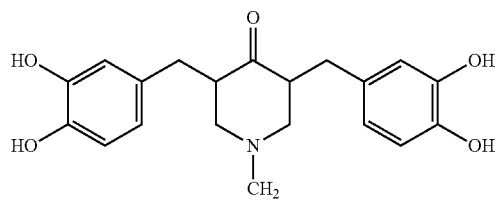

(18)

3,5-bis(3,4-dihydroxybenzyl)-1-methyl-4-piperidinone

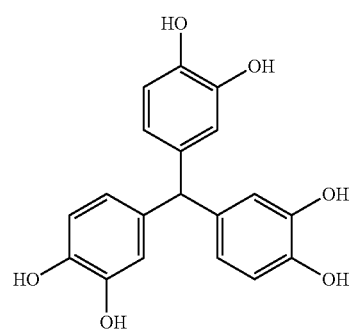

(20)

Tris-(3,4-dihydroxybenzyl)methane

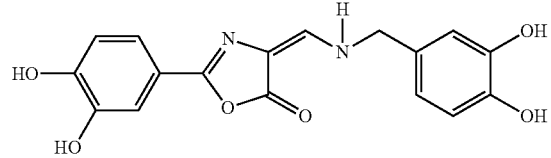

(22)

4-(3,4-dihydroxybenzylaminomethylene)-2-(3,4-dihydroxyphenyl)oxazoline-5-one

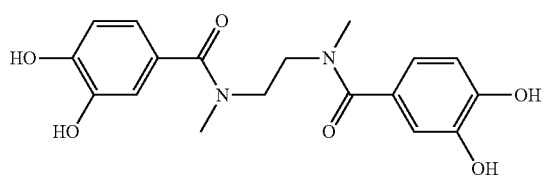

(24)

N,N'-bis(3,4-dihydroxybenzoyl)-N,N'-dimethyl(-)ethylenediamine

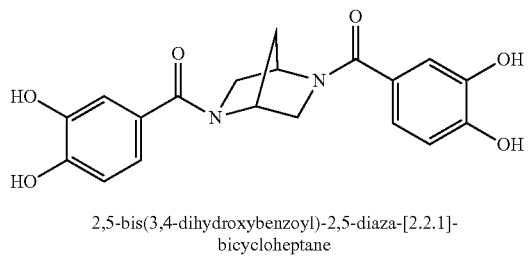

(25)

2,5-bis(3,4-dihydroxybenzoyl)-2,5-diaza-[2.2.1]-bicycloheptane

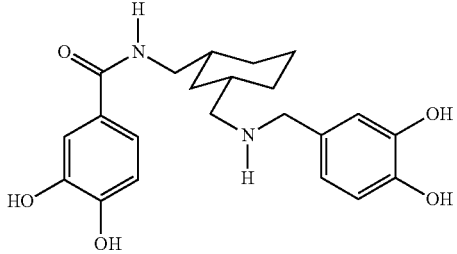

(27)

N,N'-bis(3,4-dihydroxybenzoyl)-cis-1,3-bis-aminomethylcyclohexane

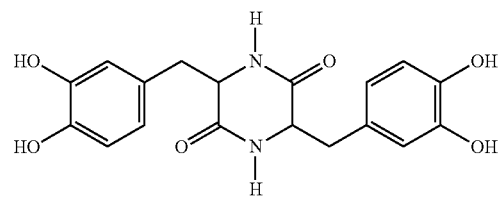

(28)

3,6-bis(3,4-dihydroxybenzyl)-1-methyl-2,5-diketopiperazine

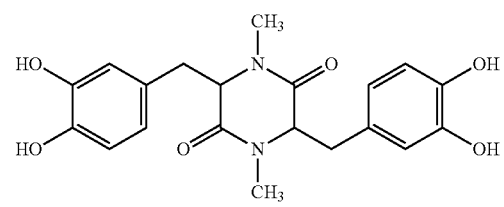

(29)

3,6-bis(3,4-dihydroxybenzylidene)-1,4-dimethyl-2,5-diketopiperazine

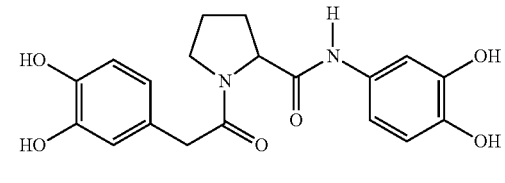

(30)

N-(3,4-hydroxyphenylacetyl)proline-3,4-di-hydroxyanilide

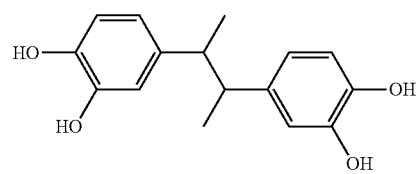

(31)

2,3-bis(3,4-dihydroxyphenyl)butane

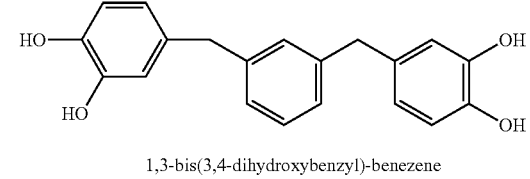

(32)

1,3-bis(3,4-dihydroxybenzyl)-benzene

-continued (33)

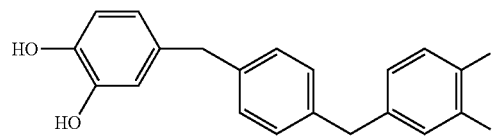

1,4-bis(3,4-dihydroxybenzyl)-benezene (34)

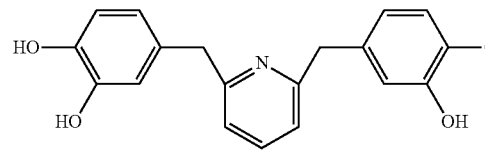

2,6-bis(3,4-dihydroxybenzyl)pyridine (35)

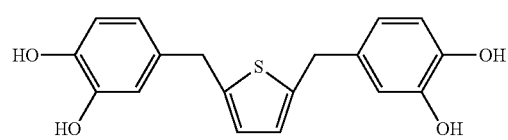

2,5-bis(3,4-dihydroxybenzyl)thiophene (36)

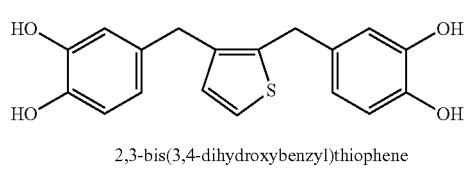

2,3-bis(3,4-dihydroxybenzyl)thiophene (37)

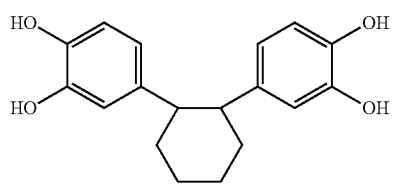

1,2-bis(3,4-dihydroxyphenyl)cyclohexane (38)

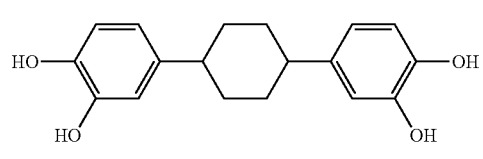

3,7-bis(3,4-dihydroxyphenyl)cyclohexane

-continued (39)

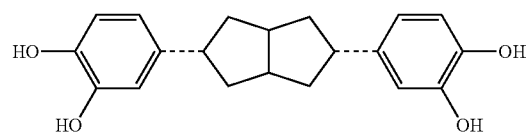

2,5-bis(3,4-dihydroxybenzoyl)bicyclo[3.3.0](-)octane (40)

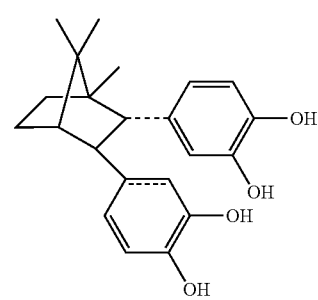

2,3-bis(3,4-dihydroxphenyl)-1,7,7-trimethyl-bicyclo[2.2.1]heptane (41)

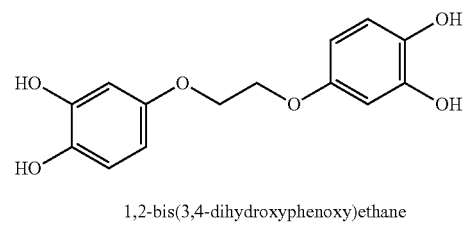

1,2-bis(3,4-dihydroxyphenoxy)ethane (42)

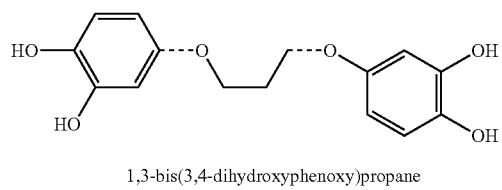

1,3-bis(3,4-dihydroxyphenoxy)propane (43)

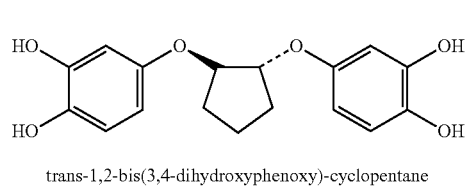

trans-1,2-bis(3,4-dihydroxyphenoxy)-cyclopentane (44)

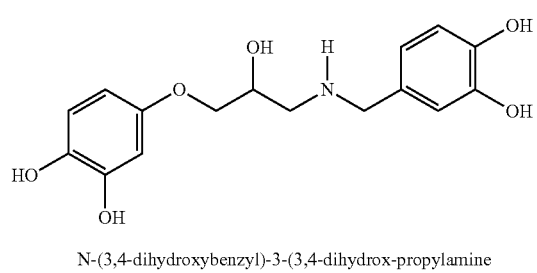

N-(3,4-dihydroxybenzyl)-3-(3,4-dihydrox-propylamine (45)

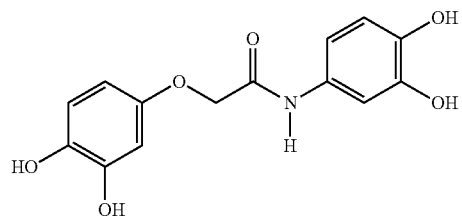

3,4-dihydroxyphenoxy acetic acid
3,4-dihydroxyanilide (46)

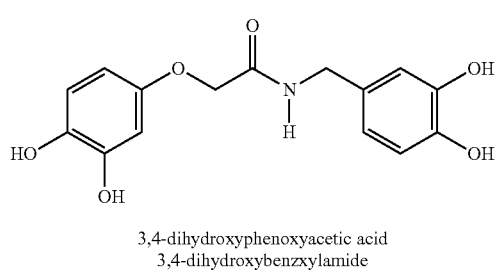

3,4-dihydroxyphenoxyacetic acid
3,4-dihydroxybenzxylamide (47)

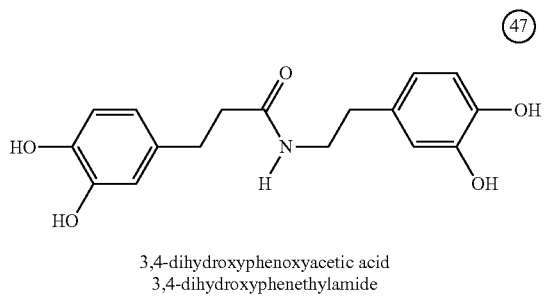

3,4-dihydroxyphenoxyacetic acid
3,4-dihydroxyphenethylamide (48)

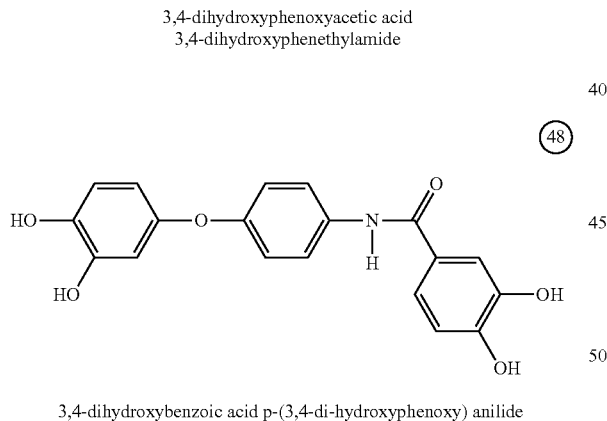

3,4-dihydroxybenzoic acid p-(3,4-di-hydroxyphenoxy) anilide (49)

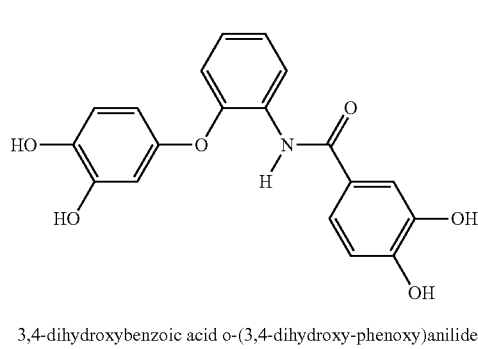

3,4-dihydroxybenzoic acid o-(3,4-dihydroxy-phenoxy)anilide (50)

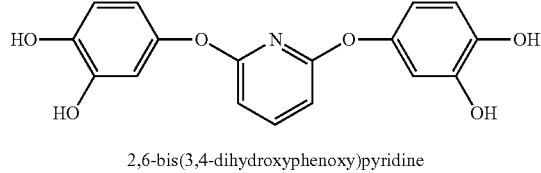

2,6-bis(3,4-dihydroxyphenoxy)pyridine (53)

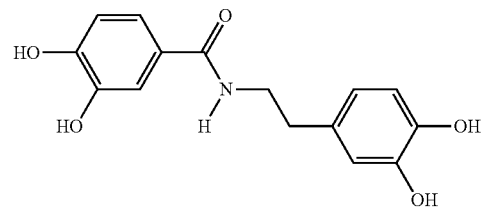

3,4-dihydroxybenzoic acid 3,4-dihydroxy-phenethyl amide (54)

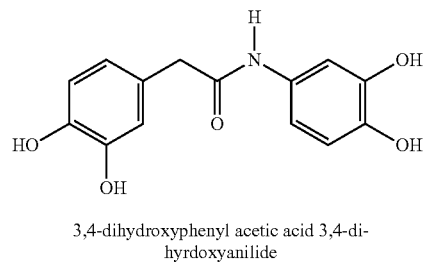

3,4-dihydroxyphenyl acetic acid 3,4-di-hyrdoxyanilide (55)

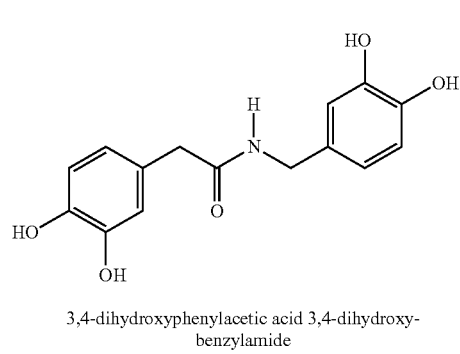

3,4-dihydroxyphenylacetic acid 3,4-dihydroxy-benzylamide (56)

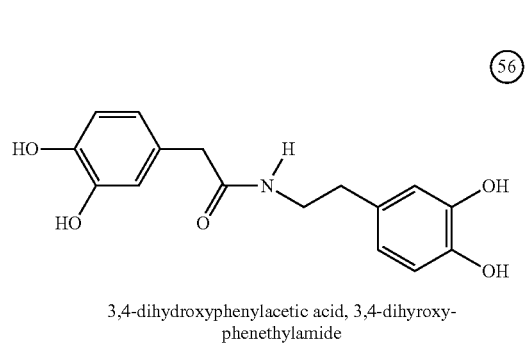

3,4-dihydroxyphenylacetic acid, 3,4-dihyroxy-phenethylamide

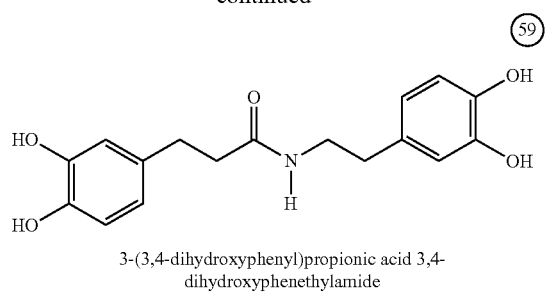

3-(3,4-dihydroxyphenyl)propionic acid 3,4-dihydroxyphenethylamide

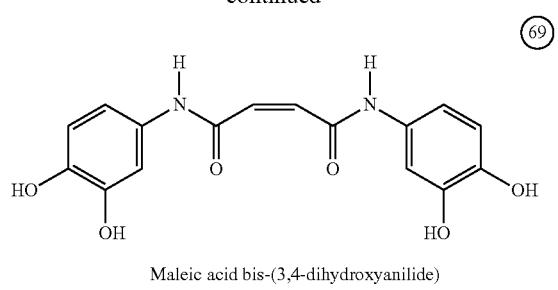

Maleic acid bis-(3,4-dihydroxyanilide)

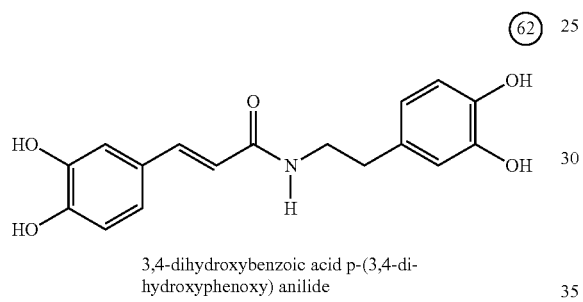

3,4-dihydroxycinnamic acid 3,4-dihydroxy-anilide

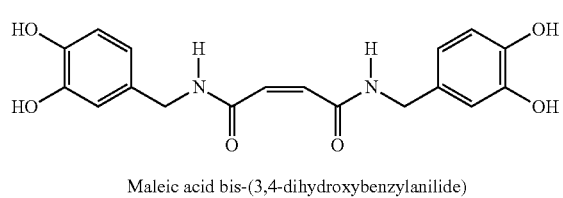

Maleic acid bis-(3,4-dihydroxybenzylanilide)

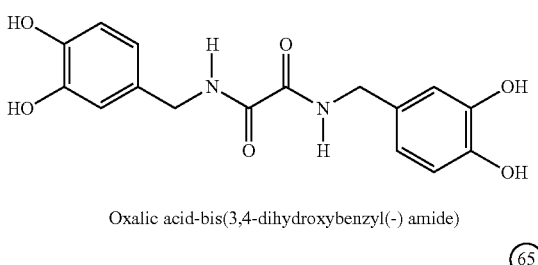

3,4-dihydroxybenzoic acid p-(3,4-di-hydroxyphenoxy) anilide

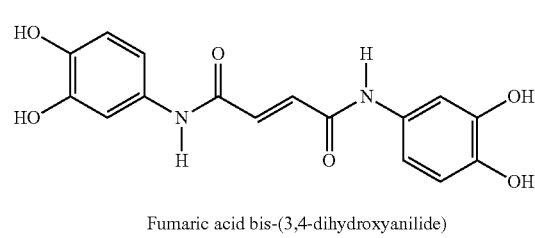

Fumaric acid bis-(3,4-dihydroxyanilide)

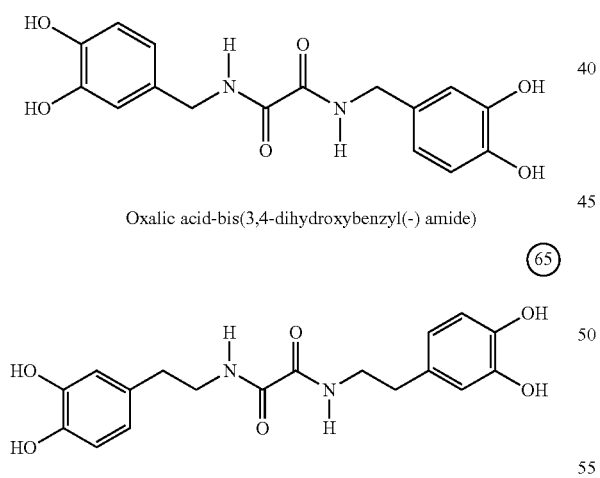

Oxalic acid-bis(3,4-dihydroxybenzyl(-) amide)

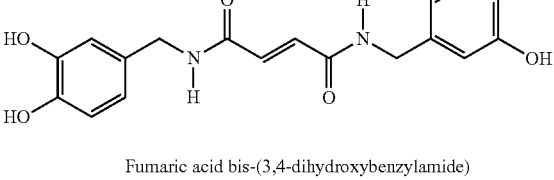

Fumaric acid bis-(3,4-dihydroxybenzylamide)

Oxalic acid-bis(3,4-dihydroxyphen(-) ethylamide)

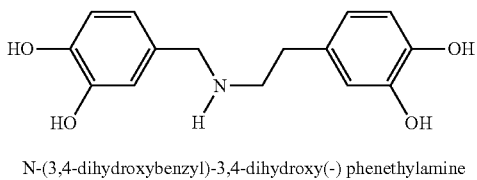

N-(3,4-dihydroxybenzyl)-3,4-dihydroxy(-) phenethylamine

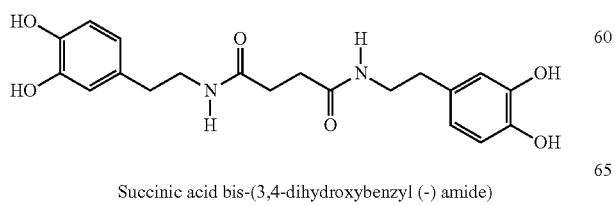

Succinic acid bis-(3,4-dihydroxybenzyl (-) amide)

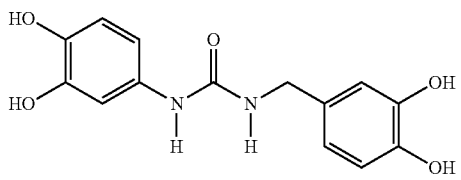

1-(3,4-dihyroxyphenyl)-3-(3,4-dihydroxybenzyl) urea

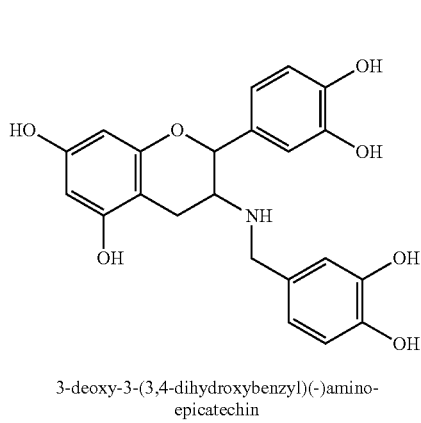

3-deoxy-3-(3,4-dihydroxybenzyl)(-)amino-
epicatechin

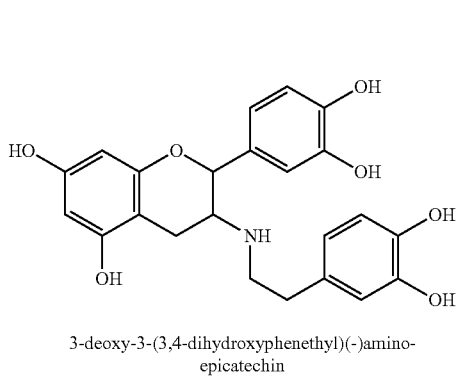

3-deoxy-3-(3,4-dihydroxyphenethyl)(-)amino-
epicatechin

These compounds may be prepared by the methods used to produce the compounds illustrated in Examples 1 through 23 and variations thereof easily determinable by a person of ordinary skill in the art. Thus, for example, compounds 10 and 11 may be prepared by the method used for compound 9, substituting N,N'-dimethylethylenediamine and 2,5-diaza[2.2.1]bicycloheptane for the piperazine of Example 5, compounds #17 and 18 may be prepared by the method used for compound 19, substituting cyclohexanone and N-methyl-4-piperidinone for the tropinone of Example 7; compounds 24 and 25 may be prepared by the method used for compound 12, substituting N,N'-dimethylethylenediamine and 2,5-diaza[2.2.1]bicycloheptane for the trans-1,2-diaminocyclohexane of Example 6, and so on. A person of ordinary skill in the art will have no difficulty, having regard to that skill and this disclosure, in preparing the compounds illustrated above or the compounds of the formula given in claim 1.

Example 29

Compound of the Invention with Rigid Scaffolds

This Example illustrates six further compounds of this invention (compounds #81, 82, 83, 84, 85, and 86 or DC-0081 through DC-0086) that also serve as potent disruptor/inhibitors of amyloid fibrils in Alzheimer's disease (i.e. Aβ), type 2 diabetes (i.e. IAPP), other amyloid diseases, as well as in Parkinson's disease (i.e. α-synuclein/NAC) and other synuclein fibril diseases. These compounds have relatively rigid scaffold structures. The synthesis of compound 85 is given in Example 24.

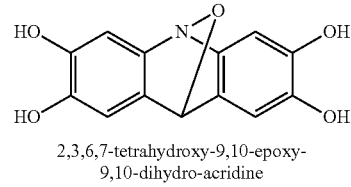

2,3,6,7-tetrahydroxy-9,10-epoxy-
9,10-dihydro-acridine

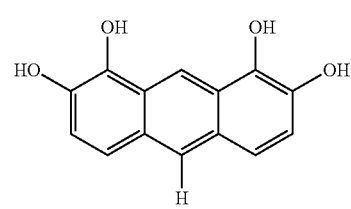

10-Amino-anthracene-1,2,7,8-tetraol

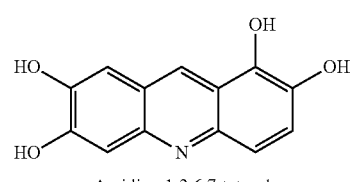

Acridine-1,2,6,7-tetraol

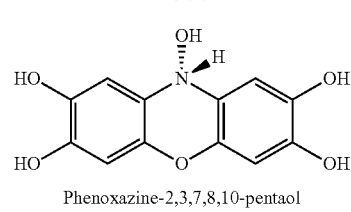

Phenoxazine-2,3,7,8,10-pentaol

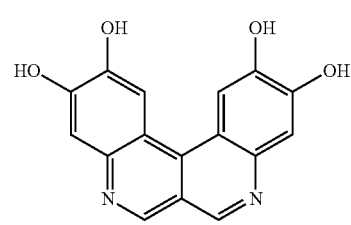

Dibenzo[c,f][2,7]naphthyridine-2,3,10,11-tetraol

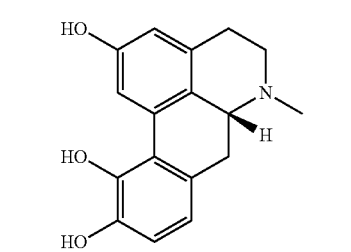

6-Methyl-5,6,6a,7-tetrahydro-4H-dib
enzo[de,g]quinoline-2,10,11-triol

Example 30

Methylenedioxy Analogs

A strategy for the delivery of the dihydroxyaryl compounds of this invention to improve and/or cause more favorable metabolism and bioavailability characteristics involves the protection of the hydroxy groups of the dihydroxyaryl compounds with methylenedioxy groups. This strategy is exemplified in the 80 structures shown below, and is equally applicable to protect the dihydroxyaryl groups of compounds #81-86. Methylenedioxy analogs represent intermediate hydroxy protecting structures that are made to successfully complete the synthesis of the dihydroxyaryl compounds described in the invention. These closed-ring compounds also tend to be more stable, and hydrophobic (water insoluble), and less likely to be altered or degraded due to the oxidation that could occur if hydroxyl groups were present. In addition, these compounds make good prodrugs especially for delivery to the brain due to their hydrophobic nature. Hydrophobic compounds that are lipid soluble tend to be attractive compounds for brain delivery since they are usually able to penetrate the blood-brain-barrier.

The methylenedioxy analogs are generally available as intermediates in the synthesis of the corresponding dihydroxyaryl compounds, as may be seen from the syntheses illustrated in Examples 1-23. These compounds are expected to be efficacious in their ability to cause a disruption/disassembly and inhibition of amyloid and synuclein fibrils, once the methylenedioxy structures are cleaved to yield hydroxyl groups. Conversion of the hydroxyl groups to methylenedioxy derivatives also yields prodrugs that are believed to improve toxicity (i.e. being less toxic), metabolism (since the OH groups will be less likely to be altered by methylation, glucuronidation and sulfation), and bioavailability. In this prodrug concept, it is believed that the prodrug conversion takes place in the plasma (following its protection through the gut), and closer to its appropriate target tissue (systemic organs and/or brain). Enzymes in the blood and appropriate tissues are believed to be able to cleave the methylenedioxy group on these analogs to yield the dihydroxy structures to achieve the observed efficacy against the diseases described earlier in the application such as Alzheimer's disease, type 2 diabetes, Parkinson's disease and other amyloid diseases and synucleinopathies.

1B

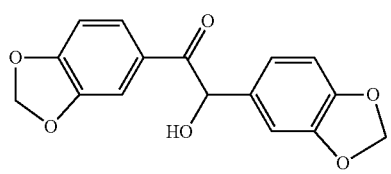

bis(3,4-methylenedioxy)benzoin

2B

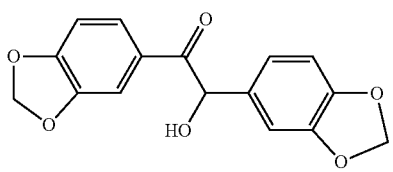

bis(3,4-methylenedioxy)desoxybenzoin

3B

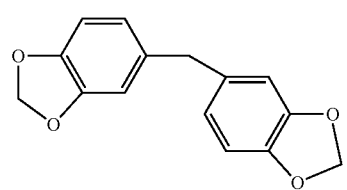

1,1-bis(3,4-methylenedioxyphenyl)methane

-continued

4B

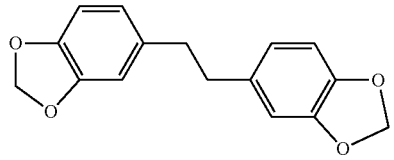

1,2-bis(3,4-methylenedioxyphenyl)ethane

5B

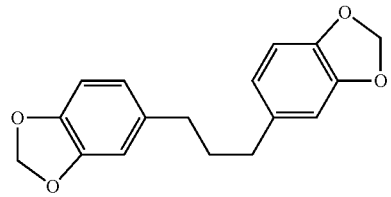

1,3-bis(3,4-methylenedioxyphenyl)propane

6B

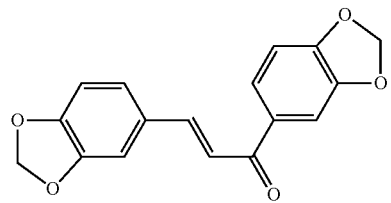

bis(3,4-methylenedioxyphenyl)chalcone

7B

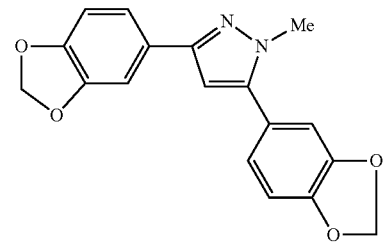

3,5-bis(3,4-methylenedioxyphenyl)-1-methyl-1H-pyrazoline

8B

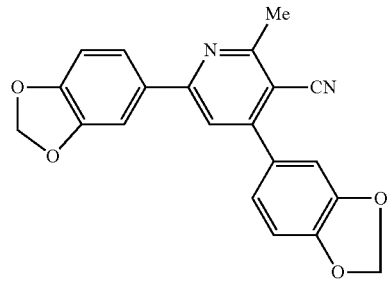

4,6-bis(3,4-methylenedioxyphenyl)-
3-cyano-2-methylpyridine

9B

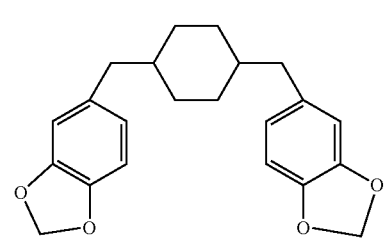

1,4-bis(3,4-methylenedioxybenzyl)piperazine

10B

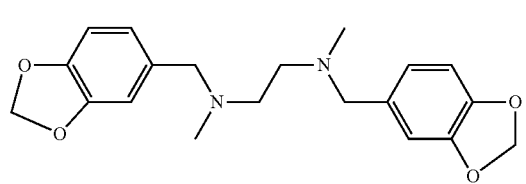

N,N'-bis(3,4-methylenedioxybenzyl)-
N,N'-dimethyl-ethylenediamine

11B

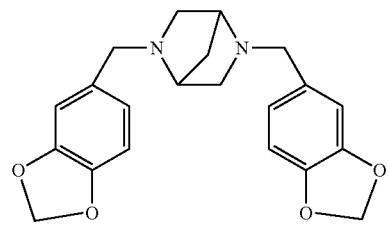

2,5-bis(3,4-methylenedioxybenzyl)-2,5-
diaza[2,2,1]-bicycloheptane

12B

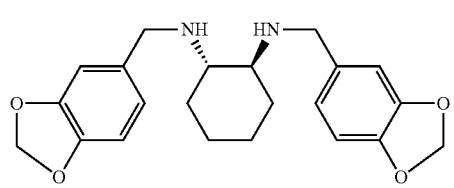

N,N'-bis(3,4-methylenedioxybenzyl)-trans-
1,2-diaminocyclohexane

13B

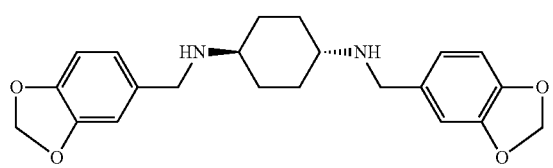

N,N'-bis(3,4-methylenedioxybenzyl)-trans-
1,4-diaminocyclohexane

14B

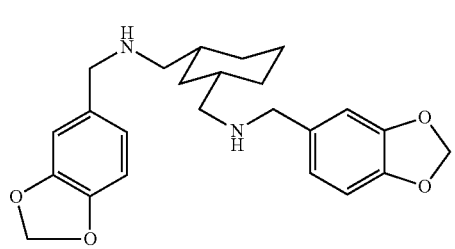

N,N'-bis(3,4-methylenedioxybenzyl)-cis-
1,3-bis-aminomethylcyclohexane

15B

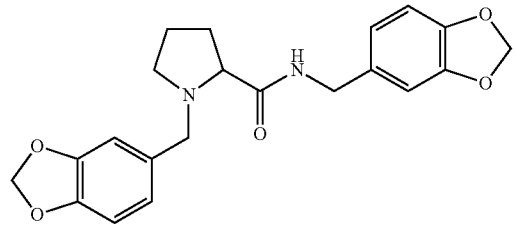

N-(3,4-methylenedioxybenzyl)proline 3,4-
methylenedioxybenzylamide

16B

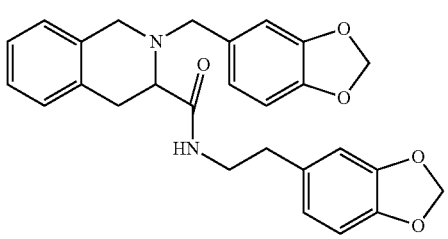

2-(3,4-methylenedioxybenzyl)isoquinoline-3-
carboxylic acid 3,4-methylenedioxyphenethylamide

17B

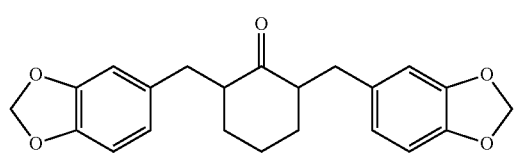

2,6-bis(3,4-methylenedioxybenzyl)cyclohexanone

18B

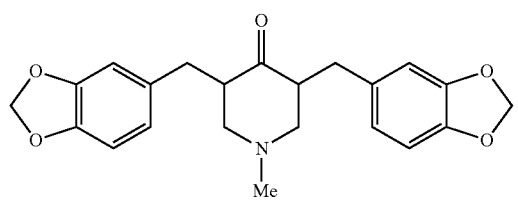

3,5-bis(3,4-methylenedioxybenzyl)-1-methyl-4-piperidinone

19B

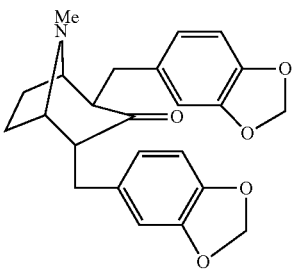

2,4-bis(3,4-methylenedioxybenzyl)-3-tropinone

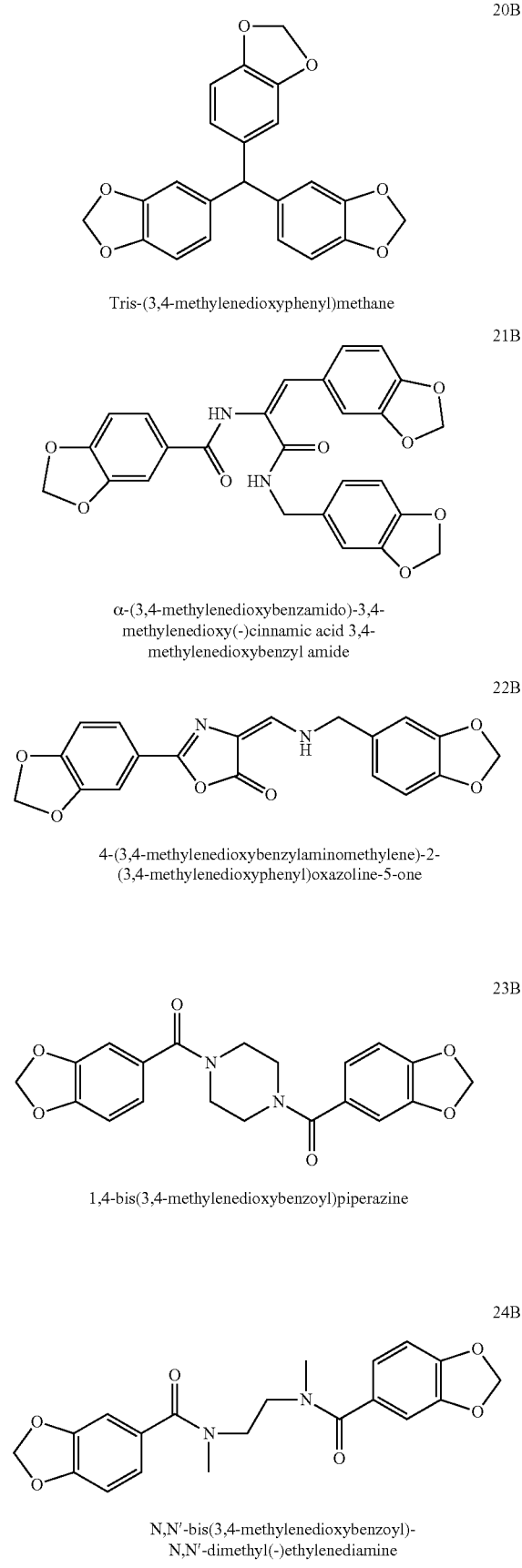

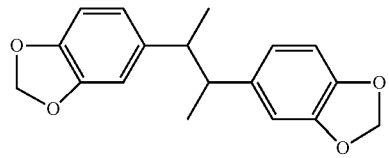

2,3-bis(3,4-methylenedioxyphenyl)butane

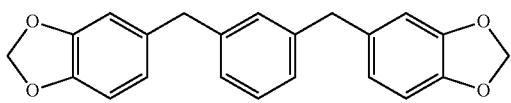

1,3-bis(3,4-methylenedioxybenzyl)benzene

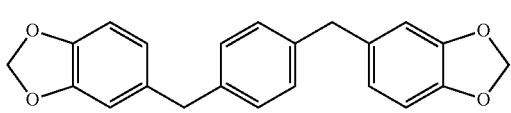

1,4-bis(3,4-methylenedioxybenzyl)benzene

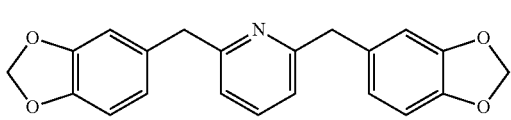

2,6-bis(3,4-methylenedioxybenzyl)pyridine

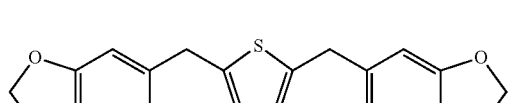

2,5-bis(3,4-methylenedioxybenzyl)thiophene

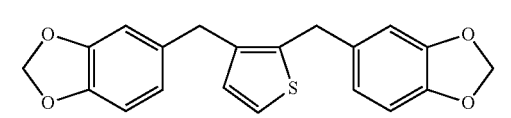

2,3-bis(3,4-methylenedioxybenzyl)thiophene

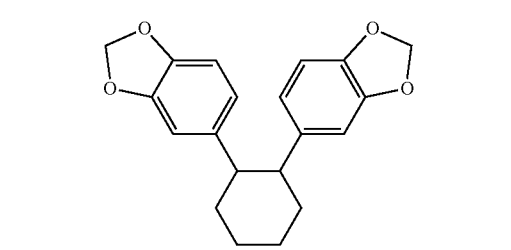

1,2-bis(3,4-methylenedioxyphenyl)cyclohexane

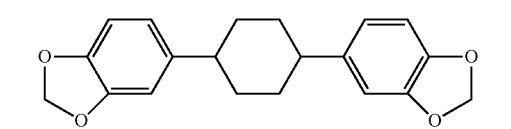

1,4-bis(3,4-methylenedioxyphenyl)cyclohexane

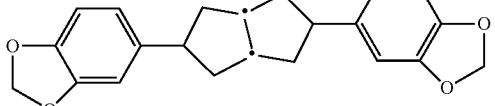

3,7-bis(3,4-methylenedioxyphenyl)bicyclo[3,3,0](-)octane

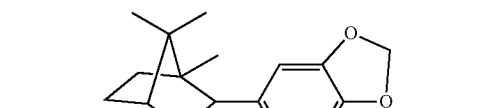

2,3-bis(3,4-methylenedioxyphenyl)-
1,7,7-trimethyl-bicyclo[2,2,1]heptane

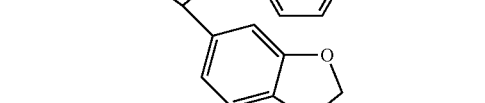

1,2-bis(3,4-methylenedioxyphenoxy)ethane

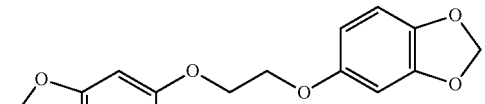

1,3-bis(3,4-methylenedioxyphenoxy)propane

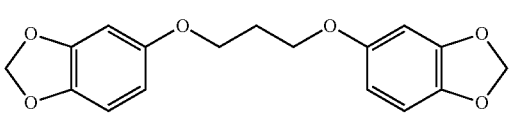

trans-1,2-bis(3,4-methylenedioxyphenoxy)(-)cyclopentane

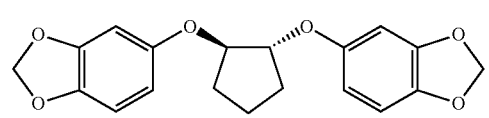

N-(3,4-methylenedioxybenzyl)-3-(3,4-methylenedioxy(-)phenoxy)-2-hydroxypropylamine

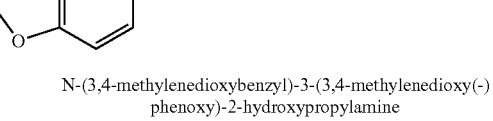

3,4-methylenedioxyphenoxy acetic acid
3,4-methylenedioxyanilide

46B

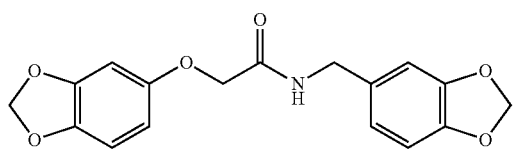

3,4-methylenedioxyphenoxyacetic acid
3,4-methylenedioxybenzylamide

47B

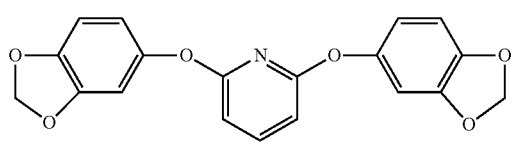

3,4-methylenedioxyphenoxy acetic acid
3,4-methylenedioxyphenethylamide

48B

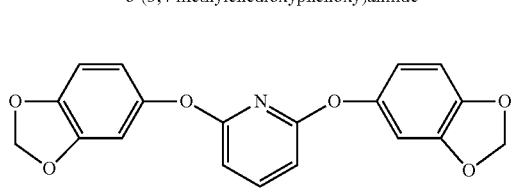

3,4-methylenedioxybenzoic acid
p-(3,4-methylenedioxyphenoxy)anilide

49B

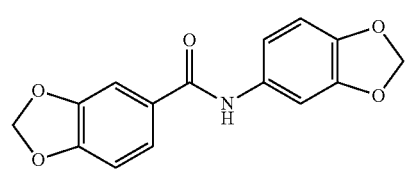

3,4-methylenedioxybenzoic acid
o-(3,4-methylenedioxyphenoxy)anilide

50B

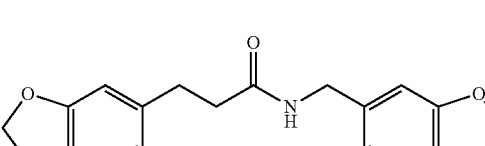

2,6-bis(3,4-methylenedioxyphenoxy)pyridine

51B

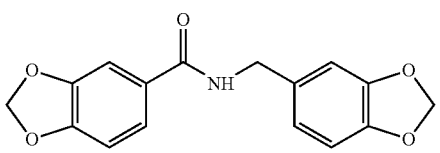

3,4-methylenedioxybenzoic acid
3,4-methylenedioxyanilide

52B

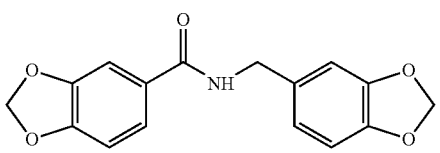

3,4-methylenedioxybenzoic acid
3,4-methylenedioxybenzylamide

53B

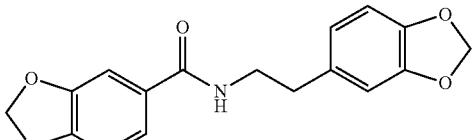

3,4-methylenedioxybenzoic acid
3,4-methylenedioxyphenethylamide

54B

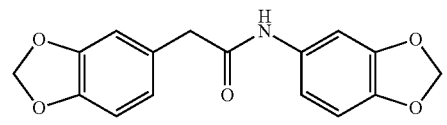

3,4-methylenedioxyphenylacetic acid
3,4-methylenedioxyanilide

55B

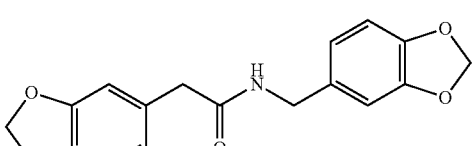

3,4-methylenedioxyphenylacetic acid
3,4-methylenedioxybenzylamide

56B

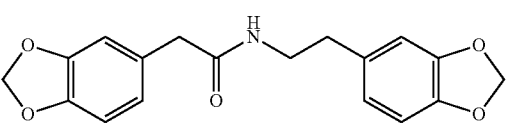

3,4-methylenedioxyphenylacetic acid
3,4-methylenedioxyphenethylamide

57B

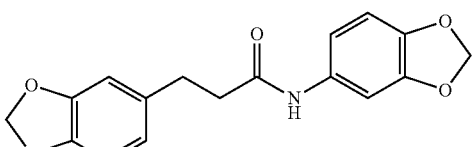

3-(3,4-methylenedioxyphenyl) propionic acid
3,4-methylenedioxyanilide

58B

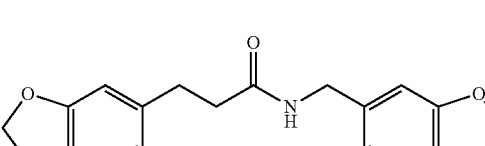

3-(3,4-methylenedioxyphenyl)propionic acid
3,4-methylenedioxybenzylamide

-continued

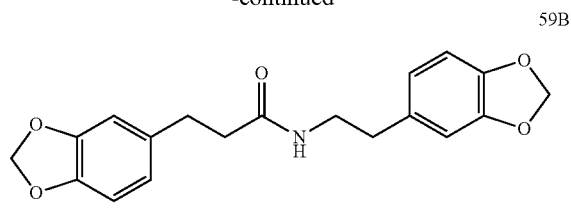

3-(3,4-methylenedioxyphenyl)propionic acid
3,4-methylenedioxyphenethylamide

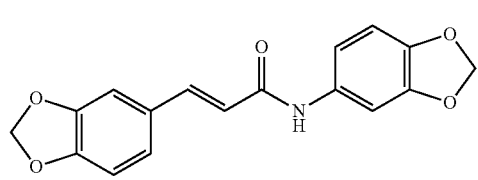

3,4-methylenedioxycinnamic acid
3,4-methylenedioxyanilide

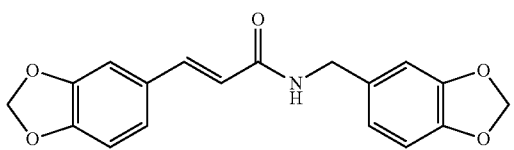

3,4-methylenedioxycinnamic acid
3,4-methylenedioxybenzylamide

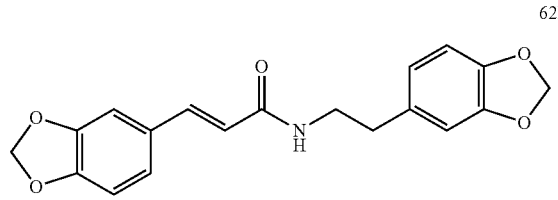

3,4-methylenedioxycinnamic acid
3,4-methylenedioxyphenethylamide

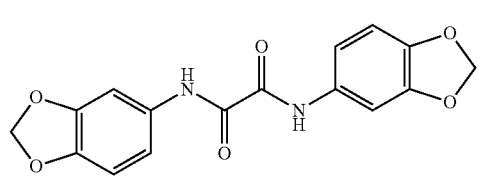

Oxalic acid bis(3,4-methylene-dioxyanilide)

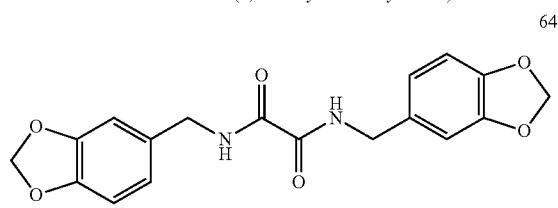

Oxalic acid bis(3,4-methylene-dioxybenzylamide)

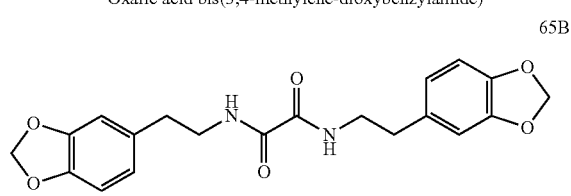

Oxalic acid bis (3,4-methylene-dioxyphenethylamide)

-continued

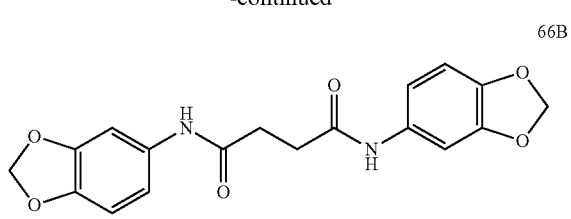

Succinic acid bis(3,4-methylene-dioxyanilide)

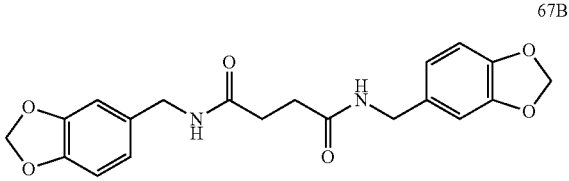

Succinic acid bis(3,4-methylene-dioxybenzylamide)

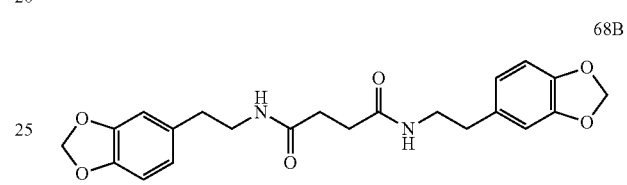

Succinic acid bis(3,4-methylene-dioxyphenethylamide)

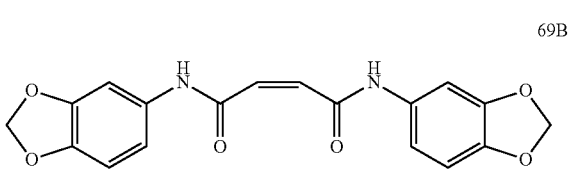

Maleic acid bis(3,4-methylene-dioxyanilide)

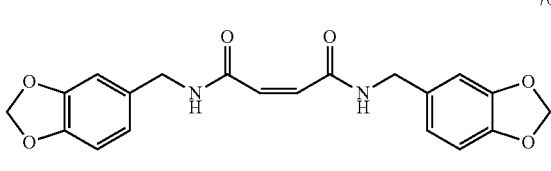

Maleic acid bis(3,4-methylene-dioxybenzylamide)

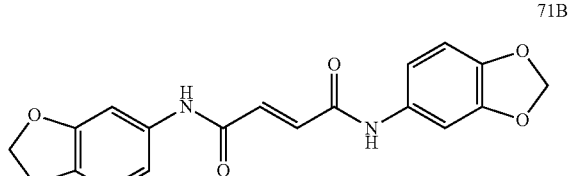

Fumaric acid bis-(3,4-methylenedioxy-anilide)

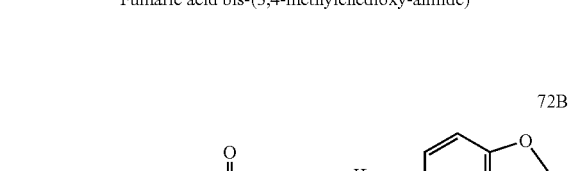

Furmaric acid bis-(3,4-methylenedioxy-benzylamide)

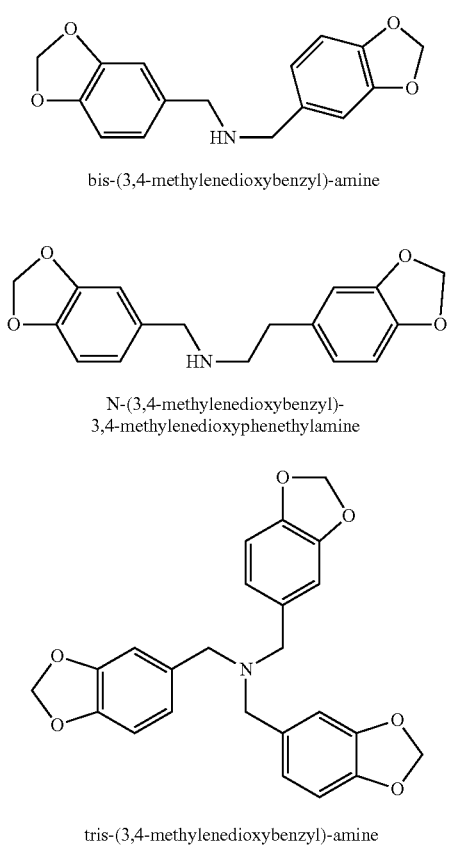

bis-(3,4-methylenedioxybenzyl)-amine 73B

N-(3,4-methylenedioxybenzyl)-3,4-methylenedioxyphenethylamine 74B tris-(3,4-methylenedioxybenzyl)-amine 75B 1,3-bis-(3,4-methylenedioxyphenyl)-urea 76B

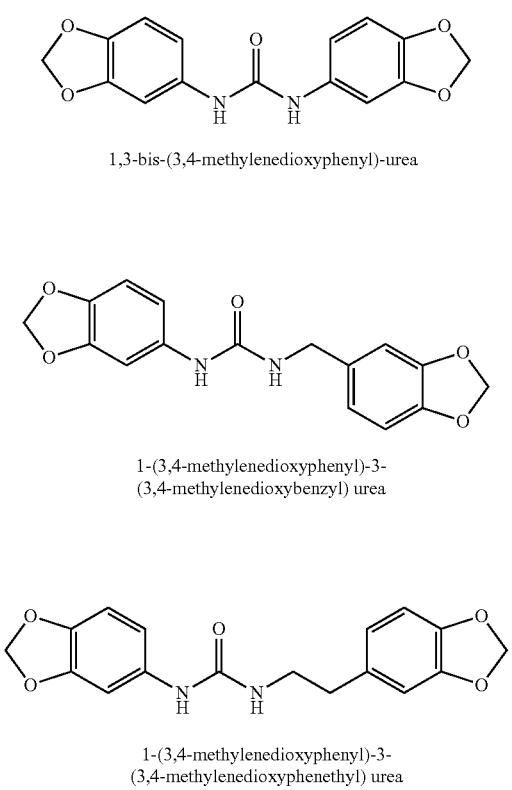

1-(3,4-methylenedioxyphenyl)-3-(3,4-methylenedioxybenzyl) urea 77B 1-(3,4-methylenedioxyphenyl)-3-(3,4-methylenedioxyphenethyl) urea 78B

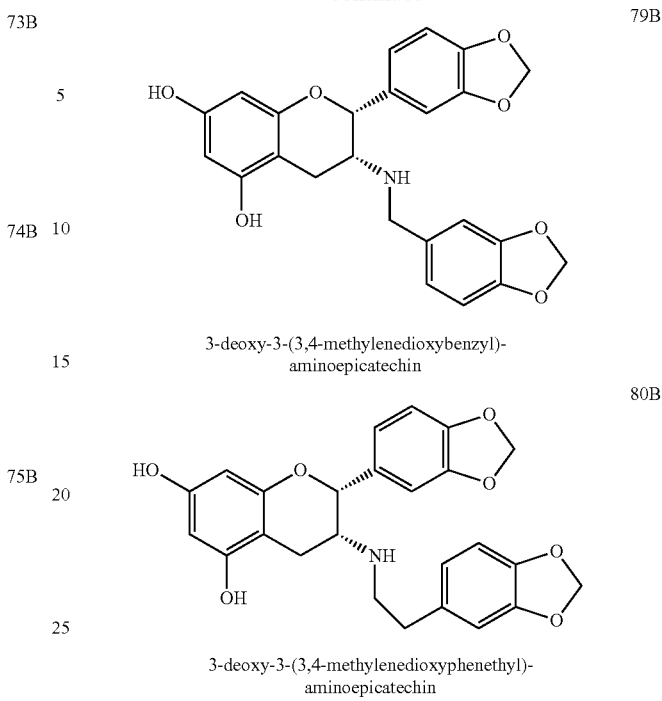

3-deoxy-3-(3,4-methylenedioxybenzyl)-aminoepicatechin 79B 3-deoxy-3-(3,4-methylenedioxyphenethyl)-aminoepicatechin 80B

Example 31

Acylated Compounds

Another potential strategy for the delivery of the bis- and tris-dihydroxyaryl compounds of this invention to improve and/or cause more favorable metabolism and bioavailability characteristics, involves methods of protecting the hydroxy groups as their pharmaceutically acceptable esters. Ester groups replacing the hydroxy groups also tend to make the compounds more stable, and less likely to be altered or degraded due to oxidation of the hydroxyl groups.

The compound table below illustrates the acetyl esters of the 80 dihydroxyaryl compounds of Examples 1-23 and 28 are presented below in which the OH groups are replaced by acetyl groups. The illustration of acetyl esters here is merely exemplary for the class of pharmaceutically acceptable esters that are part of the compounds of this invention and may be prepared by analogous methods. The compounds of Example 29 also form pharmaceutically acceptable esters in the same manner, and these compounds, though not illustrated in the compound table below, are also compounds of this invention.

These compounds are expected to be efficacious in their ability to treat amyloid diseases and synucleinopathies once the ester linkages are cleaved (by enzymes in the plasma or in the brain tissue), and the hydroxyl groups are regenerated. Replacement of the hydroxyl groups with ester groups will yield prodrugs that are believed to improve toxicity (i.e. being less toxic), metabolism (since the OH groups will be less likely to be altered by methylation, glucuronidation and sulfation), and bioavailability. In this prodrug concept, it is believed that the prodrug conversion takes place in the plasma (following its protection through the gut), and closer to its appropriate target tissue (systemic organs for the treatment of systemic amyloid diseases and/or brain for the treatment of Alzheimer's, Parkinson's, type 2 diabetes, and other Aβ, amyloid and synuclein diseases). Enzymes in the blood and appropriate tissues are believed to be able to cleave the ester linkages on these pharmaceutically acceptable esters to yield the dihydroxy structures important for the observed efficacy against Alzheimer's disease, other amyloid diseases (such as IAPP fibrils in type 2 diabetes), and α-synuclein/NAC fibrils, such as in Parkinson's disease, and other synucleinopathies.

The pharmaceutically acceptable esters of compounds #1 through #86 are prepared by methods well known to persons of ordinary skill in the art, such as by reaction of the dihydroxyaryl compounds with pharmaceutically acceptable acids, especially in activated form (such as the acyl halides) and/or in the presence of reagents facilitating esterification (such as an acidic catalyst) and/or under conditions favoring esterification (such as by conducting the reaction under conditions where the water formed in the esterification is removed, e.g. by distillation). Methods of esterification of phenolic hydroxyl groups are well known to persons of ordinary skill in the art.

Suitable acids for the formation of pharmaceutically acceptable esters are the $C_{2-6}$ alkanoic acids (acetic acid, propionic acid, and the like), benzoic acid, arylalkanoic acids (phenylacetic acid, and the like); though many other acids are suitable for the formulation of pharmaceutically acceptable esters, and a person of ordinary skill in the art will have no difficulty in choosing a suitable acid.

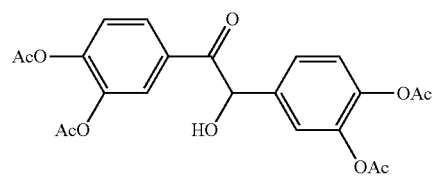

bis(3,4-diacetoxy)benzoin

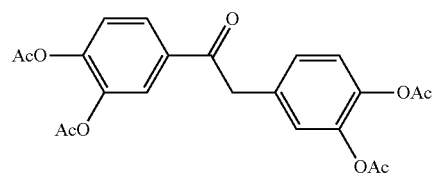

bis(3,4-diacetoxy)desoxybenzoin

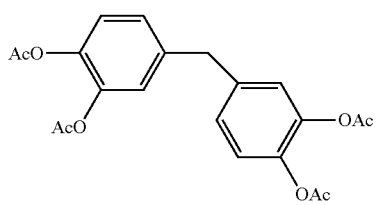

1,1-bis(3,4-diacetoxyphenyl)methane

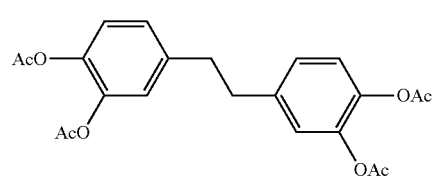

1,2-bis(3,4-diacetoxyphenyl)ethane

-continued

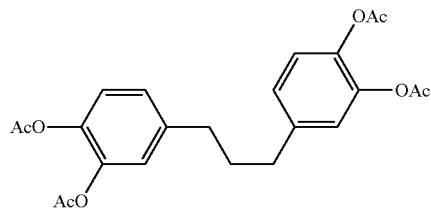

1,3-bis(3,4-diacetoxyphenyl)propane

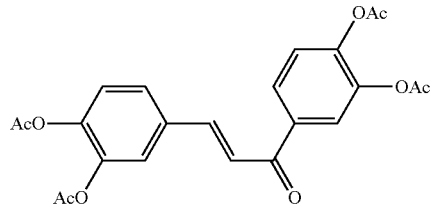

bis(3,4-diacetoxy)chalcone

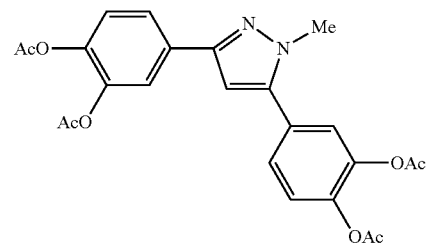

3,5-bis(3,4-diacetoxyphenyl)-1-methyl-1H-pyrazoline

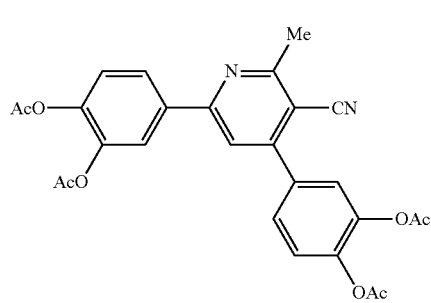

4,6-bis(3,4-diacetoxyphenyl)-3-cyano-2-methylpyridine

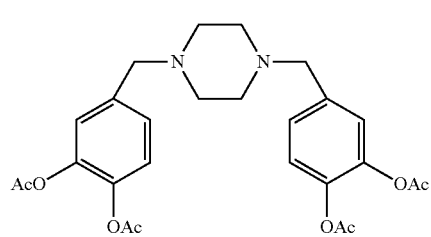

1,4-bis(3,4-diacetoxybenzyl)piperazine

-continued

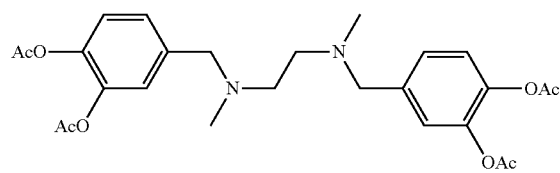

N,N'-bis(3,4-diacetoxybenzyl)-
N,N'-dimethyl-ethylenediamine

10C

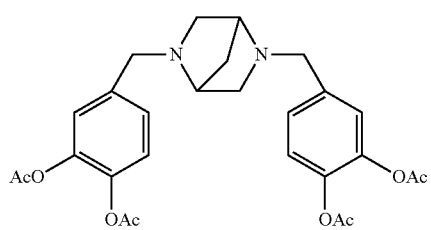

2,5-bis(3,4-diacetoxybenzyl)-2,5-diaza[2,2,1]-bicycloheptane

11C

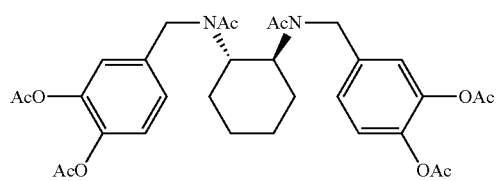

N,N'-bis(acetyl)-bis(3,4-diacetoxybenzyl)-trans-1,2-
diaminocyclohexane

12C

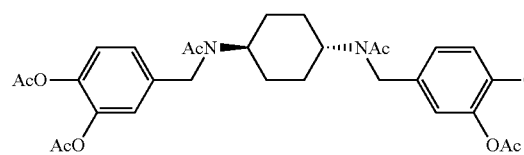

N,N'-bis(acetyl)-bis(3,4-diacetoxybenzyl)-trans-
1,4-diaminocyclohexane

13C

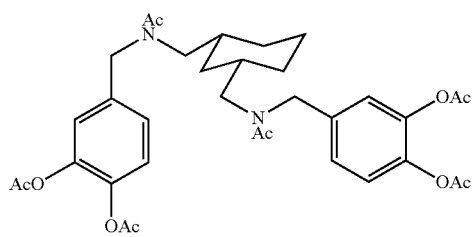

N,N'-bis(acetyl)-bis(3,4-diacetoxybenzyl)-cis-
1,3-bis-aminomethylcyclohexane

14C

-continued

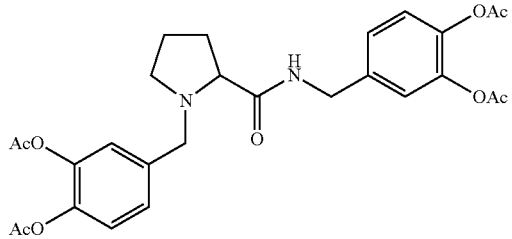

N-(3,4-diacetoxybenzyl)proline 3,4-
diacetoxybenzylamide

15C

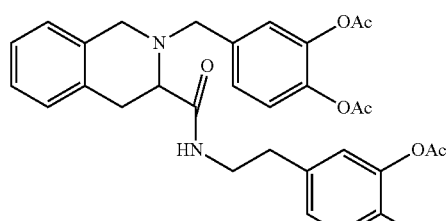

2-(3,4-diacetoxybenzyl)isoquinoline-3-
carboxylic acid 3,4-diacetoxyphenethylamide

16C

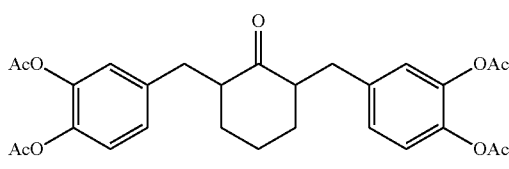

2,6-bis(3,4-diacetoxybenzyl)cyclohexanone

17C

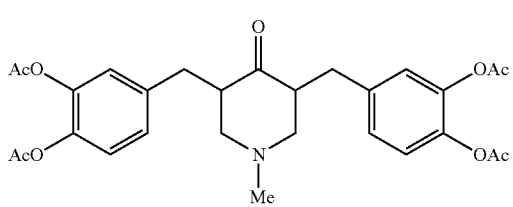

3,5-bis(3,4-diacetoxybenzyl)-1-methyl-4-piperidinone

18C

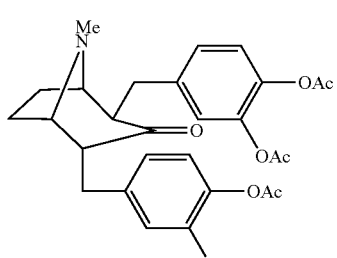

2,4-bis(3,4-diacetoxybenzyl)-3-tropinone

19C

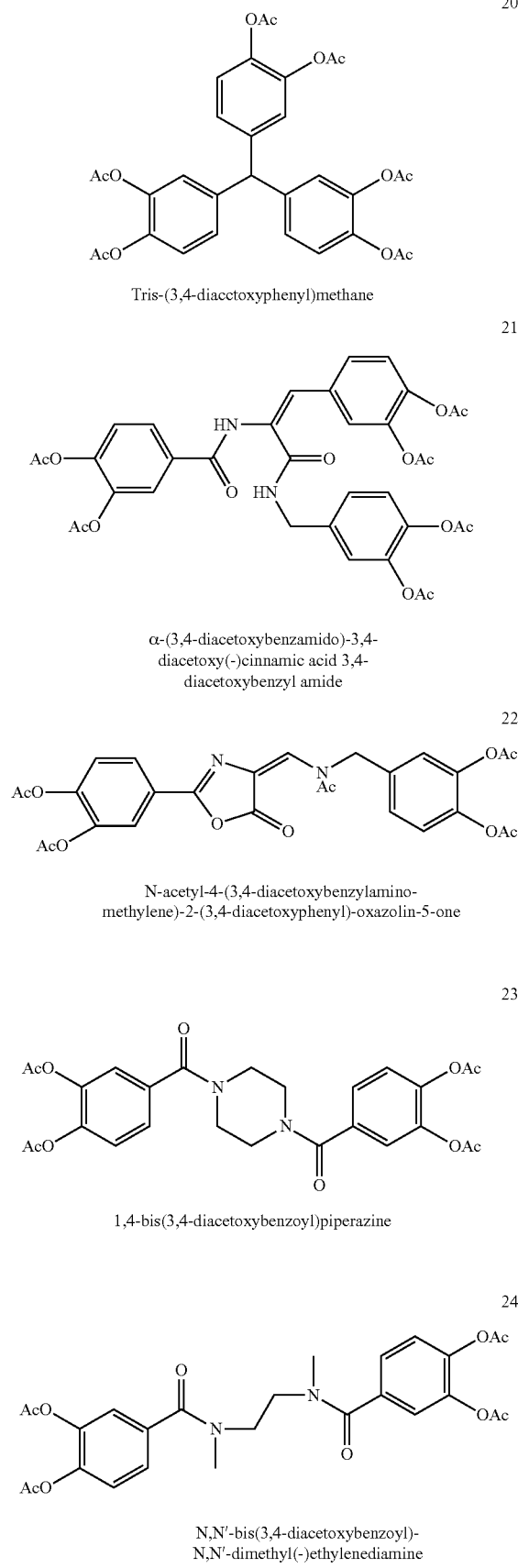
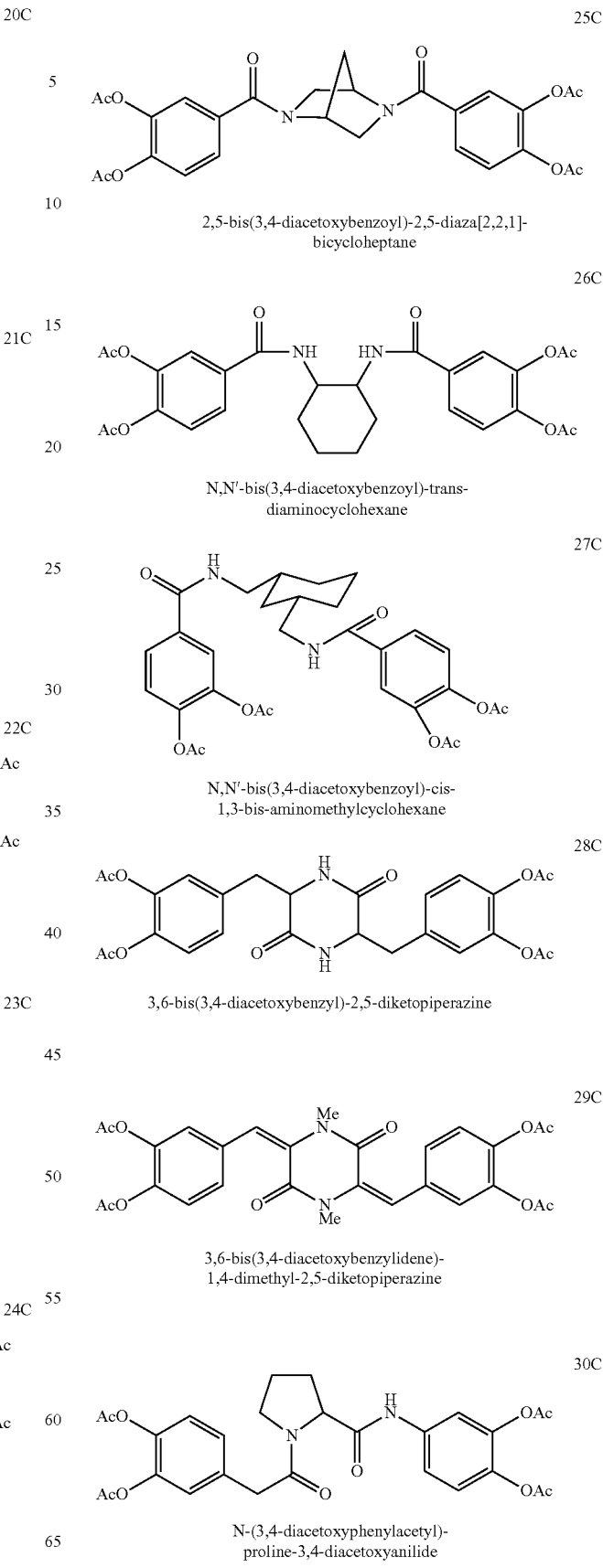

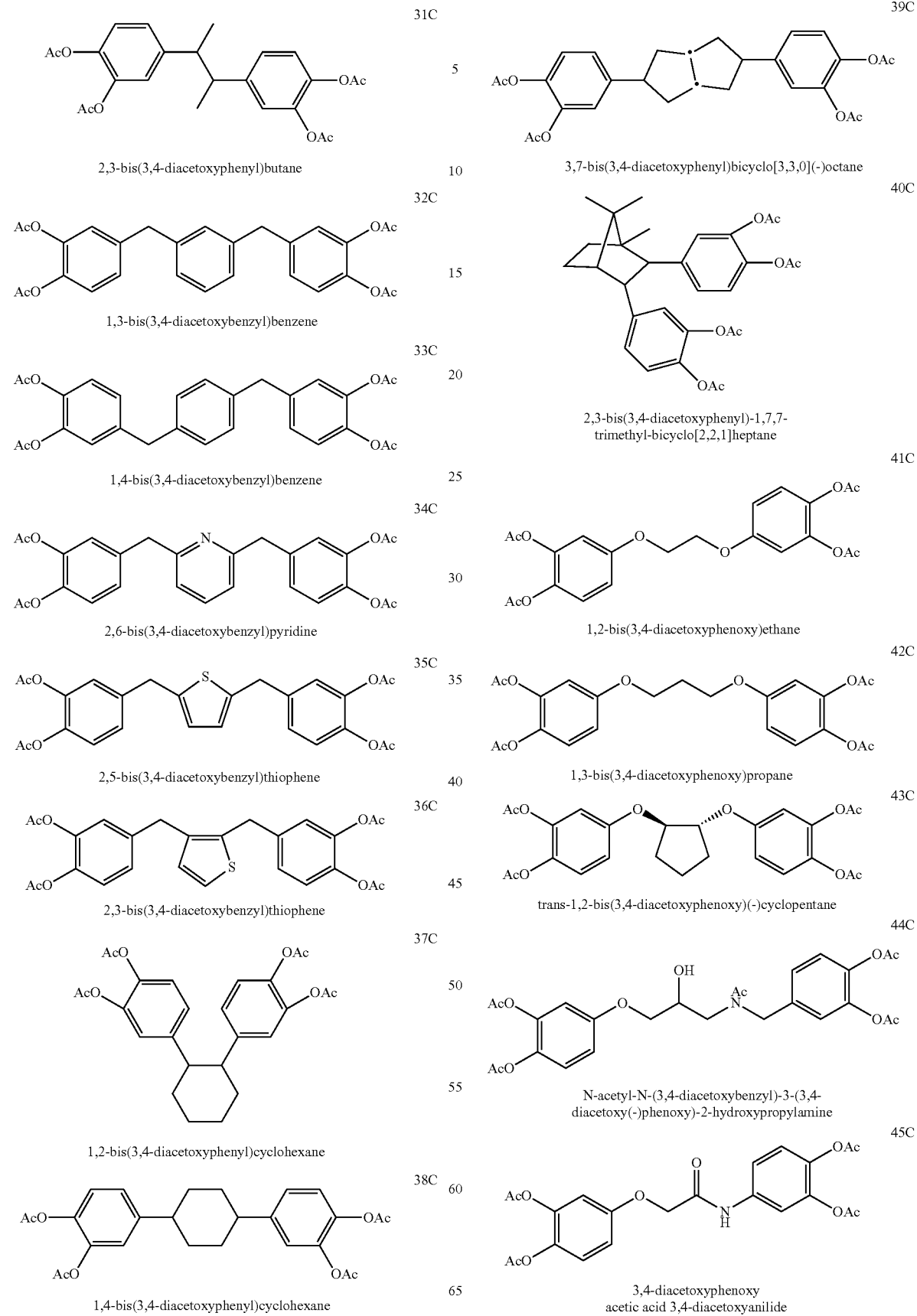

46C

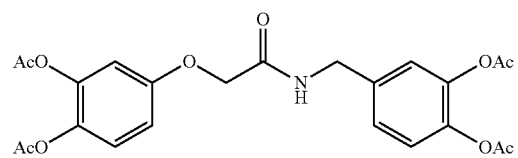

3,4-diacetoxyphenoxyacetic acid
3,4-diacetoxybenzylamide

47C

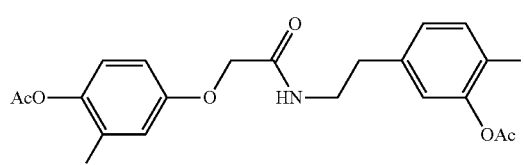

3,4-diacetoxyphenoxy acetic acid
3,4-diacetoxyphenethylamide

48C

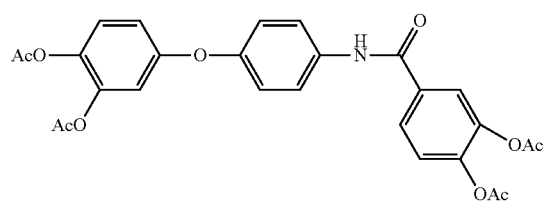

3,4-diacetoxybenzoic acid p-(3,4-diacetoxyphenoxy) anilide

49C

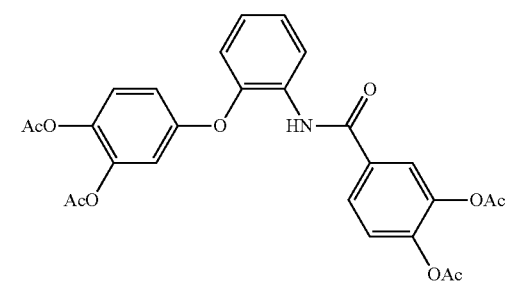

3,4-diacetoxybenzoic acid
o-(3,4-diacetoxyphenoxy)anilide

50C

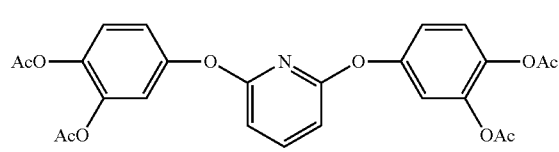

2,6-bis(3,4-diacetoxyphenoxy)pyridine

51C

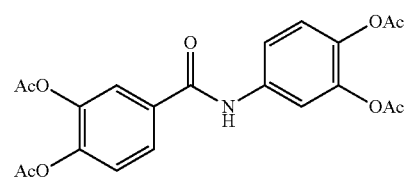

3,4-diacetoxybenzoic acid
3,4-diacetoxyanilide

52C

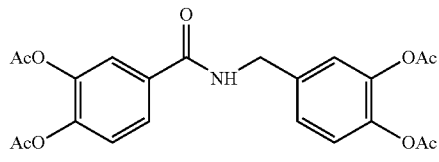

3,4-diacetoxybenzoic acid
3,4-diacetoxybenzylamide

53C

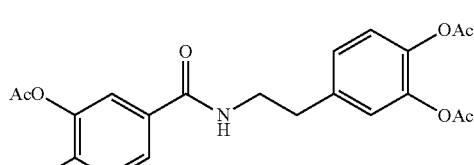

3,4-diacetoxybenzoic acid
3,4-diacetoxyphenethylamide

54C

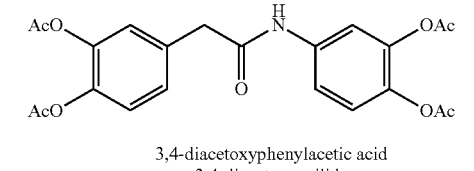

3,4-diacetoxyphenylacetic acid
3,4-diacetoxyanilide

55C

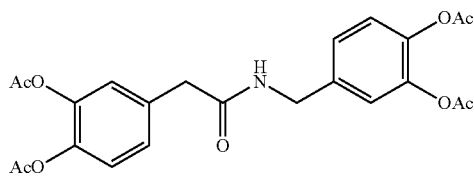

3,4-diacetoxyphenylacetic acid
3,4-diacetoxybenzylamide

56C

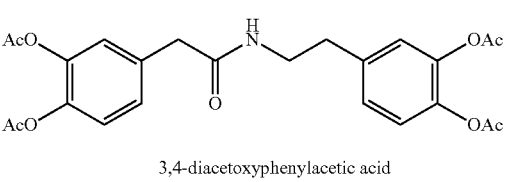

3,4-diacetoxyphenylacetic acid
3,4-diacetoxyphenethylamide

57C

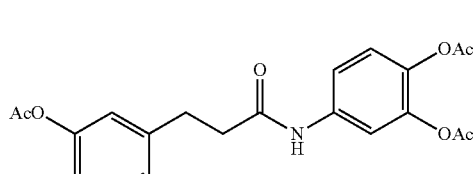

3,(3,4-diacetoxyphenyl) propionic acid
3,4-diacetoxyanilide

58C

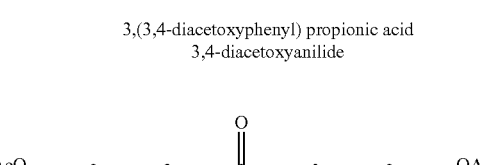

3-(3,4-diacetoxyphenyl)propionic acid
3,4-diacetoxybenzylamide

-continued

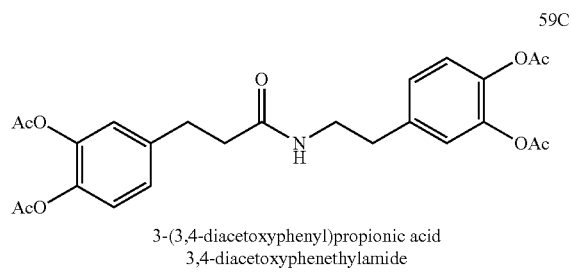

3-(3,4-diacetoxyphenyl)propionic acid
3,4-diacetoxyphenethylamide

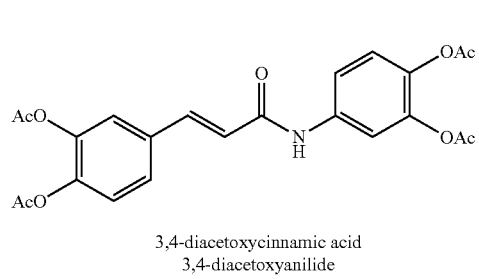

3,4-diacetoxycinnamic acid
3,4-diacetoxyanilide

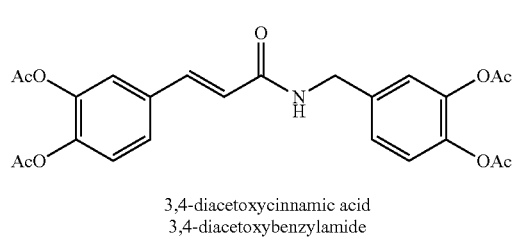

3,4-diacetoxycinnamic acid
3,4-diacetoxybenzylamide

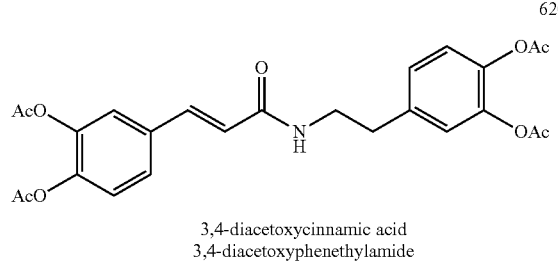

3,4-diacetoxycinnamic acid
3,4-diacetoxyphenethylamide

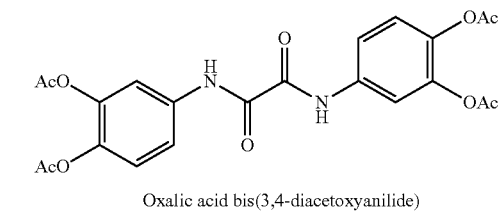

Oxalic acid bis(3,4-diacetoxyanilide)

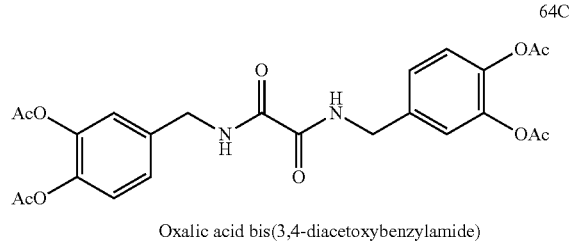

Oxalic acid bis(3,4-diacetoxybenzylamide)

-continued

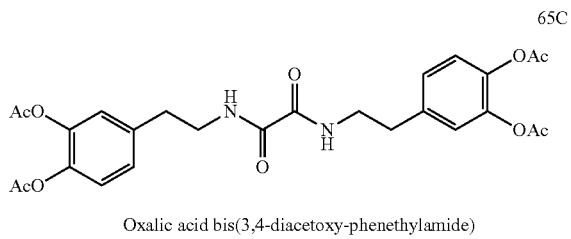

Oxalic acid bis(3,4-diacetoxy-phenethylamide)

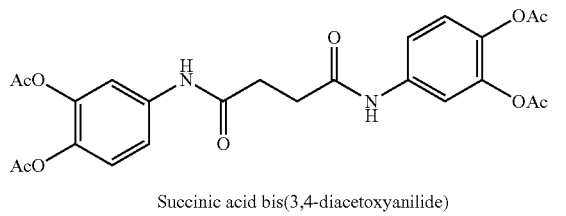

Succinic acid bis(3,4-diacetoxyanilide)

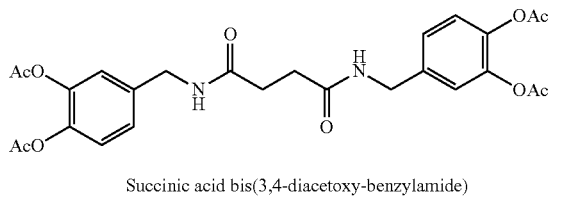

Succinic acid bis(3,4-diacetoxy-benzylamide)

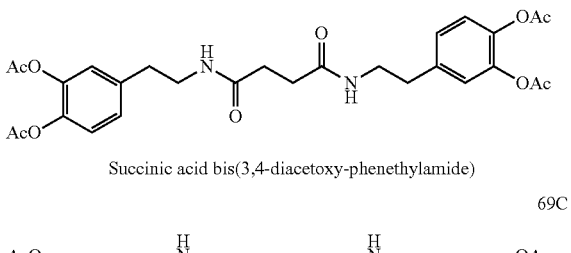

Succinic acid bis(3,4-diacetoxy-phenethylamide)

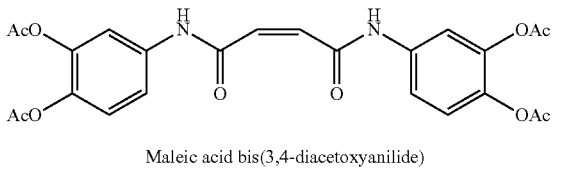

Maleic acid bis(3,4-diacetoxyanilide)

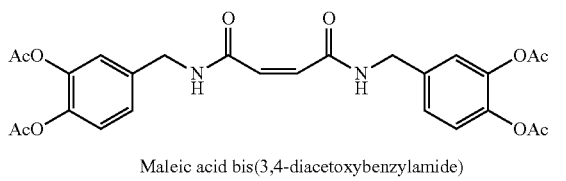

Maleic acid bis(3,4-diacetoxybenzylamide)

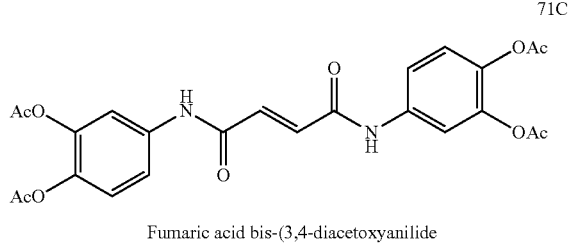

Fumaric acid bis-(3,4-diacetoxyanilide

-continued

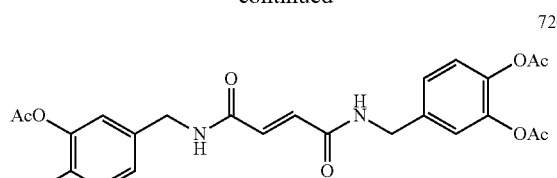

Fumaric acid bis-(3,4-diacetoxybenzylamide)

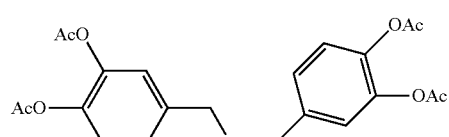

N-acetyl-bis-(3,4-diacetoxybenzyl)amine

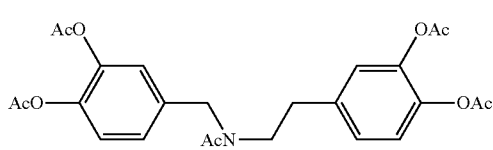

N-acetyl-N-(3,4-diacetoxybenzyl)-3,4-diacetoxyphenethylamine

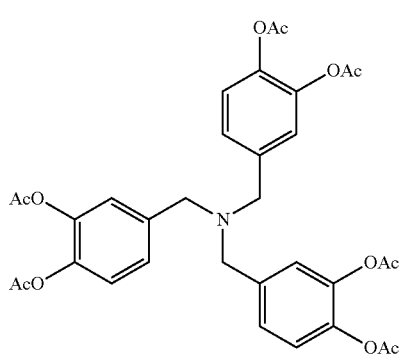

tris-(3,4-diacetoxybenzyl)-amine

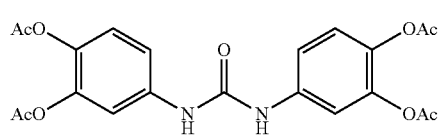

1,3-bis-(3,4-diacetoxyphenyl)-urea

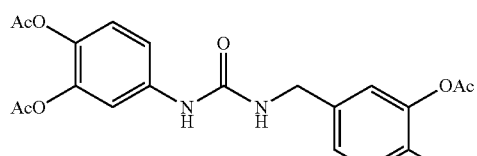

1-(3,4-diacetoxyphenyl)-3-(3,4-diacetoxybenzyl) urea

-continued

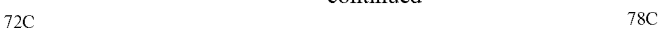

1-(3,4-diacetoxyphenyl)-3-(3,4-diacetoxyphenethyl) urea

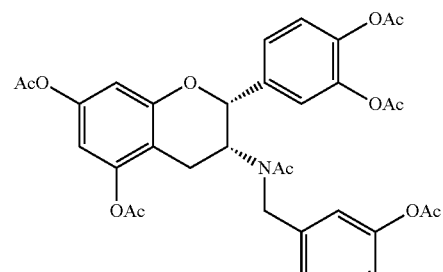

N-acetyl-3-deoxy-3-(3,4-diacetoxy-benzyl)-amino-5,7,3',4'-tetraacetyl-epicatechin

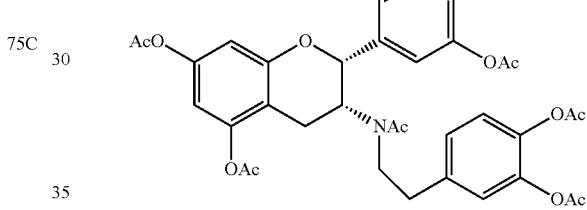

N-acetyl-3-deoxy-3-(3,4-diacetoxy-phenethyl)-amino-5,7,3',4'-tetraacetyl-epicatechin Example 32

Compositions of Compounds of this Invention

The compounds of this invention, as mentioned previously, are desirably administered in the form of pharmaceutical compositions. Suitable pharmaceutical compositions, and the method of preparing them, are well-known to persons of ordinary skill in the art and are described in such treatises as *Remington: The Science and Practice of Pharmacy*, A. Gennaro, ed., 20th edition, Lippincott, Williams & Wilkins, Philadelphia, Pa.

Representative compositions are as follows:

Oral Tablet Formulation

An oral tablet formulation of a compound of this invention is prepared as follows:

|  | % w/w |
| --- | --- |
| Compound of this invention | 10.0 |
| Magnesium stearate | 0.5 |
| Starch | 2.0 |
| Hydroxypropylmethylcellulose | 1.0 |
| Microcrystalline cellulose | 86.5 |

The ingredients are mixed to homogeneity, then granulated with the aid of water, and the granulates dried. The granulate is then compressed into tablets sized to give a suitable dose of the compound. The tablet is optionally coated by applying a suspension of a film forming agent (e.g. hydroxypropylmethylcellulose), pigment (e.g. titanium dioxide), and plasticizer (e.g. diethyl phthalate), and drying the film by evaporation of the solvent. The film coat may comprise, for example, 2-6% of the tablet weight.

Oral Capsule Formulation

The granulate from the previous section of this Example is filled into hard gelatin capsules of a size suitable to the intended dose. The capsule is banded for sealing, if desired.

Softgel Formulation

A softgel formulation is prepared as follows:

|  | % w/w |
| --- | --- |
| Compound of this invention | 20.0 |
| Polyethylene glycol 400 | 80.0 |

The compound is dissolved or dispersed in the polyethylene glycol, and a thickening agent added if required. A quantity of the formulation sufficient to provide the desired dose of the compound is then filled into softgels.

Parenteral Formulation

A parenteral formulation is prepared as follows:

|  | % w/w |
| --- | --- |
| Compound of this invention | 1.0 |
| Normal saline | 99.0 |

The compound is dissolved in the saline, and the resulting solution is sterilized and filled into vials, ampoules, and pre-filled syringes, as appropriate.

Controlled-Release Oral Formulation

A sustained release formulation may be prepared by the method of U.S. Pat. No. 4,710,384, as follows:

One Kg of a compound of this invention is coated in a modified Uni-Glatt powder coater with Dow Type 10 ethyl cellulose. The spraying solution is an 8% solution of the ethyl cellulose in 90% acetone to 10% ethanol. Castor oil is added as plasticizer in an amount equal to 20% of the ethyl cellulose present. The spraying conditions are as follows: 1) speed, 1 liter/hour; 2) flap, 10-15%; 3) inlet temperature, 50° C., 4) outlet temperature, 30° C., 5) percent of coating, 17%. The coated compound is sieved to particle sizes between 74 and 210 microns. Attention is paid to ensure a good mix of particles of different sizes within that range. Four hundred mg of the coated particles are mixed with 100 mg of starch and the mixture is compressed in a hand press to 1.5 tons to produce a 500 mg controlled release tablet.

The present invention is not limited in scope by the specific embodiments described herein. Indeed, various modifications of the invention in addition to those described will become apparent to those skilled in the art from the foregoing descriptions. Such modifications are intended to fall within the scope of the appended claims. Various publications are cited herein, the disclosures of which are incorporated by reference in their entireties.

We claim:

1. A method of relieving a amyloid disease or a synucleinopathy in a mammal suffering therefrom, comprising administration to the mammal of a therapeutically effective amount of 3,4,3',4'-tetrahydroxychalcone, wherein the synucleinopathy is Parkinson's disease.

2. The method of claim 1 where the mammal is a human.

3. The method of claim 1 where the amount of 3,4,3',4'-tetrahydroxychalcone administered is between 0.1 mg/Kg/day and 1000 mg/Kg/day.

4. The method of claim 1 where the amount of 3,4,3',4'-tetrahydroxychalcone administered is between 1 mg/Kg/day and 100 mg/Kg/day.

5. The method of claim 1 where the amount of 3,4,3',4'-tetrahydroxychalcone administered is between 10 mg/Kg/day and 100 mg/Kg/day.

* * * * *